(12) United States Patent
Miller et al.

(10) Patent No.: US 12,329,755 B2
(45) Date of Patent: Jun. 17, 2025

(54) BROMODOMAIN INHIBITORS TO TARGET THERAPY-RESISTANT CANCER

(71) Applicant: University of Tennessee Research Foundation, Knoxville, TN (US)

(72) Inventors: Duane Miller, Memphis, TN (US); Lawrence M. Pfeffer, Memphis, TN (US); Yali He, Memphis, TN (US); Debolina Ganguly, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 732 days.

(21) Appl. No.: 17/639,114

(22) PCT Filed: Aug. 28, 2020

(86) PCT No.: PCT/US2020/048396
§ 371 (c)(1),
(2) Date: Feb. 28, 2022

(87) PCT Pub. No.: WO2021/041801
PCT Pub. Date: Mar. 4, 2021

(65) Prior Publication Data
US 2022/0296592 A1    Sep. 22, 2022

Related U.S. Application Data
(60) Provisional application No. 62/893,667, filed on Aug. 29, 2019.

(51) Int. Cl.
| | | |
|---|---|---|
| C07D 487/08 | (2006.01) |
| A61K 31/17 | (2006.01) |
| A61K 31/495 | (2006.01) |
| A61K 31/4995 | (2006.01) |
| A61P 35/00 | (2006.01) |

(52) U.S. Cl.
CPC .......... *A61K 31/4995* (2013.01); *A61K 31/17* (2013.01); *A61K 31/495* (2013.01); *A61P 35/00* (2018.01); *C07D 487/08* (2013.01)

(58) Field of Classification Search
CPC .. A61K 31/4995; A61K 31/495; A61K 31/17; C07D 487/08; A61P 35/00
See application file for complete search history.

(56) References Cited

U.S. PATENT DOCUMENTS

| | | |
|---|---|---|
| 2015/0320754 A1 | 11/2015 | Kutok et al. |
| 2016/0256448 A1 | 9/2016 | Bair et al. |
| 2017/0360760 A1 | 12/2017 | Kharenko et al. |
| 2019/0076541 A1 | 3/2019 | Phillips et al. |

FOREIGN PATENT DOCUMENTS

WO    WO 2020219362 A1    10/2020

OTHER PUBLICATIONS

Brian S. Gerstenberger, et al., Journal of Medicinal Chemistry 2016 59 (10), 4800-4811 DOI: 10.1021/acs.jmedchem.6b00012 (Year: 2016).*

Akira, S., et al., "Molecular Cloning of APRF, a novel IFN-stimulated gene factor 3 p91-related transcription factor involved in the gp 130-mediated signaling pathway." Cell, vol. 77, pp. 63-71 (1994).

Attenello, F., et al., "Chemotherapy for brain tumors with polymer drug delivery." Handbook of Clinical Neurology, vol. 104 (3rd series), pp. 339-353 (2012).

Bai et al., "BRG1 expression is increased in human glioma and controls glioma cell proliferation migration and invasion in vitro." J. Cancer Res. Clin. Oncol., vol. 138, pp. 991-998 (2012).

Bobustuc, G.C., et al., "Levetiracetam enhances p53-mediated MGMT inhibition and sensitizes glioblastoma cells to temozolomide," Neuro-Oncology, 12(9):917-927, 2010.

Bowman et al., "STATs in oncogenesis." Oncogene, vol. 19, pp. 2474-2488 (2000).

Brennan et al., "The somatic genomic landscape of glioblastoma." Cell, vol. 155, pp. 462-477 (2013).

Clarke et al., "Cancer stem cells—perspectives on current status and future directions: AACR Workshop on cancer stem cells." Cancer Res, vol. 66, pp. 9339-9344 (2006).

Du et al., "The effects of type I interferon on glioblastoma cancer stem cells." Biochem. Biophys. Res. Commun., vol. 491, pp. 343-348, doi: 10.1 016/j.bbrc.2017.07.098 (2017).

Fedorov, O et al., "Selective targeting of the BRG/PB1 bromodomains impairs embryonic and trophoblast stem cell maintenance." Sci. Adv., vol. 1, Article ID e1500723, doi: 1 0.1126/sciadv. 1500723 (2015).

Filippakopoulos, P et al., "Targeting bromodomains: epigenetic readers of lysine acetylation." Nat. Rev. Drug Discov., vol. 13, 337-356, doi:10.1038/nrd4286 (2014).

Galli, R., et al., "Isolation and characterization of tumorigenic, stem-like neural precursors from human glioblastoma." Cancer Res., vol. 64, pp. 7011-7021, doi: 10.1158/0008-5472.CAN-04-1364 (2004).

Gallo, M., et al., "MLL5 Orchestrates a Cancer Self-Renewal State by Repressing the Histone Variant H3.3 and Globally Reorganizing Chromatin." Cancer Cell, vol. 28, pp. 715-729, doi: 10.1016/j.ccell. 2015.10.005 (2015).

Gangemi, R.M., et al., "SOX2 silencing in glioblastoma tumor-initiating cells causes stop of proliferation and loss of tumorigenicity." Stem Cells, vol. 27, 40-48, doi: 10.1634/stemcells.2008-0493 (2009).

(Continued)

*Primary Examiner* — Adam C Milligan
*Assistant Examiner* — Elvie Grace Sellers
(74) *Attorney, Agent, or Firm* — Jenkins, Taylor & Hunt, P.A.

(57) ABSTRACT

Novel inhibitors of the bromodomain of Brahma-related gene 1 (BRG1) are described. Also described are methods of treating glioblastoma using inhibitors of the BRG1 bromodomain in combination with chemotherapeutics, such as DNA alkylating agents. As described herein, the inhibitors sensitize glioblastoma cells, including chemoresistant glioblastoma cells, to DNA alkylating agents, for example, temozolomide and carmustine.

28 Claims, 8 Drawing Sheets

(56) References Cited

OTHER PUBLICATIONS

Ganguly et al., "Chromatin Remodeling Factor BRG1 Regulates Stemness and Chemosensitivity of Glioma Initiating Cells." Stem Cells, vol. 36, pp. 1804-1815 (2018).
Ganguly et al., "The critical role that STAT3 plays in glioma-initiating cells: STAT3 addiction in glioma." Oncotarget, vol. 9, pp. 22095-22112 (2018).
Gao, X., et al., "ES cell pluripotency and germ-layer formation require the SWI/SNF chromatin remodeling component BAF250a." Proc. Natl. Acad. Sci. USA, vol. 105, pp. 6656-6661, doi:10.1073/pnas.0801802105 (2008).
Garner, J.M., et al., "Constitutive Activation of Signal Transducer and Activator of Transcription 3 (STAT3) and Nuclear Factor kappaB Signaling in Glioblastoma Cancer Stem Cells Regulates the Notch Pathway." J. Biol. Chem., vol. 288, pp. 26167-26176. doi:10.1074/jbc.M113.477950 (2013).
Garner, J.M., et al., "Molecular heterogeneity in a patient-derived glioblastoma xenoline is regulated by different cancer stem cell populations." PLOS One, vol. 10, Article ID e0125838, doi:10.1371/journal.pone.0125838 (2015).
Gerstenberger, B.S., et al., "Identification of a Chemical Probe for Family VIII Bromodomains through Optimization of a Fragment Hit." Journal of Medicinal Chemistry, vol. 59, pp. 4800-4811 (2016).
Giraud, S., et al., "Implication of BRG1 and cdk9 in the STAT3-mediated activation of the p21waf1 gene." Oncogene, vol. 23, pp. 7391-7398, doi: 10.1 038/sj.onc. 1207972 (2004).
Guerrero-Martinez et al., "High expression of SMARCA4 or SMARCA2 is frequently associated with an opposite prognosis in cancer." Sci. Rep., vol. 8, pp. 2043, doi: 10.1038/s41598-018-20217-3 (2018).
Gutenberg, A., et al., "MGMT Promoter Methylation Status and Prognosis of Patients with Primary or Recurrent Glioblastoma Treated with Carmustine Wafers," British Journal of Neurosurgery, vol. 27, Issue. 6, doi:10.3109/02688697.2013.791664. Dec. 2013, pp. 772-778.
Hiramatsu et al., "The role of the SWI/SNF chromatin remodeling complex in maintaining the stemness of glioma initiating cells." Sci. Rep., vol. 7, Article No. 889 (2017).
Ho et al., "An embryonic stem cell chromatin remodeling complex, esBAF, is essential for embryonic stem cell self-renewal and pluripotency." Proc. Natl. Acad. Sci. USA, vol. 106, pp. 5181-5186 (2009).
Ho et al., "esBAF facilitates pluripotency by conditioning the genome for LIF/STAT3 signalling and by regulating polycomb function." Nature Cell Biology, vol. 13, pp. 903-913 (2011).
Hodges et al., "Dominant-negative SMARCA4 mutants alter the accessibility landscape of tissue-unrestricted enhancers." Nat. Struct. Mol. Biol., vol. 25, pp. 61-72 (2018).
Huang et al., "Chromatin-remodelling factor BRG1 selectively activates a subset of interferon-alpha-inducible genes." Nat. Cell Biol., vol. 4, pp. 774-781 (2002).
Huntly et al., "Leukaemia stem cells and the evolution of cancer-stem-cell research." Nat. Rev. Cancer, vol. 5, pp. 311-321 (2005).
Imielinski et al., "Mapping the hallmarks of lung adenocarcinoma with massively parallel sequencing." Cell, vol. 150, pp. 1107-1120 (2012).
International Preliminary Report on Patentability Corresponding to International Application No. PCT/US2020/048396, mailed Mar. 10, 2022, 7 pages.
International Search Report and Written Opinion of the International Searching Authority corresponding to International Application No. PCT/US2020/048396 dated Jan. 22, 2021, 9 pages.
Invitation to Pay Additional Fees Corresponding to International Application No. PCT/US2020/048396, mailed Nov. 10, 2020, 9 pages.
Ito et al., "Gfap and Osmr regulation by BRG1 and STAT3 via interchromosomal gene clustering in astrocytes." Mol. Biol. Cell, vol. 29, pp. 209-219 (2018).
Joo et al., "Patient-specific orthotopic glioblastoma xenograft models recapitulate the histopathology and biology of human glioblastomas in situ." Cell Reports, vol. 3, pp. 260-273 (2013).
Kadoch et al., "Proteomic and bioinformatic analysis of mammalian SWI/SNF complexes identifies extensive roles in human malignancy." Nat. Genet., vol. 45, pp. 592-601 (2013).
Kaeser et al., "BRD7, a novel PBAF-specific SWI/SNF subunit, is required for target gene activation and repression in embryonic stem cells." J. Biol. Chem., vol. 283, pp. 32254-32263 (2008).
Kidder et al., SWI/SNF-Brg1 regulates self-renewal and occupies core pluripotency-related genes in embryonic stem cells. Stem Cells, vol. 27, pp. 317-328 (2009).
Kothandapani et al., "Downregulation of SWI/SNF chromatin remodeling factor subunits modulates cisplatin cytotoxicity." Exp. Cell Res., vol. 318, pp. 1973-1986 (2012).
Kwon et al., "ATM-mediated phosphorylation of the chromatin remodeling enzyme BRG1 modulates DNA double-strand break repair." Oncogene, vol. 34, pp. 351-361 (2015).
Le Loarer et al., "SMARCA4 inactivation defines a group of undifferentiated thoracic malignancies transcriptionally related to BAF-deficient sarcomas." Nat. Genet., vol. 47, pp. 1200-1205 (2015).
Lee, S.Y.., "Temozolomide resistance in glioblastoma multiforme." Genes & Diseases, vol. 3, Issue. 3, May 11, 2016, pp. 198-210.
Love et al., "The genetic landscape of mutations in Burkitt lymphoma." Nat. Genet., vol. 44, 1321-1325 (2012).
Malta et al., "Machine Learning Identifies Stemness Features Associated with Oncogenic Dedifferentiation." Cell, vol. 173, pp. 338-354, Article ID e315 (2018).
Mangiola et al., "Stem cell marker nestin and c-Jun NH2-terminal kinases in tumor and peritumor areas of glioblastoma multiforme: possible prognostic implications." Clin. Cancer Res., vol. 13, pp. 6970-6977 (2007).
Mani et al., "The epithelial-mesenchymal transition generates cells with properties of stem cells." Cell, vol. 133, pp. 704-715 (2008).
Marotta et al., "Cancer stem cells: a model in the making." Current Opinion in Genetics & Development, vol. 19, pp. 44-50 (2009).
Megeney et al., "bFGF and LIF signaling activates STAT3 in proliferating myoblasts." Dev. Genet., vol. 19, pp. 139-145 (1996).
Ni et al., "Brahma-related gene 1-dependent STAT3 recruitment at IL-6-inducible genes." J. Immunol., vol. 178, pp. 345-351 (2007).
Park et al., "Mammalian SWI/SNF complexes facilitate DNA double-strand break repair by promoting gamma-H2AX induction." EMBO J., vol. 25, pp. 3986-3997 (2006).
Patel et al., "Single-cell RNA-seq highlights intratumoral heterogeneity in primary glioblastoma." Science, vol. 344, pp. 1396-1401 (2014).
Pfeffer et al., "STAT3 as an adapter to couple phosphatidylinositol-3 kinase to the IFNAR1 chain of the type I interferon receptor." Science, vol. 276, pp. 1418-1420 (1997).
Pfeffer et al., "Unphosphorylated STAT3 regulates the antiproliferative, antiviral, and gene-inducing actions of type I interferons." Biochem. Biophys. Res. Commun., vol. 490, pp. 739-745 (2017).
Pollard et al., "Glioma stem cell lines expanded in adherent culture have tumor-specific phenotypes and are suitable for chemical and genetic screens." Cell Stem Cell, vol. 4, pp. 568-580 (2009).
Pubchem CID 138466862, , Schembl20811926, Jul. 20, 2019, Date Accessed Dec. 29, 2020, 7 pages.
Qi et al., "BRG1 promotes the repair of DNA double-strand breaks by facilitating the replacement of RPA with RAD51." J. Cell Sci., vol. 128, pp. 317-330 (2015).
Saikali et al., "Expression of nine tumour antigens in a series of human glioblastoma multiforme: interest of EGFRvIII, IL-13Ralpha2, gp100, and TRP-2 for immunotherapy." Journal of Neuro-oncology, vol. 81, pp. 139-148 (2007).
Sanai et al., "Neural stem cells and the origin of gliomas." N. Engl. J. Med., vol. 353, pp. 811-822 (2005).
Sausville et al., "Contributions of human tumor xenografts to anticancer drug development." Cancer Res., vol. 66, pp. 3351-3354 (2006).

(56) References Cited

OTHER PUBLICATIONS

Sentani et al., "Increased expression but not genetic alteration of BRG1, a component of the SWI/SNF complex, is associated with the advanced stage of human gastric carcinomas." Pathobiology, vol. 69, pp. 315-320 (2001).
Shain et al., "The spectrum of SWI/SNF mutations, ubiquitous in human cancers." PLoS One, vol. 8, Article ID e55119 (2013).
Singhal et al., "Chromatin-Remodeling Components of the BAF Complex Facilitate Reprogramming." Cell, vol. 141, pp. 943-955 (2010).
Souma et al., "Antiproliferative effect of SOCS-1 through the suppression of STAT3 and p38 MAPK activation in gastric cancer cells." Int. J. Cancer, vol. 131, pp. 1287-1296 (2012).
Strobeck et al., "BRG-1 is required for RB-mediated cell cycle arrest." Proc. Natl. Acad. Sci. USA, vol. 97, pp. 7748-7753 (2000).
Sun et al., "Aberrant expression of SWI/SNF catalytic subunits BRG1/BRM is associated with tumor development and increased invasiveness in prostate cancers." The Prostate, vol. 67, pp. 203-213 (2007).
Surawicz et al., "Brain tumor survival: results from the National Cancer Data Base." Journal of Neuro-oncology, vol. 40, pp. 151-160 (1998).
Taillandier et al., "Models for neuro-oncological preclinical studies: solid orthotopic and heterotopic grafts of human gliomas into nude mice." Journal of Neuroscience Methods, vol. 125, pp. 147-157 (2003).
The Cancer Genome Atlas (TCGA) Research Network, "Comprehensive genomic characterization defines human glioblastoma genes and core pathways." Nature, vol. 455, pp. 1061-1068 (2008).
Tolstorukov et al., "Swi/Snf chromatin remodeling/tumor suppressor complex establishes nucleosome occupancy at target promoters." Proc. Natl. Acad. Sci. USA, vol. 110, pp. 10165-10170 (2013).
Trotter et al., "The BRG1 transcriptional coregulator." Nucl. Recept. Signal., vol. 6, Article ID e004 (2008).
Taspinar, et al., "Effect of lomeguatrib-temozolomide combination on MGMT promoter methylation and expression in primary glioblastoma tumor cells," Tumor Biol. (2013) 34: pp. 1935-1947.
Turkson et al., "STAT proteins: novel molecular targets for cancer drug discovery." Oncogene, vol. 19, pp. 6613-6626 (2000).
Vangamudi et al., "The SMARCA2/4 ATPase Domain Surpasses the Bromodomain as a Drug Target in SWI/SNF- Mutant Cancers: Insights from cDNA Rescue and PFI-3 Inhibitor Studies." Cancer Res., vol. 75, pp. 3865-3878 (2015).
Verhaak et al., "Integrated genomic analysis identifies clinically relevant subtypes of glioblastoma characterized by abnormalities in PDGFRA, IDH1, EGFR, and NF1." Cancer Cell, vol. 17, pp. 98-110 (2010).
Witkowski et al., "Germline and somatic SMARCA4 mutations characterize small cell carcinoma of the ovary, hypercalcemic type." Nat. Genet., vol. 46, pp. 438-443 (2014).
Wong et al., "Structural alterations of the epidermal growth factor receptor gene in human gliomas." Proc. Natl. Acad. Sci. USA, vol. 89, pp. 2965-2969 (1992).
Yang et al., "Direct association of STAT3 with the IFNAR1 chain of the human type I IFN receptor." J. Biol. Chem., vol. 271, pp. 8057-8061 (1996).
Yang et al., "Identification of CXCL 11 as a STAT3-dependent gene induced by IFN." J. Immunol., vol. 178, pp. 986-992 (2007).
Yang et al., "IFN induces miR-21 through a signal transducer and activator of transcription 3-dependent pathway as a suppressive negative feedback on IFN-induced apoptosis." Cancer Res., vol. 70, pp. 8108-8116 (2010).
Yang et al., "MicroRNA miR-21 regulates the metastatic behavior of B16 melanoma cells." J. Biol. Chem., vol. 286, pp. 39172-39178 (2011).
Yang et al., "STAT3 complements defects in an interferon resistant cell line: Evidence for an essential role for STAT3 in interferon signaling and biological activities." Proc. Natl. Acad. Sci. USA, vol. 95, pp. 5568-5572 (1998).
Yang, C.H., et al., "Interferon Alpha Activates NF-kappab in JAK1-deficient Cells Through a TYK2-dependent Pathway," Journal of Biological Chemistry, vol. 280, Issue. 27, Jul. 8, 2005, pp. 25849-25853.
Zhang et al., "Transcriptional repression by the BRG1-SWI/SNF complex affects the pluripotency of human embryonic stem cells." Stem Cell Reports, vol. 3, pp. 460-474 (2014).
Zhong et al., "Stat3: a STAT family member activated by tyrosine phosphorylation in response to epidermal growth factor and interleukin-6." Science, vol. 264, pp. 95-98 (1994).

* cited by examiner

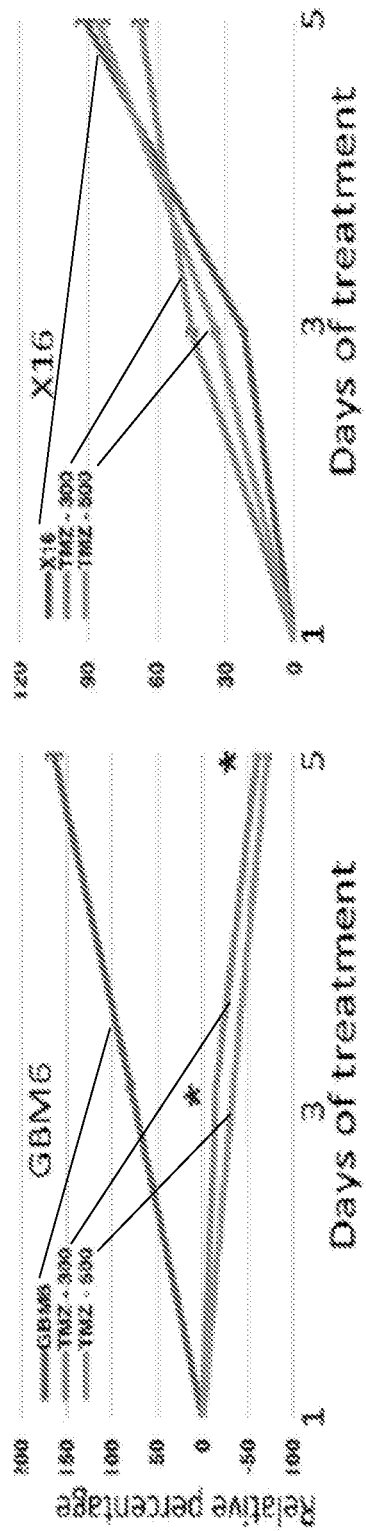
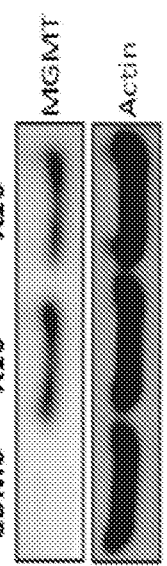
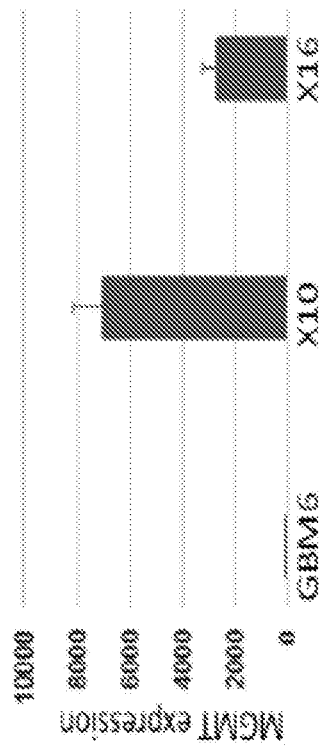
FIG. 1A
FIG. 1B
FIG. 1C

BROMODOMAIN INHIBITORS TO TARGET THERAPY-RESISTANT CANCER

CROSS-REFERENCE TO RELATED APPLICATIONS

This application claims benefit of U.S. Provisional Patent Application Ser. No. 62/893,667, filed Aug. 29, 2019, which is herein incorporated by reference in its entirety.

TECHNICAL FIELD

The presently disclosed subject matter relates to novel inhibitors of the Brahma-related gene-1 (BRG1) bromodomain and to methods of using BRG1 bromodomain inhibitors (BRIs) to treat cancer, particularly therapy-resistant glioblastoma. For example, in some embodiments, the presently disclosed subject matter relates to methods of treating glioblastoma comprising administering a BRI and a chemotherapeutic agent, such as a DNA alkylating agent to a subject in need of treatment for glioblastoma.

ABBREVIATIONS

%=percentage
° C.=degrees Celsius
µM=micromolar
BRI=BRG1 bromodomain inhibitor
BRG1=Brahma-related gene-1
BTIC=brain-tumor-initiating cells
DCM=dichloromethane
DMSO=dimethyl sulfoxide
EFGR=epidermal growth factor receptor
ESC=embryonic stem cell
ESI=electrospray ionization
g or gm=grams
GBM=glioblastoma
HPLC=high performance liquid chromatography
HRMS=high resolution mass spectrometry
IFN=interferon
kg=kilogram
mg=milligram
MGMT=$O^6$-methylguanine methyltransferase
mL=milliliter
mol=mole
nm=nanometer
NMR=nuclear magnetic resonance
PA=PFI-3 analog
PDX=patient-derived xenograft
PFI-3=(E)-1-(2-hydroxyphenyl)-3-((1R,4R)-5-(pyridine-2-yl)-2,5-diazabicyclo[2.2.1]heptan-2-yl)prop-2-en-1-one
TLC=thin layer chromatography
TMZ=temozolomide

BACKGROUND

Glioblastoma (GBM) is the most common malignant primary adult brain tumor. Due to its highly aggressive nature, it is also among the most devastating cancers. After standard of care therapy, the overall median survival for GBM patients is only about 6 months, with a 5-year survival rate of less than 10%. It is believed that a small population of brain tumor-initiating cells (BTICs) which exist within the tumor responsible for the aggressive nature of GBM, as well as its resistance to current treatments and high tumor recurrence.

Accordingly, there is an ongoing need for identifying new therapies and molecular targets in the treatment of GBM, particularly for the development of new therapeutic strategies for targeting BTICs in GBM.

SUMMARY

In some embodiments, the presently disclosed subject matter provides a compound having the structure of Formula (I):

(I)

wherein: ====== represents a single or double bond; Ar is selected from cycloalkyl, substituted cycloalkyl, aryl, substituted aryl, heteroaryl, and substituted heteroaryl; R is H, halo, amino, thiol, or hydroxy and Y is H or halo or where R and Y together form a group selected from —N=CH—NH—, —N=N—NH—, and —CH=N—NH—; $R_1$ and $R_2$ are each independently selected from the group comprising H, cyano, halo, alkyl, substituted alkyl, perhaloalkyl, alkoxy, cycloalkyl, substituted cycloalkyl, cycloalkenyl, and substituted cycloalkenyl; $R_3$, $R_4$ and $R_5$ are each H; and X is O, S, or NH; or wherein (i) X and $R_5$ together comprise —N—NH— and/or wherein $R_3$ and $R_4$ together form an alkylene group, optionally ethylene or (ii) $R_3$ and $R_5$ together form a covalent bond or methylene group; or a pharmaceutically acceptable salt thereof, subject to the proviso that the compound is not PFI-3. In some embodiments, Ar is selected phenyl or pyridinyl, optionally substituted with one or more aryl group substituents, further optionally wherein the one or more aryl group substituents are selected from halo, alkoxy, and cyano.

In some embodiments, the compound of Formula (I) has a structure of Formula (II):

(II)

wherein ====== R, Y, X, and $R_1$-$R_5$ are as defined for the compound of Formula (I) and wherein $X_1$ is CH, C($R_7$), or N; n is an integer from 0 to 4; and each $R_6$ and $R_7$ is independently selected from cyano, halo, amino, alkyl, substituted alkyl, hydroxy, alkoxy, and perhaloalkyl; or a pharmaceutically acceptable salt thereof. In some embodiments, n is 0, 1, or 2 and each $R_6$ is independently selected from fluoro, chloro, methoxy, and cyano.

In some embodiments, X is O, $X_1$ is N and R and Y together form a group selected from —N=CH—NH—, —N═N—NH—, and —CH═N—NH—. In some embodiments, X and R$_5$ together comprise —N—NH, optionally wherein R is OH and R$_2$ is H, fluoro, chloro, or bromo.

In some embodiments, X is O, R is OH, and R$_2$ is selected from H, fluoro, chloro, and bromo, optionally wherein R$_2$ is fluoro or bromo. In some embodiments, R$_3$ and R$_4$ together form an ethylene group.

In some embodiments, the compound of Formula (II) has a structure of Formula (III):

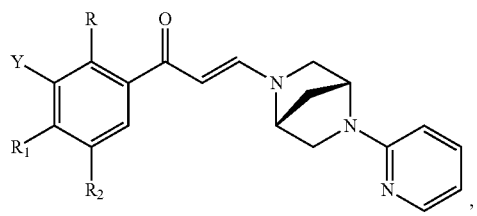

(III)

wherein: R is selected from H, hydroxy and halo; Y is H or halo; and R$_1$ and R$_2$ are independently selected from H, cyano and halo, subject to the proviso that when R is hydroxy, Y is halo and/or at least one of R$_1$ and R$_2$ is cyano or halo; or a pharmaceutically acceptable salt thereof. In some embodiments, one of R, R$_1$, and R$_2$ is selected from fluoro, chloro, and bromo. In some embodiments, the compound of Formula (III) is selected from:

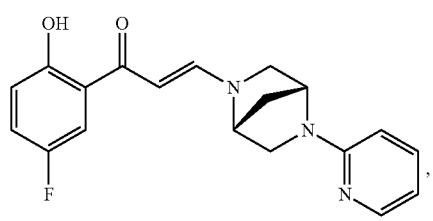,

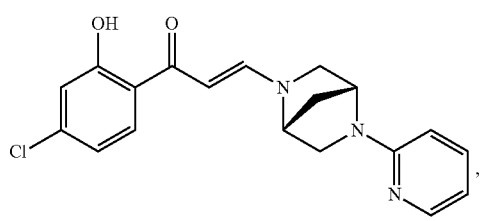,

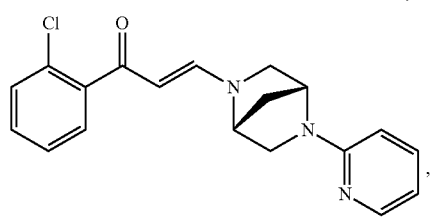,

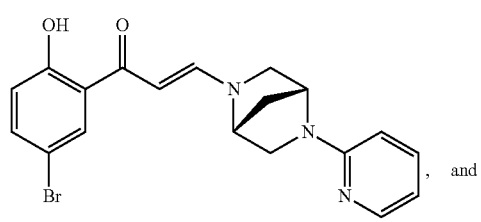, and

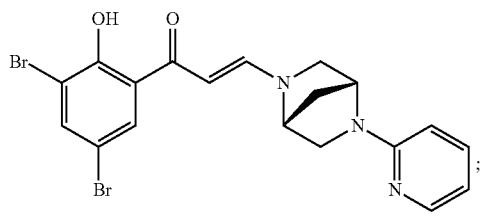;

or a pharmaceutically acceptable salt thereof.

In some embodiments, the compound is selected from the group comprising:

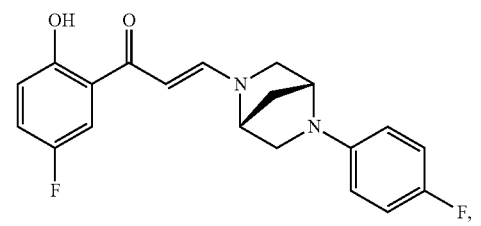,

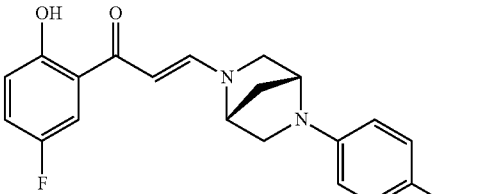,

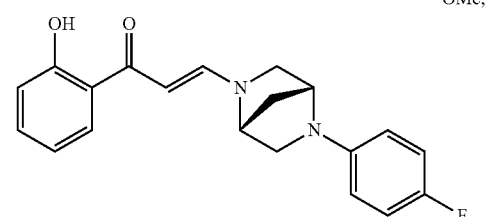,

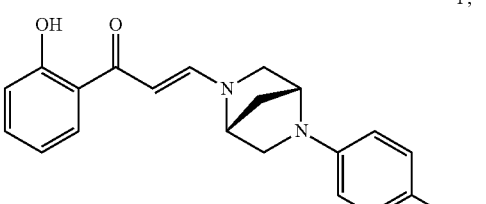,

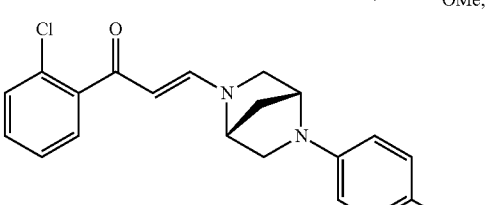,

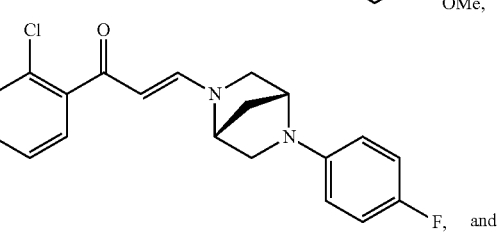,
and

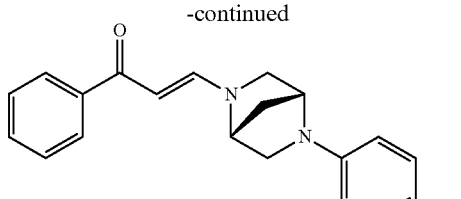

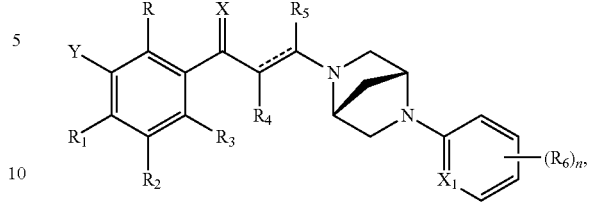

wherein ===== R, Y, X, and R₁-R₅ are as defined for the compound of Formula (I) and wherein X₁ is CH, C(R₇), or N; n is an integer from 0 to 4; and each R₆ and R₇ is independently selected from cyano, halo, amino, alkyl, substituted alkyl, hydroxy, alkoxy, and perhaloalkyl; or a pharmaceutically acceptable salt thereof. In some embodiments, n is 0, 1, or 2 and each R₆ is independently selected from fluoro, chloro, methoxy, and cyano.

In some embodiments, X is O, X₁ is N, and R and Y together form a group selected from —N=CH—NH—, —N=N—NH—, and —CH=N—NH—. In some embodiments, X and R₅ together comprise —N—NH, optionally wherein R is OH and R₂ is H, fluoro, chloro, or bromo.

In some embodiments, X is O, R is OH, and R₂ is selected from H, fluoro, chloro, and bromo, optionally wherein R₂ is fluoro or bromo. In some embodiments, R₃ and R₄ together form an ethylene group.

In some embodiments, the compound of Formula (II) has a structure of Formula (III):

In some embodiments, the presently disclosed subject matter provides a pharmaceutical formulation comprising a pharmaceutically acceptable carrier and a compound having a structure of Formula (I), subject to the proviso that the compound is not PFI-3.

In some embodiments, the presently disclosed subject matter provides a method of treating glioblastoma in a subject in need thereof, the method comprising: (a) administering to the subject a compound of Formula (I):

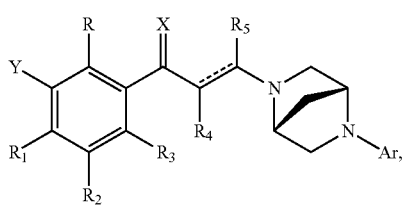

wherein: ===== represents a single or double bond; Ar is selected from cycloalkyl, substituted cycloalkyl, aryl, substituted aryl, heteroaryl, and substituted heteroaryl; R is H, halo, amino, thiol, or hydroxy and Y is H or halo or where R and Y together form a group selected from —N=CH—NH—, —N=N—NH—, and —CH=N—NH—; R₁ and R₂ are each independently selected from the group comprising H, cyano, halo, alkyl, substituted alkyl, perhaloalkyl, alkoxy, cycloalkyl, substituted cycloalkyl, cycloalkenyl, and substituted cycloalkenyl; R₃, R₄ and R₅ are each H; and X is O, S, or NH; or wherein (i) X and R₅ together comprise —N—NH— and/or R₃ and R₄ together form an alkylene group, optionally ethylene or (ii) R₃ and R₅ together form a covalent bond or methylene group; or a pharmaceutically acceptable salt thereof, and optionally wherein the compound of Formula (I) is not PFI-3; and (b) administering to the subject a chemotherapeutic compound, wherein said chemotherapeutic compound is a DNA alkylating agent.

In some embodiments, the DNA alkylating agent is temozolomide (TMZ) or carmustine. In some embodiments, Ar is selected phenyl or pyridinyl, optionally substituted with one or more aryl group substituents, further optionally wherein the one or more aryl group substituents are selected from halo, alkoxy, and cyano.

In some embodiments, the compound of Formula (I) has a structure of Formula (II):

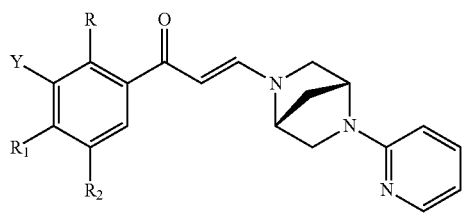

wherein: R is selected from H, hydroxy and halo; Y is H or halo; and R₁ and R₂ are independently selected from H, cyano and halo, optionally wherein when R is hydroxy, Y is halo and/or at least one of R₁ and R₂ is cyano or halo; or a pharmaceutically acceptable salt thereof. In some embodiments, one of R, R₁, and R₂ is selected from fluoro, chloro and bromo. In some embodiments, the compound of Formula (III) is selected from:

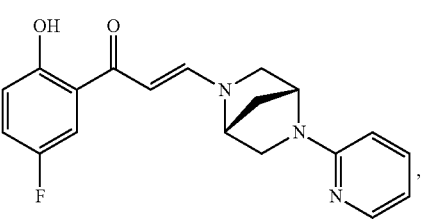

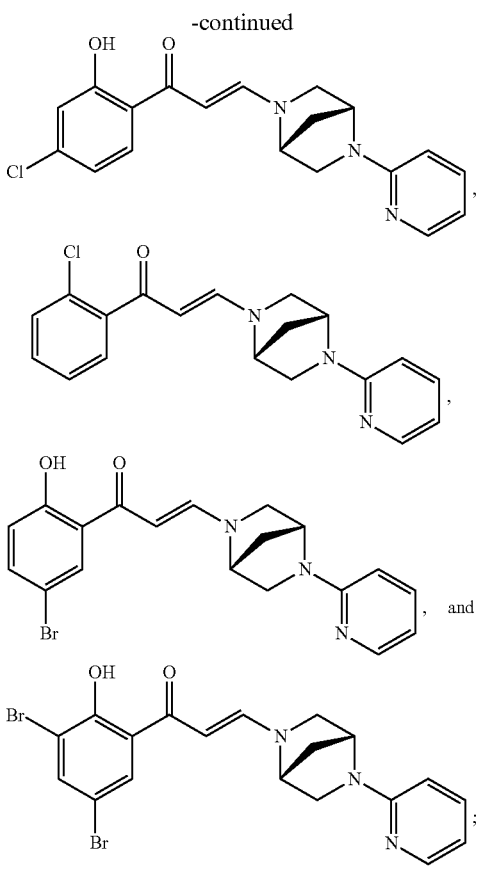

or a pharmaceutically acceptable salt thereof.

In some embodiments, the compound of Formula (I) is PFI-3:

In some embodiments, the glioblastoma is a DNA alkylating agent-resistant glioblastoma.

In some embodiments, the presently disclosed subject matter provides a method of inhibiting Brahma-related gene 1 (BRG1) bromodomain, the method comprising contacting a sample comprising BRG1 with a compound of Formula (I), subject to the proviso that the compound is not PFI-3.

Accordingly, it is an object of the presently disclosed subject matter to provide compounds of Formula (I), related pharmaceutical formulations and methods of treating glioblastoma and inhibiting BRG1 bromodomain.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

FIG. 1A is a pair of graphs showing the effect of temozolomide (TMZ) on the proliferation of brain-tumor initiating cells (BTICs) obtained from two independent glioblastoma tumors, GBM6 (left) and X16 (right). Relative proliferation is shown for cells treated with 300 micromolar (μM) TMZ or 600 μM TMZ, as well as for untreated cells. *p≤0.05.

FIG. 1B is a graph showing $O^6$-methylguanine methyltransferase (MGMT) expression in total RNA samples prepared from three independent glioblastoma tumors, GBM6, X10, and X16. MGMT expression was determined by quantitative polymerase chain reaction (qPCR).

FIG. 1C is an immunoblot image of protein lysates from three independent glioblastoma tumors, GBM6, X10, and X16, immunoblotted for $O^6$-methylguanine methyltransferase (MGMT, top) and actin (bottom).

DETAILED DESCRIPTION

Figure 1D:
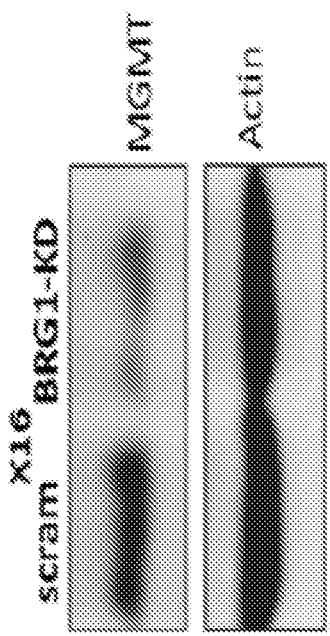
FIG. 1D is a graph showing cell proliferation in control and Brahma-related gene-1-knock-down (BRG1-KD) brain-tumor initiating cells (BTICs) from the X16 glioblastoma described in FIGS. 1A-1C. The BRG1-KD BTICs were treated with 500 micromolar (μM) temozolomide (TMZ). *p≤0.05.

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

Unless otherwise indicated, all numbers expressing quantities of time, temperature, concentration, mass, percentage (%), and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In some embodiments, "lower alkyl" can refer to $C_{1-6}$ or $C_{1-5}$ alkyl groups. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, cyano, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, cyano, amino, alkylamino, dialkylamino, ester, acyl, amide, sulfonyl, sulfate, and mercapto.

The term "alkenyl" refers to an alkyl group as defined above including at least one carbon-carbon double bond. Exemplary alkenyl groups include, but are not limited to, ethenyl, propenyl, butenyl, pentenyl, hexenyl, octenyl, butadienyl, and allenyl groups. Alkenyl groups can optionally be substituted with one or more alkyl group substituents, which can be the same or different, including, but not limited to alkyl (saturated or unsaturated), substituted alkyl (e.g., halo-substituted and perhalo-substituted alkyl, such as but not limited to, —$CF_3$), cycloalkyl, halo, nitro, hydroxyl, carbonyl, carboxyl, acyl, alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. In some embodiments, the cycloalkyl ring system comprises between 3 and 6 carbon atoms. The cycloalkyl group can be optionally partially unsaturated. The cycloalkyl group also can be optionally substituted with an alkyl group substituent as defined herein. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include, but are not limited to, cyclopropyl, cyclobutyl, cyclopentyl, cyclohexyl, cycloheptyl, and the like. Further, the cycloalkyl group can be optionally substituted with a linking group, such as an alkylene group as defined hereinabove, for example, methylene, ethylene, propylene, and the like. In such cases, the cycloalkyl group can be referred to as, for example, cyclopropylmethyl, cyclobutylmethyl, and the like. Additionally, multicyclic cycloalkyl rings include adamantyl, octahydronaphthyl, decalin, camphor, camphane, and noradamantyl.

The term "cycloalkenyl" refers to a cycloalkyl group including at least one carbon-carbon double bond. Exemplary cycloalkenyl groups include cyclopropenyl, cyclobutenyl, cyclopentenyl, and cyclohexenyl. The cycloalkenyl can be optionally substituted with one or more alkyl group substituents.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds (i.e., "heteroaryl"). The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyridine, imidazole, benzimidazole, isothiazole, isoxazole, pyrazole, pyrazine, triazine, pyrimidine, quinoline, isoquinoline, indole, carbazole, napthyl, and the like.

"Heterocyclic", "heterocycle", or "heterocyclo" as used herein alone or as part of another group, refers to an aliphatic (e.g., fully or partially saturated heterocyclo) or aromatic (e.g., heteroaryl) monocyclic- or a bicyclic-ring system comprising one or more heteroatoms (e.g., 1, 2, or 3 heteroatoms selected from oxygen, sulfur, and substituted or unsubstituted nitrogen) inserted along the cyclic alkyl or aryl carbon chain. Monocyclic ring systems are exemplified by any 5- or 6-membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, ethylene oxide, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydropyran, tetrahydrothiophene (also known as thiolane), tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, carbazole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and can be optionally substituted with one or more alkyl and/or aryl group substituents.

The term "heteroaryl" refers to aromatic mono- or multicyclic ring systems comprising one or more heteroatoms (e.g., 1, 2, 3, 4, or more N, S, O, or Se atoms) inserted in place of one or more carbon atoms in a ring. The heteroaryl group can be optionally substituted with one or more aryl group substituents. Representative heteroaryl groups include, but are not limited to, furan, oxazole, isoxazole, pyrazine, pyrazole, pyridine, pyrimidine, pyridazine, pyrrole, thiazole, thiophene, triazine, benzofuran, benzimidazole, benzothiazole, benzothiophene, benzoxadiazole, benzoxazole, benzofuran, cinnoline, indazole, indole, isobenzofuran, isoindole, isoquinoline, purine, quinoline, quinoxaline, acridine, and phthalazine.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

As used herein, the term "acyl" refers to an organic carboxylic acid group wherein the —OH of the carboxylic acid group has been replaced with another substituent. Thus, an acyl group can be represented by RC(═O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl.

"Alkoxyl" refers to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The terms "oxyalkyl" and "alkoxy" can be used interchangably with "alkoxyl".

"Aralkyl" refers to an aryl-alkyl- or an -alkyl-aryl group wherein aryl and alkyl are as previously described and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

The term "carbonyl" refers to the group —C(═O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "carboxyl" refers to the —C(═O)OH or —C(═O)O$^-$ group.

The term "acid chloride" can refer to the —C(═O)Cl group.

The terms "halo" or "halogen" as used herein refer to fluoro, chloro, bromo, and iodo groups.

The term "perhaloalkyl" refers to an alkyl group as defined herein wherein each hydrogen atom is replaced by a halo group. The term "perfluoralkyl" refers to an alkyl group as defined herein wherein each hydrogen atom is replaced by a fluoro group. Exemplary perfluoralkyl groups include perfluoromethyl (i.e., —CF$_3$), perfluoroethyl (i.e., —CF$_2$CF$_3$), and perfluoropropyl (e.g., —CF$_2$CF$_2$CF$_3$).

A structure represented generally by a formula such as:

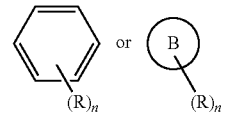

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

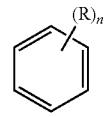

wherein n is an integer from 0 to 2 comprises compound groups including, but not limited to:

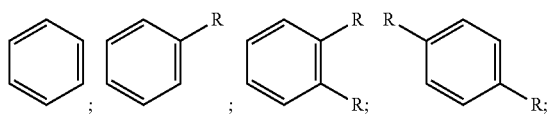

and the like.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

When two substituent R groups are defined as together forming a covalent bond, the named R groups are replaced by a direct bond between the atoms to which the two named R groups are attached.

The term "amine" refers to a molecule having the formula $N(R)_3$, or a protonated form thereof, wherein each R is independently H, alkyl, substituted alkyl, aryl, substituted aryl, aralkyl, substituted aralkyl, or wherein two R groups together form an alkylene or arylene group. The term "primary amine" refers to an amine wherein at least two R groups are H. The term "secondary amine" refers to an amine wherein only one R group is H. The term "alkylamine" can refer to an amine wherein two R groups are H and the other R group is alkyl or substituted alkyl. "Dialkylamine" can refer to an amine where two R groups are alkyl. "Arylamine" can refer to an amine wherein one R group is aryl. Amines can also be protonated, i.e., have the formula $[NH(R)_3]^+$.

The term "amino" refers to the group —$N(R)_2$ wherein each R is independently H, alkyl, substituted alkyl, aryl, substituted aryl, aralkyl, or substituted aralkyl. In some embodiments, "amino" refers to —$NH_2$. The terms "aminoalkyl" and "alkylamino" can refer to the group —$N(R)_2$ wherein each R is H, alkyl or substituted alkyl, and wherein at least one R is alkyl or substituted alkyl.

The term "cyano" refers to —C≡N the group.

The terms "hydroxyl" and "hydroxy" refer to the —OH group.

The terms "mercapto" and "thiol" refer to the —SH group.

The term "oxo" refers to a compound described previously herein wherein a carbon atom is replaced by an oxygen atom.

The term "nitro" refers to the —$NO_2$ group.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "R'," "X," "Y," "Y", "A," "A", "B," "L," or "Z" group will generally have the structure that is recognized in the art as corresponding to a group having that name, unless specified otherwise herein. For the purposes of illustration, certain representative "R," "X," and "Y" groups as set forth above are defined below. These definitions are intended to supplement and illustrate, not preclude, the definitions that would be apparent to one of ordinary skill in the art upon review of the present disclosure.

The terms "treatment" and "treating" and the like as used herein refers to any treatment of a disease and/or condition in an animal or mammal, particularly a human, and includes: (i) preventing a disease, disorder and/or condition from occurring in a person which can be predisposed to the disease, disorder and/or condition, or at risk for being exposed to an agent that can cause the disease, disorder, and/or condition; but, has not yet been diagnosed as having it; (ii) inhibiting the disease, disorder and/or condition, i.e., arresting its development; and (iii) relieving the disease, disorder and/or condition, i.e., causing regression of the disease, disorder and/or condition.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, Protective Groups in Organic Synthesis, 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, acetyl (Ac), benzoyl (Bn), and trimethylsilyl (TMS), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like.

The term "small molecule" refers to a compound having a molecular weight of less than about 900 daltons. In some embodiments, the molecular weight is less than about 850 daltons, less than about 800 daltons, less than about 750 daltons, less than about 700 daltons, less than about 650 daltons, less than about 600 daltons, or less than about 550 daltons.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). Traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

The term "DNA alkylating agent" as used herein refers to a chemotherapeutic agent that acts by adding an alkyl group to guanine in DNA, thereby leading to breakage of the DNA and lack of cell proliferation. DNA alkylating agents generally belong to one of five different classes: nitrogen mustards (e.g., bendamustine, chlorambucil, cyclophosphamide, ifosfamide, mechlorethamine, melphalan, chlormethine, and uramustine); nitrosoureas (e.g., carmustine, lomustine, and streptozocin); alkylsulfonates (e.g., busulfan); triazines (e.g., dacarbazine, temozolomide (TMZ), and mitozolomide); and ethylenimines (e.g., altretamine and thiotepa). In some embodiments, the DNA alkylating agent can also be a platinum based agent (e.g., cisplatin, carboplatin, oxaliplatin, etc.), which does not add an alkyl group to DNA, but which can coordinate to DNA, thereby interfering with DNA repair.

II. General Considerations

Gliomas are the most common primary intracranial neoplasms in adults and a leading cause of cancer-related morbidity and mortality in the United States.[1,2] Grade IV glioma or GBM is the most aggressive and deadliest brain cancer, and accounts for nearly 75% of all gliomas. The primary treatment of GBM is surgical resection combined with adjuvant chemotherapy and radiation therapy, which results in overall median survival of about 15 months. The 5-year overall prognosis of GBM patients is dismal (<10% survival) and has remained relatively unchanged for decades.[1]

Gene expression profiles of samples in The Cancer Genome Atlas (TCGA) database have identified three general GBM molecular subtypes: Proneural, Classical and Mesenchymal.[3] However, single cell analysis shows that multiple molecular subtypes exist within a GBM tumor and gene expression profiles can even vary dramatically across individual cells within the tumor,[4] illustrating that individual GBM tumors are highly heterogenous. Dysregulation of the epidermal growth factor receptor (EFGR) is found in about 50% of GBM patient samples analyzed.[5,6] The EGFR variant III (EGFRVIII), formed by deletion of exons 2-7, is the most common EGFR variant in GBM and results in a constitutively-active kinase.[7,8] As tumor heterogeneity is an important factor to be considered in GBM therapy, a panel of different patient-derived GBM cell models has been established that have been extensively characterized through cell signaling and gene expression analysis.[2,9-11] Thus, in the studies described below, GBM patient-derived xenografts (PDXs) that represent different EGFR subtypes (X10 and X16 express wild-type EGFR, and GBM6 expresses mutant EGFRvIII) were used.

The highly aggressive nature of GBM as well as its heterogeneity at the cellular level have been attributed to a subpopulation of brain tumor-initiating cells (BTICs).[12-14] BTICs share features of neural stem cells including the expression of Nestin and Sox2,[15,16] the ability to migrate within the brain,[17] and the capacity to self-renew and undergo differentiation.[18] Their high tumor-initiating capacity and therapeutic resistance is believed to drive tumorigenesis and tumor recurrence after therapy.[19] BTICs grown in poly-lysine/laminin-coated flasks display neural stem cell markers and initiate GBM following xenotransplantation.[20] Although adherent glioma cell lines grown in vitro in the presence of serum and the xenografts of these same cell lines in vivo were the mainstays in brain cancer research for decades, they do not recapitulate the genomic and phenotypic properties of the original tumor.[21,22] To overcome these issues PDXs derived from fresh surgical samples that are maintained as xenografts in immunocompromised mice and recapitulate the heterogeneity of GBM have been used.[10,23] It has been found that these BTICs, when injected into the flanks or brains of immunocompromised mice, have markedly enhanced tumor-initiating activity and form tumors that display histological and genomic features of the original GBM PDX.[2,11,20]

It is useful to define the pathways that are selectively activated in BTICs with the purpose to pharmacologically target them. Preclinical data have shown that small molecules hold therapeutic promise for GBM treatment by targeting multiple pathways essential for maintaining GBM stemness.[24] The efforts to sequence the human genome found that chromatin regulation and epigenetic centered processes were tightly linked to cancer, and more than 20% of human cancers bear one or more mutations in the mammalian ATP-dependent chromatin remodeling SWI/SNF complex. The SWI/SNF complex is an evolutionary conserved multi-subunit complex that is critical for gene regulation, differentiation, DNA repair and development. The two mutually exclusive catalytic subunits, BRM (Brahma and SMARCA2) and BRG1 (Brahma-related gene 1 and SMARCA4), provide energy from ATP hydrolysis that is required to reposition and/or remodel nucleosomes at targeted loci, and to open or close chromatin and regulate gene transcription.[25,26] The importance of BRG1 in embryonic development was elucidated by finding that its knockout in mice was embryonically lethal at the peri-implantation stage.[27] BRG1 promotes pluripotency of both mouse and human embryonic stem cells (ESCs), and targeted BRG1 knockdown induces cell differentiation.[27,28] The SWI/SNF or BAF complex in ESCs has a unique composition, and expression of BAF complex components in fibroblasts promotes reversal to a pluripotent state.[28,29] Furthermore, the SWI/SNF complex enhances the efficiency of the ESC pluripotency genes, Oct4, Sox2, KLF4 and c-Myc.[30] Interestingly, BRG1 is the sole catalytic subunit in the SWI/SNF complex found in ESCs.[31-33] BRG1 binds to the promoters of various pluripotency specific genes such as Oct4, Nanog, and the polycomb group (PcG) of genes.[28] BRG1 has been found to have tumor suppressing[34,35] and tumor promoting activity[36,37] in a highly cancer-context specific manner. BRG1 functions as a major tumor suppressor with silencing or loss-of-function mutations enriched in cancers of the lung, ovaries, skin and lymphoma.[35,38-41] However, BRG1 mutations are relatively rare in GBM,[42] and BRG1 is overexpressed in glioma as compared to adjacent normal brain tissue.[43] High BRG1 expression has been associated with poor prognosis and more aggressive tumors in several cancers using TCGA and other databases.[44] High BRG1 expression is also associated with the poor prognosis of glioma patients. Although core and regulatory SWI/SNF subunits reportedly regulate BTIC stemness,[45] it was recently demonstrated that the BRG1 subunit of the human SWI/SNF complex appears to be needed to maintain the stem cell-like identity of BTICs.[2] Using targeted microarrays, it was shown that BRG1 selectively regulates gene expression in BTICs, including glycolytic and glucose transport genes.[2] It was also found that BRG1 loss led to upregulation of the STAT3 signaling pathway, and downregulation of interferon (IFN) response genes.[2]

The BRG1 subunit contains a bromodomain, which is an evolutionarily conserved protein-protein interaction module that binds acetyl-lysine on protein and histone tails.[46] The bromodomain contributes to assembly or targeting of the SWI/SNF complex to specific genomic loci, and the complex plays a critical role in ESC maintenance.[47] The ability of small molecule BRG1 bromodomain inhibitors (BRIs) to partially reverse BTIC stemness has been investigated. For example, PFI-3 is a lead BRI that inhibits the embryonic stem cell phenotype.[47] PFI-3 was found not to inhibit the proliferation or tumorgenicity of a panel of cancer cell lines (lung, synovial sarcoma, leukemia, and rhabdoid tumor cells), and thus, previously, the ATPase domain of BRG1 was considered as a more important druggable anticancer target.[48] However, it has recently been found that, although PFI-3 alone has little effect on BTIC proliferation, PFI-3 inhibits the stemness of BTICs and sensitizes BTICs to DNA alkylating agents in vitro.[2] As described further hereinbelow, compounds that reflect chemical modification of the PFI-3 structure show enhanced anticancer efficacy in subcutaneous BTIC xenografts when combined with TMZ when compared to PFI-3. Taken together, these studies suggest that BRG1 can act as a novel, druggable target in GBM. BRG1 regulates DNA double strand break repair by a mechanism that appears to be independent of the chromatin remodeler's enzymatic or transcriptional activity.[49] Thus, without being bound to any one theory, it appears possible that the repair of DNA breaks induced by DNA alkylating agents like TMZ and Carmustine in BTICs is mediated by the BRG1 bromodomain.

III. BRI Analogs

The structure of PFI-3 is shown below in Scheme 1, below. According to some aspects of the presently disclosed subject matter, analogs of PFI-3 (PAs) are provided. Analogs of PFI-3 can include compounds with modifications at the A, B, and/or C rings of PFI-3, as indicated below in Scheme 1. For example, the A ring can include additional or alternative substituents and/or the C pyridinyl ring can be substituted with one or more aryl group substituents and/or replaced by another aryl group, such as another six membered aryl or heteroaryl group, which can be substituted or unsubstituted. Additional or alternatively modified analogs include compounds where the enone linkage of PFI-3 is modified.

In some embodiments, the presently disclosed analogs provide additional BRIs having potent BRG1 bromodomain inhibition activity to enhance BTIC sensitivity to DNA alkylating agents and to optimize the treatment of cancer, such as resistant glioma. In some embodiments, the analogs provide improved biological activities, e.g., improved BRG1 inhibition, improved BTIC sensitivity enhancement, improved bioavailability, and/or improved metabolic stability compared to PFI-3.

stituted aryl, heteroaryl, and substituted heteroaryl; R is H, halo, amino, thiol, or hydroxy and Y is H or halo or where R and Y together form a group selected from —N=CH—NH—, —N=N—NH—, and —CH=N—NH—; $R_1$ and $R_2$ are each independently selected from the group comprising H, cyano, halo, alkyl, substituted alkyl, perhaloalkyl (e.g., perfluoroalkyl), alkoxy, cycloalkyl, substituted cycloalkyl, cycloalkenyl, and substituted cycloalkenyl; $R_3$, $R_4$ and $R_5$ are each H; and X is O, S, or NH; or wherein (i) X and $R_5$ together comprise —N—NH— and/or $R_3$ and $R_4$ together form an alkylene group, optionally ethylene (thereby forming a fused ring structure with the phenyl group in the structure of Formula (I)) or (ii) $R_3$ and $R_5$ together form a covalent bond (i.e., so that the carbon attached to $R_5$ is directly attached to the carbon attached to $R_3$, thereby forming a five-membered ring) or a methylene group (i.e., thereby forming a six-membered ring); or a pharmaceutically acceptable salt thereof, subject to the proviso that the compound is not PFI-3.

In some embodiments, Ar is a six- or five-membered aryl or heteroaryl group, optionally substituted with one or more aryl group substituents. In some embodiments, Ar is phenyl or a nitrogen-containing heteroaryl, such as pyridinyl, diazinyl, oxazinyl, thiazinyl, or triazinyl. In some embodiments, Ar is phenyl or pyridinyl (e.g., 2-pyridinyl, 3-pyridinyl, or 4-pyridinyl), which can optionally be substituted with one or more aryl group substituents, such as, but not limited to, halo, cyano, amino, alkyl, substituted alkyl, hydroxy, alkoxy, and perhaloalkyl. In some embodiments, Ar is phenyl or pyridinyl optionally substituted with one or more aryl group substituents selected from halo (e.g., fluoro, chloro, or bromo), alkoxy (e.g., methoxy), and cyano.

In some embodiments, the compound of Formula (I) has a structure of Formula (II):

Scheme 1. Structure of PFI-3 and Approaches to Modify FPI-3.

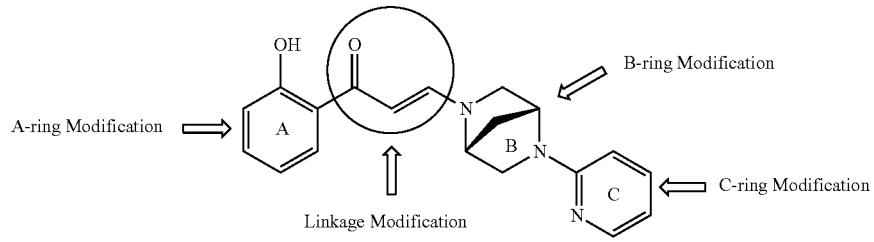

In some embodiments, the presently disclosed subject matter provides a compound having the structure of Formula (I):

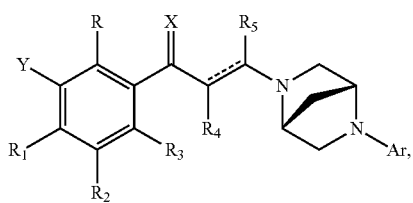

wherein: ----- represents a single or double bond; Ar is selected from cycloalkyl, substituted cycloalkyl, aryl, sub-

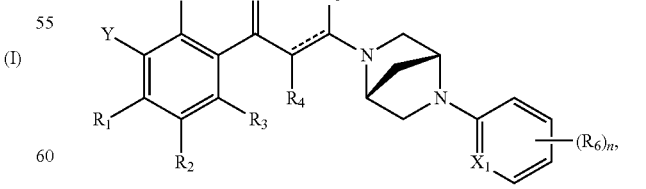

wherein ----- R, Y, X, and $R_1$-$R_5$ are as defined for the compound of Formula (I) and wherein $X_1$ is CH, C($R_7$), or N; n is an integer from 0 to 4 (i.e., 0, 1, 2, 3, or 4); and each $R_6$ and $R_7$ is independently selected from the group comprising cyano, halo, amino, alkyl, substituted alkyl, hydroxy, alkoxy, and perhaloalkyl (e.g., perfluoroalkyl); or a pharmaceutically acceptable salt thereof. In some embodiments, n is 0, 1, or 2. For example, in some embodiments, n is 0 and the compound comprises and pyridine or phenyl ring is unsubstituted (i.e., all $R_6$ sites are occupied by H). In some embodiments, n is 1 or 2 and each $R_6$ is independently cyano, alkoxy, or halo. In some embodiments, $R_6$ is 1 or 2 and each $R_6$ is independently selected from fluoro, chloro, methoxy, or cyano.

In some embodiments, X is O. In some embodiments, $X_1$ is N.

In some embodiments, R and Y together form a group selected from —N=CH—NH—, —N=N—NH—, and —CH=N—NH—. Thus, for example, the compound of Formula (II) can have a structure of Formula (IIa):

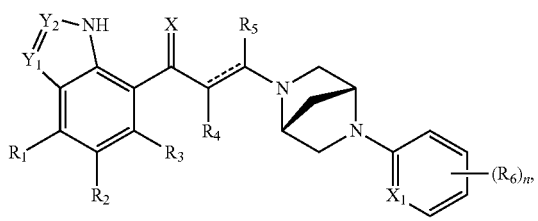

wherein $R_1$-$R_6$, n, X, and $X_1$ are as described from the compound of Formula (II), wherein $Y_1$ is selected from CH and N; and wherein $Y_2$ is selected from CH and M, subject to the proviso that at least one of $Y_1$ and $Y_2$ is N; or a pharmaceutically acceptable salt thereof. Thus, in the compounds of Formula (II) and (IIa), the "A" ring of PFI-3 can be substituted by a fused ring structure selected from indazole, benzimidazole, and benzotriazole.

In some embodiments, X and $R_5$ together can comprise —N—NH—, such that the linkage between the "A" and "B" rings of PFI-3 is replaced by a group containing a 2-pyrazoline or a pyrazole ring. In some embodiments, X and $R_5$ together comprise —N—NH—, R is OH, and $R_2$ is H, fluoro, chloro, or bromo. In some embodiments, ===== is a single bond.

In some embodiments, X is O and R is OH. In some embodiments, $R_2$ is selected from H and halo. In some embodiments, $R_2$ is H, fluoro, chloro, or bromo. In some embodiments, $R_2$ is fluoro. In some embodiments, $R_2$ is bromo. In some embodiments, Y is H. In some embodiments, Y is halo (e.g., bromo).

In some embodiments, X is O and R is H.

In some embodiments, $R_3$ and $R_4$ together form an alkylene group. In some embodiments, $R_3$ and $R_4$ together form an ethylene group (i.e., thereby forming a six-membered ring).

In some embodiments, ===== is a double bond.

In some embodiments, X is O and each of $R_3$, $R_4$, and $R_5$ is H. In some embodiments, R is chloro. In some embodiments, Y is H or halo. In some embodiments, Y is H. In some embodiments, Y is bromo. In some embodiments, n is 0, 1, or 2. In some embodiments, each $R_6$ is halo, alkoxy, or cyano. In some embodiments, $R_7$ is H.

In some embodiments, the compound of Formula (II) has a structure of Formula (III):

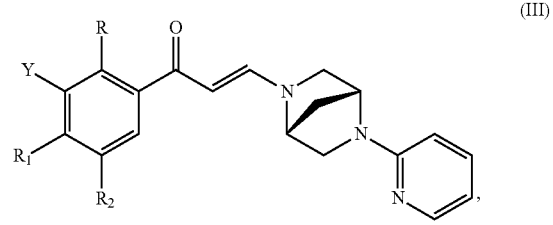

wherein: R is selected from H, hydroxy and halo; Y is H or halo, and $R_1$ and $R_2$ are independently selected from the group selected from H, cyano and halo, subject to the proviso that when R is hydroxy, Y is halo and/or at least one of $R_1$ and $R_2$ is cyano or halo; or a pharmaceutically acceptable salt thereof.

In some embodiments, one of R, $R_1$, and $R_2$ is selected from fluoro, chloro, and bromo. In some embodiments, the compound of Formula (III) is selected from:

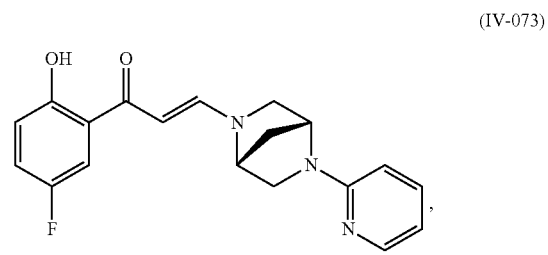

(IV-073)

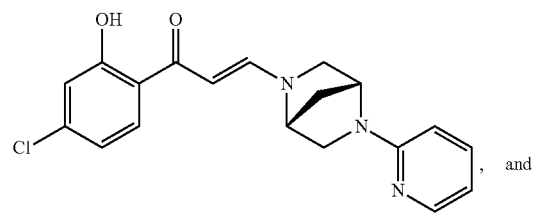

(IV-077)

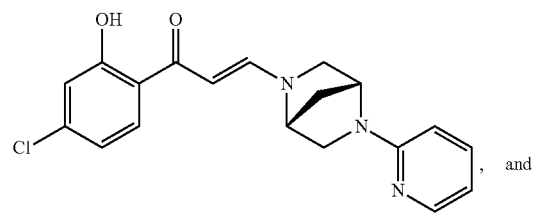

(IV-085)

Additional compounds of Formula (III) include:

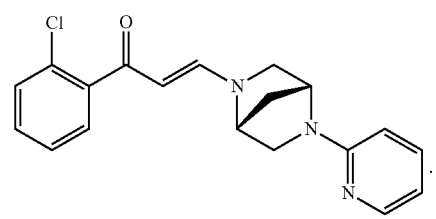

(IV-141)

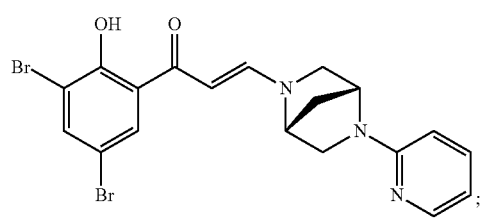
(IV-145)
or a pharmaceutically acceptable salt thereof.
Additional compounds of Formula (I) include, but are not limited to,
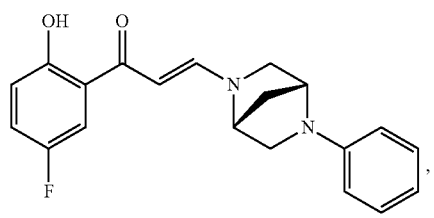,
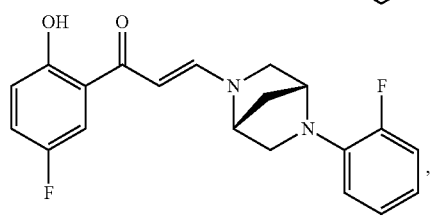,
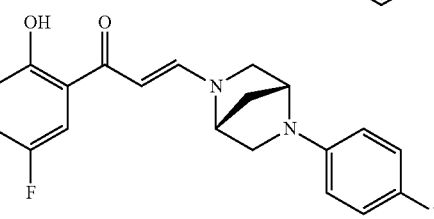,
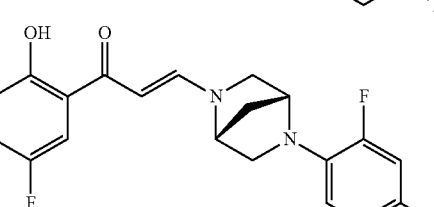,
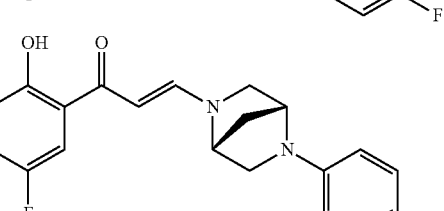,
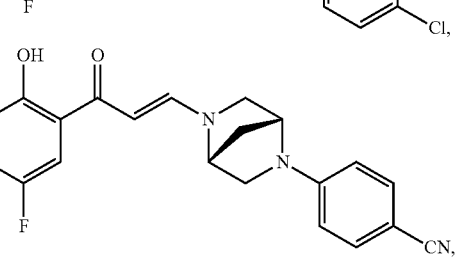,
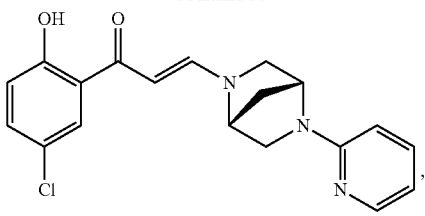,
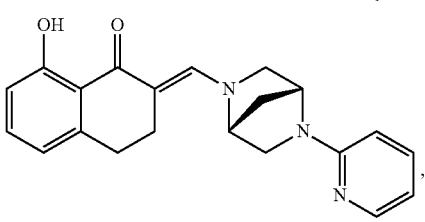,
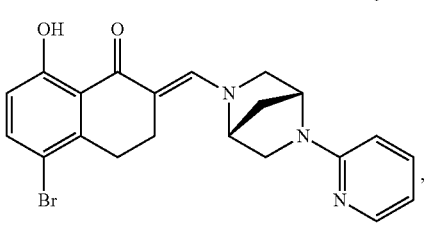,
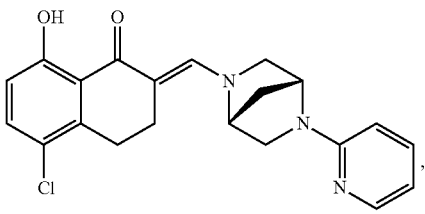,
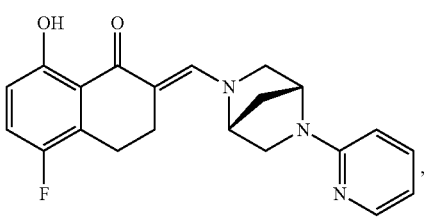,
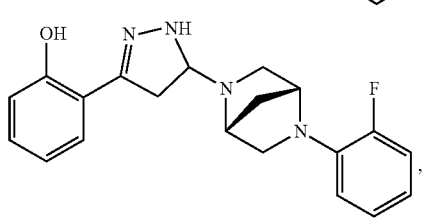,
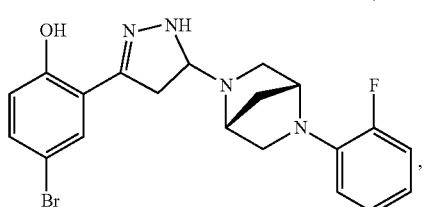,
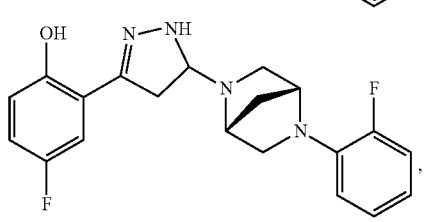, -continued In some embodiments, the compound is selected from the group comprising:

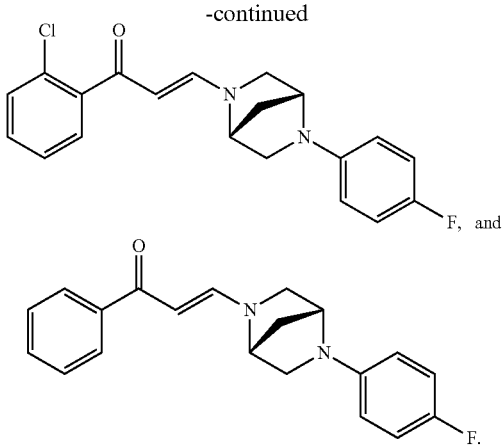

As indicated above, it is to be understood that the disclosed compounds can comprise pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts, and combinations thereof.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N, N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In some embodiments, the presently disclosed compounds can further be provided as a solvate.

IV. Pharmaceutical Compositions

The compounds disclosed herein can be formulated in accordance with the routine procedures adapted for a desired administration route. Accordingly, in some embodiments, the presently disclosed subject matter provides a pharmaceutical composition comprising a therapeutically effective amount of a compound as disclosed hereinabove (e.g., a compound of Formula (I), (II), or Formula (III)) and a pharmaceutically acceptable carrier. The therapeutically effective amount can be determined by testing the compounds in an in vitro or in vivo model and then extrapolating therefrom for dosages in subjects of interest, e.g., humans. The therapeutically effective amount should be enough to exert a therapeutically useful effect in the absence of undesirable side effects in the subject to be treated with the composition.

Pharmaceutically acceptable carriers are well known to those skilled in the art and include, but are not limited to, from about 0.01 to about 0.1M and preferably 0.05M phosphate buffer or 0.8% saline. Such pharmaceutically acceptable carriers can be aqueous or non-aqueous solutions, suspensions and emulsions. Examples of non-aqueous solvents suitable for use in the presently disclosed subject matter include, but are not limited to, propylene glycol, polyethylene glycol, vegetable oils such as olive oil, and injectable organic esters such as ethyl oleate. Aqueous carriers suitable for use in the presently disclosed subject matter include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the presently disclosed subject matter can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the presently disclosed subject matter include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the presently disclosed subject matter can be mixed as needed with disintegrants, diluents, granulating agents, lubricants, binders and the like using conventional techniques known in the art. The carriers can also be sterilized using methods that do not deleteriously react with the compounds, as is generally known in the art. The compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder.

The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

In some embodiments, the pharmaceutical composition comprising the compound of the presently disclosed subject matter can include an agent which controls release of the compound, thereby providing a timed or sustained release compound.

V. Synthesis of BRIs

The presently disclosed BRIs can be prepared using standard synthetic methodology known in the art. For example, the compounds can be made by the methods described hereinbelow or variations thereof that will be apparent to persons skilled in the art based on the present disclosure. As necessary, protecting groups known in the art can be utilized during the synthesis of the compounds.

The syntheses of two exemplary PA BRIs, referred to herein as YH-IV-073 (or IV-073), and YH-IV-077 (or IV-077), as well as of PFI-3 (also referred to herein as YH-IV-081), are shown in Scheme 2, below. As shown in Scheme 2, commercially available tert-butyloxycarbonyl (BOC)-protected amine 1 is contacted with 2-bromopyridine (2) to form intermediate 3. The protecting group can be removed (e.g., via hydrolysis) to give the corresponding amine 4. Compound 4 can be coupled with a carboxylic acid (5, 6, or 7) to afford target YH-IV-073, YH-IV-077 and YH-IV-081, respectively. As described hereinbelow in the Examples, YH-IV-073 and YH-IV-077 show significantly improved sensitizing activity to TMZ in vitro and in an animal model of GBM as compared to PFI-3. These analogs will provide greater insight into the importance of substitution of the A ring.

Scheme 2. Synthetic Strategy for Modifying the 4,5-Positions of the PFI-3 A Ring.

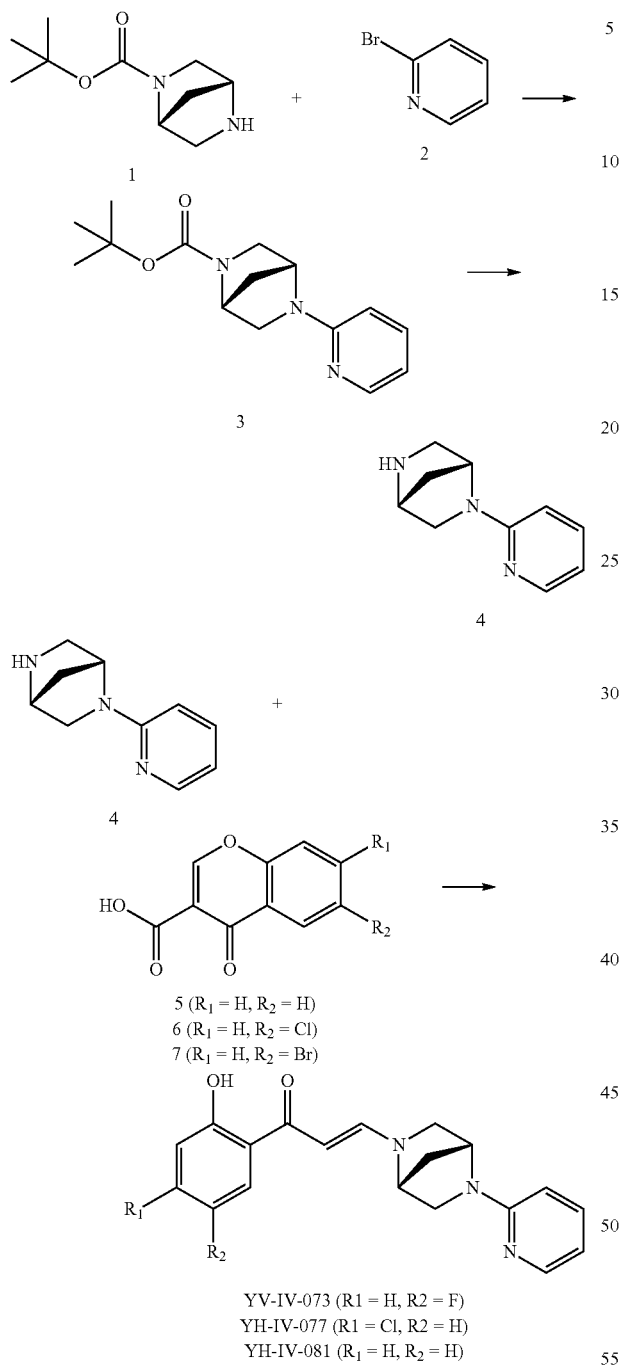

085 is believed to be the first PFI-3 analog prepared without a 2-hydroxy moiety in the A-ring. As described further hereinbelow, YH-IV-085 showed significantly improved sensitizing activity to TMZ in vitro and in an animal model of GBM as compared to PFI-3.

Scheme 3. Synthetic Strategy for Analogs with Modifications at 2-Position of A ring of PFI-3.

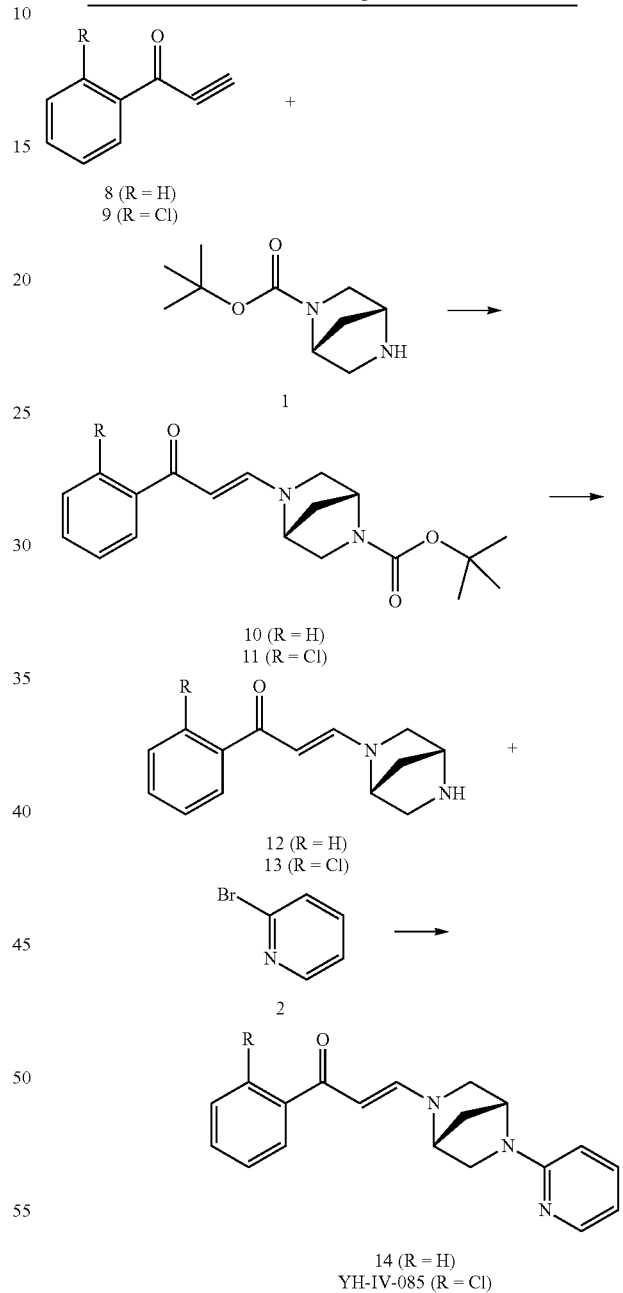

The synthetic route shown in Scheme 3, below, was used to synthesize new analogs with different substituents in the 2-position of the A-ring, such as YH-IV-085. As shown in Scheme 3, a commercially available 1-phenylprop-2-yn-1-one (e.g., 8 or 9) can be reacted with BOC-protected amine compound 1 to afford a BOC-protected intermediate (e.g., 10 or 11), which can be hydrolyzed to provide corresponding deprotected intermediate (12 or 13). The intermediates can be coupled with the 2-bromopyridine (2) to yield target compounds (e.g., 14 or YH-IV-085), respectively. YH-IV-085 is believed to be the first PFI-3 analog prepared without a 2-hydroxy moiety in the A-ring. As described further hereinbelow, YH-IV-085 showed significantly improved sensitizing activity to TMZ in vitro and in an animal model of GBM as compared to PFI-3.

The synthetic route shown in Scheme 4, below, can be used as an alternative synthetic strategy to synthesize YH-IV-085 and other PFI-analogs with different A-rings. As shown in Scheme 4, commercially available 1-(2-chlorophenyl)prop-2-yn-1-one (15) can be reacted with intermediate 4 (which can be prepared as shown in Scheme 2, above) to afford target compound YH-IV-085.

Scheme 4. Alternative Synthesis Stategy for Modifications at 2-Position of A-ring of PFI-3.

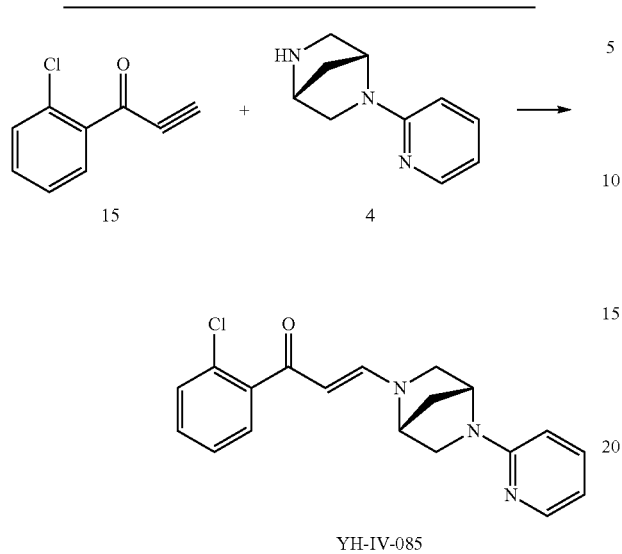

YH-IV-085

Additional compounds of Formula (I) can be prepared according to the routes shown above, for example, by substituting other 1-phenylprop-2-yn-ones in place of compound 15 and/or other aryl halides in place of 2-bromopyridine (2).

VI. Methods of Treating Glioblastoma and/or Inhibiting BRG1 Bromodomain

Disclosed in accordance with some embodiments of the presently disclosed subject matter are methods of medical treatment that involve the administration of a BRI, a pharmaceutically acceptable salt thereof, or a pharmaceutical formulation thereof to a subject in need of treatment for cancer (e.g., glioblastoma). The BRI can enhance the sensitivity of BTIC to chemotherapeutic agents, such as DNA alkylating agents. Thus, administration of the BRI can provide for increased efficacy of a DNA alkylating agent administered to the subject. In some embodiments, administration of the BRI can provide effective treatment despite the administration of lower concentrations of the DNA alkylating agents. In some embodiments, the administration of the BRI provides for the treatment of a treatment-resistant glioblastoma. For example, administration of the BRI can provide for the treatment of a DNA-alkylating agent-resistant glioblastoma with a DNA alkylating agent. In some embodiments, the BRI is a PA as disclosed hereinabove.

In some embodiments, the presently disclosed subject matter provides the use of a BRI, e.g., a compound of Formula (I), (II), or (III) as described hereinabove, for treating cancer. In some embodiments, the cancer is glioblastoma.

In some embodiments, the presently disclosed subject matter provides a method of treating glioblastoma wherein the method comprises: (a) administering to the subject a compound of Formula (I):

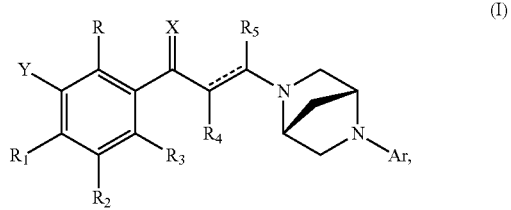

wherein: ===== represents a single or double bond; Ar is selected from cycloalkyl, substituted cycloalkyl, aryl, substituted aryl, heteroaryl, and substituted heteroaryl; R is H, halo, amino, thiol, or hydroxy and Y is H or halo or where R and Y together form a group selected from —N=CH—NH—, —N=N—NH—, and —CH=N—NH—; $R_1$ and $R_2$ are each independently selected from the group comprising H, cyano, halo, alkyl, substituted alkyl, perhaloalkyl (e.g., perfluoroalkyl), alkoxy, cycloalkyl, substituted cycloalkyl, cycloalkenyl, and substituted cycloalkenyl; $R_3$, $R_4$ and $R_5$ are each H; and X is O, S, or NH; or wherein (i) X and $R_5$ together comprise —N—NH— and/or $R_3$ and $R_4$ together form an alkylene group, optionally ethylene or (ii) $R_3$ and $R_5$ together form a covalent bond or methylene group; or a pharmaceutically acceptable salt thereof; and (b) administering to the subject a chemotherapeutic compound, wherein said chemotherapeutic compound is a DNA alkylating agent. In some embodiments, the DNA alkylating agent is TMZ or carmustine. In some embodiments, the glioblastoma is a DNA alkylating agent-resistant glioblastoma.

In some embodiments, the compound of Formula (I) is PFI-3:

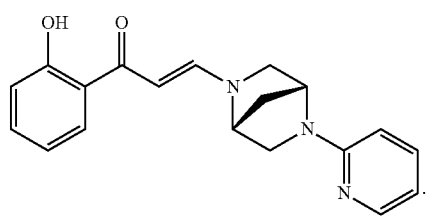 [SMILES: O=C(/C=C/N1C[C@H]2C[C@@H]1CN2c1ccccn1)c1ccccc1O ; "."]

In some embodiments, the compound of Formula (I) is not PFI-3. In some embodiments Ar of Formula (I) is a six-membered aryl or heteroaryl group, such as phenyl or pyridinyl, optionally substituted with one or more aryl group substituents. In some embodiments, the one or more aryl group substituents are selected from halo, alkoxy, and cyano.

In some embodiments, the compound of Formula (I) has a structure of Formula (II):

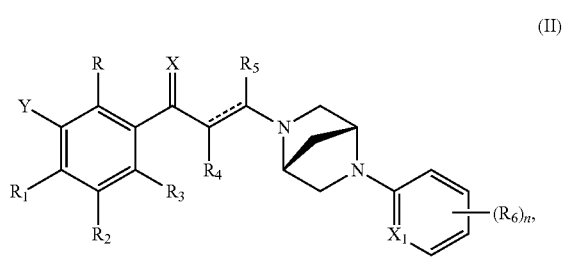

wherein ----- R, Y, X, and R₁-R₅ are as defined for the compound of Formula (I) and wherein X₁ is CH, C(R₇), or N; n is an integer from 0 to 4; and each R₆ and R₇ is independently selected from cyano, halo, amino, alkyl, substituted alkyl, hydroxy, alkoxy, and perhaloalkyl. In some embodiments, n is 0, 1, or 2. In some embodiments, each R₆ is independently selected from fluoro, chloro, methoxy, and cyano.

In some embodiments, X is O. In some embodiments, X₁ is N. In some embodiments, R and Y together form a group selected from —N=CH—NH—, —N=N—NH—, and —CH=N—NH—. In some embodiments, X and R₅ together comprise —N—NH, optionally wherein R is OH and R₂ is H, fluoro, chloro, or bromo. In some embodiments, ----- is a double bond.

In some embodiments, X is O and R is OH. In some embodiments, Y is H. In some embodiments, Y is bromo. In some embodiments, R₂ is selected from H, fluoro, chloro, and bromo. In some embodiments, R₂ is fluoro. In some embodiments, R₂ is bromo.

In some embodiments, X is O and R is halo. In some embodiments, X is O and R is chloro. In some embodiments, X is O and R is H.

In some embodiments, R₃ and R₄ together form an ethylene group.

In some embodiments, the compound of Formula (II) has a structure of Formula (III):

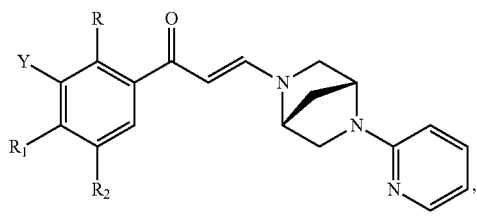

wherein: R is selected from H, hydroxy and halo; Y is H or halo; and R₁ and R₂ are independently selected from the group selected from H, cyano and halo. In some embodiments, R is hydroxy, and Y is halo and/or at least one of R₁ and R₂ is cyano. In some embodiments, one of R, R₁, and R₂ is selected from fluoro, chloro, and bromo.

In some embodiments, the compound of Formula (III) is selected from:

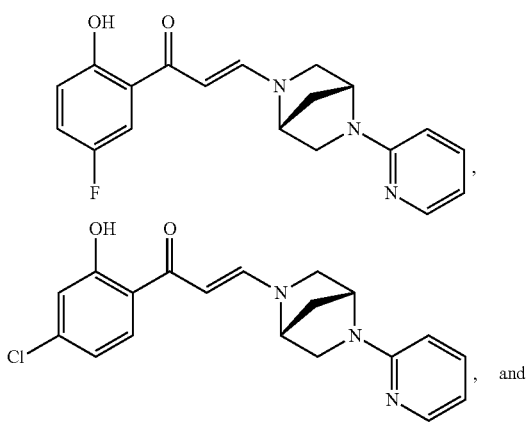

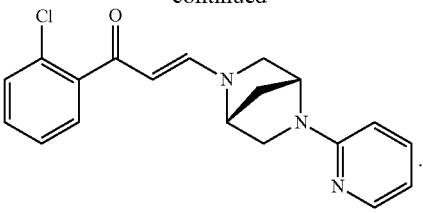

In some embodiments, the presently disclosed subject matter provides a method of inhibiting BRG1 bromodomain, wherein the method comprises contacting a sample comprising BRG1 with a compound of Formula (I):

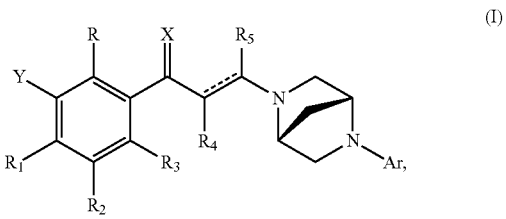

wherein: ----- represents a single or double bond; Ar is selected from cycloalkyl, substituted cycloalkyl, aryl, substituted aryl, heteroaryl, and substituted heteroaryl; R is H, halo, amino, thiol, or hydroxy and Y is H or halo or where R and Y together form a group selected from —N=CH—NH—, —N=N—NH—, and —CH=N—NH—; R₁ and R₂ are each independently selected from the group consisting of H, cyano, halo, alkyl, substituted alkyl, perhaloalkyl (e.g., perfluoroalkyl), alkoxy, cycloalkyl, substituted cycloalkyl, cycloalkenyl, and substituted cycloalkenyl; R₃, R₄ and R₅ are each H; and X is O, S, or NH; or wherein (i) X and R₅ together comprise —N—NH— and/or R₃ and R₄ together form an alkylene group, optionally ethylene, or (ii) R₃ and R₅ together form a covalent bond or methylene group; or a pharmaceutically acceptable salt thereof, subject to the proviso that the compound is not PFI-3. In some embodiments, the sample comprises an in vitro sample comprising cells, tissue, a cell extract or a biological fluid (e.g., saliva, blood, plasma, cerebrospinal fluid, etc.), e.g., from a glioblastoma or other tumor sample. In some embodiments, the sample is an in vivo sample.

Thus, the methods and compositions disclosed herein can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

Suitable methods for administration of a composition of the presently disclosed subject matter to a subject include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of BRIs

General Chemistry Methods:

All chemicals for synthesis were purchased from Sigma-Aldrich Chemical Co. (St. Louis, Missouri, United States of America), Fisher Scientific (Pittsburgh, Pennsylvania, United States of America), Matrix Scientific (Columbia, South Carolina, United States of America), AK Scientific (Mountain View, California, United States of America), Oakwood Products (West Columbia, South Carolina, United States of America) etc. and used without further purification. Moisture-sensitive reactions were carried under an argon atmosphere. Analytical thin-layer chromatography (TLC) was carried out on pre-coated silica gel (Merck Kieselgel 60 $F_{254}$ layer thickness 0.25 mm; MilliporeSigma, Burlington, Massachusetts, United States of America). NMR spectra were obtained on a Bruker Advance III 400 (Bruker Corporation, Billerica, Massachusetts, United States of America) spectrometer. Chemical shifts are reported as parts per million (ppm) relative to TMS in $CDCl_3$ or $DMSO-d_6$. The structure of synthesized compounds was also assigned by $^1H$—$^1H$ 2D-COSY and 2D-NOE NMR analytic methods. Flash column chromatography was performed on using silica gel (230-400 mesh, MilliporeSigma, Burlington, Massachusetts, United States of America). Mass spectral data was collected on a Bruker Esquire-LC/MS system (Bruker Corporation, Billerica, Massachusetts, United States of America) equipped with electrospray/ion trap instrument in positive and negative ion modes (ESI source). The purity of the final compounds was analyzed by an Agilent 1100 HPLC system (Agilent Technologies, Santa Clara, California, United States of America). HPLC conditions: 45% acetonitrile at flow rate of 1.0 mL/min using a LUNA 5µ C18 100A column (250×4.60 mm) purchased from Phenomenex (Torrance, California, United States of America) at ambient temperature. UV detection was set at 340 nm or 245 nm. Purities of the compounds were established by careful integration of areas for all peaks detected and determined as 95% for all compounds tested for biological study.

(1R,4R)-tert-butyl 5-(pyridin-2-yl)-2,5-diazabicyclo [2.2.1]heptane-2-carboxylate (3)

To a mixture of (1R,4R)-tert-butyl 2,5-diazabicyclo [2.2.1]heptane-2-carboxylate (1.00 g, 0.005035 mol) in anhydrous tetrahydrofuran (THF, 30 mL) was added 2-bromopyridine (1.59 g, 0.01007 mol), NaOBu-t (0.485 g, 0.005035 mol), $Pd(OAc)_2$ (57 mg, 0.0002522 mol), and (R)-(+)-2,2'-bis(diphenylphosphino)-1,1'-binaphthalene (BINAP, 0.157 g, 0.0002522 mol) at room temperature under the argon atmosphere. After the end of the reaction was established by TLC, the reaction was quenched by water, and the product was extracted with ethyl acetate. The organic layer was dried with magnesium sulfate ($MgSO_4$), filtered, and concentrated under vacuum. The product was purified by a silica gel column using hexanes and ethyl acetate (1:1) as eluent to afford 0.96 g (70%) of the desired compound as yellowish solid.

$^1HNMR$ (400 MHz, $DMSO-d_6$) δ 8.06 (d, J=4.8 Hz, 1H, ArH), 7.51-7.47 (m, 1H, ArH), 6.60-6.57 (m, 1H, ArH), 6.54-6.51 (m, 1H, ArH), 4.77 (d, J=8.8 Hz, 1H, CH), 3.51-3.45 (m, 1H, CH), 3.44-3.30 (m, 2H, CH), 3.26-3.33 (m, 1H, CH), 3.18-3.15 (m, 1H, CH), 1.90-1.87 (m, 2H, CH), 1.39 (s, 6H, 2×$CH_3$), 1.34 (s, 3H, $CH_3$).

Mass (ESI, Negative): $[M-H]^-$; (ESI, Positive): $[M+Na]^+$.

(1R,4R)-2-(pyridin-2-yl)-2,5-diazabicyclo[2.2.1]heptane (4)

A solution of (1R,4R)-tert-butyl 5-(pyridin-2-yl)-2,5-diazabicyclo [2.2.1] heptane-2-carboxylate (0.62 g, 0.0022517 mol) in methanol (10 mL) was cooled in a ice-water bath under argon atmosphere and then 2N HCl in diethyl ether (Et$_2$O, 10 mL, 0.020265 mol) was added. The resulting reaction mixture was allowed to stir for 30 minutes at room temperature under argon. The end of the reaction was established by TLC, and then the product was concentrated under vacuum to afford 0.60 g as yellowish solid. The product was used for the next step without further purification.

$^1$HNMR (400 MHz, DMSO-d$_6$) δ 8.13 (d, J=4.8 Hz, 1H, ArH), 7.48-7.43 (m, 1H, ArH), 6.63-6.58 (m, 1H, ArH), 6.37-6.32 (m, 1H, ArH), 5.03 (d, J=7.8 Hz, 1H, CH), 4.54-4.50 (m, 1H, CH), 3.68-3.65 (m, 1H, CH), 3.61-3.49 (m, 2H, CH), 3.44-3.38 (m, 1H, CH), 2.12-1.91 (m, 2H, CH).

Mass (ESI, Negative): [M–H]$^-$; (ESI, Positive): 176.06 [M+H]$^+$; 198.09 [M+Na]$^+$.

(E)-1-(5-fluoro-2-hydroxyphenyl)-3-((1R,4R)-5-(pyridin-2-yl)-2,5-diazabicyclo[2.2.1]heptan-2-yl)prop-2-en-1-one (YH-IV-073)

To a solution of (1R,4R)-2-(pyridin-2-yl)-2,5-diazabicyclo[2.2.1]heptane (0.175 g, 0.0010 mol) in ethanol (10 mL) was added diisopropylethylamine (DIPEA, 0.65 g, 0.0050 mol) at room temperature under the argon atmosphere. The reaction was stirred to homogeneity at room temperature under argon. 6-fluoro-4-oxo-4H-chromene-3-carboxylic acid (0.208 g, 0.0010 mol) was added to the reaction, and the mixture was allowed to stir for 4-5 hours under the same conditions. After the end of the reaction was established by TLC, the reaction was quenched by water and extracted with ethyl acetate. The organic layer was dried with MgSO$_4$, filtered, and concentrated under vacuum. The product was purified by a silica gel column using dichloromethane (DCM) and methanol (19:1) as eluent to afford 0.27 g (79%) of the desired compound as a brown solid.

$^1$HNMR (400 MHz, DMSO-d$_6$) δ 13.57 (s, 1H, OH), 8.17-8.14 (m, 2H, ArH), 7.51-7.47 (m, 1H, ArH), 7.28-7.25 (m, 1H, ArH), 7.09-7.04 (m, 1H, ArH), 6.88-6.85 (m, 1H, ArH), 6.65 (t, J=6.0 Hz, 1H, CH), 6.37 (d, J=8.2 Hz, 1H, CH), 5.08 (s, 1H, CH), 4.45 (s, 1H, CH), 3.71-3.68 (m, 1H, CH), 3.52-3.45 (m, 2H, CH), 3.42-3.39 (m, 1H, CH), 2.17 (d, J=8.8 Hz, 1H, CH), 2.08 (d, J=8.8 Hz, 1H, CH).

Mass (ESI, Negative): [M–H]$^-$; (ESI, Positive): 340.11 [M+H]$^+$.

HRMS [C$_{19}$H$_{19}$FN$_3$O$_2^+$]: calcd 340.1461, found [M+H]$^+$. Purity: % (HPLC).

(E)-1-(4-chloro-2-hydroxyphenyl)-3-((1R,4R)-5-(pyridin-2-yl)-2,5-diazabicyclo[2.2.1]heptan-2-yl)prop-2-en-1-one (YH-IV-077)

To a solution of (1R,4R)-2-(pyridin-2-yl)-2,5-diazabicyclo[2.2.1]heptane (0.175 g, 0.0010 mol) in ethanol (10 mL), DIPEA (0.65 g, 0.0050 mol) was added at room temperature under argon atmosphere. The reaction was stirred until homogenous at room temperature under argon. 7-chloro-4-oxo-4H-chromene-3-carboxylic acid (0.225 g, 0.0010 mol) was added to the reaction, and the resulting reaction mixture was allowed to stir for 2-3 hours under the same conditions. After the end of the reaction was established by TLC, the reaction was quenched by water and extracted with ethyl acetate. The organic layer was dried with MgSO$_4$, filtered, and concentrated under vacuum. The product was purified by a silica gel column using DCM and ethyl acetate (9:1) as eluent to afford 0.117 g (33%) of the desired compound as yellow solid.

$^1$HNMR (400 MHz, DMSO-d$_6$) δ 14.16 (s, 1H, OH), 8.17 (s, 1H, ArH), 8.15 (d, J=6.8 Hz, 1H, ArH), 7.53-7.47 (m, 2H, ArH), 6.92 (d, J=2.0 Hz, 1H, ArH), 6.67 (dd, J=8.8 Hz, J=1.6 Hz, 1H, ArH), 6.66-6.63 (m, 2H, ArH), 6.37(t, J=8.2 Hz, 1H, CH), 5.62 (d, J=12.0 Hz, 1H, CH), 5.08 (s, 1H, CH), 4.44 (s, 1H, CH), 3.71 (d, J=7.6 Hz, 1H, CH), 3.51-3.44 (m, 2H, CH), 3.40 (d, J=8.6 Hz, 1H, CH), 2.17 (d, J=10.0 Hz, 1H, CH), 2.07 (d, J=11.2 Hz, 1H, CH).

Mass (ESI, Negative): [M–H]$^-$; (ESI, Positive): 356.13 [M+H]$^+$.

HRMS [C$_{19}$H$_{19}$ClN$_3$O$_2^+$]: calcd 356.1166, found [M+H]$^+$. Purity: % (HPLC).

(E)-1-(2-hydroxyphenyl)-3-((1R,4R)-5-(pyridin-2-yl)-2,5-diazabicyclo[2.2.1]heptan-2-yl)prop-2-en-1-one (YH-IV-081/PFI-3)

To a solution of (1R,4R)-2-(pyridin-2-yl)-2,5-diazabicyclo[2.2.1]heptane (0.175 g, 0.0010 mol) in ethanol (10 mL), DIPEA (0.65 g, 0.0050 mol) was added at room temperature under argon atmosphere. The reaction was stirred to homogeneity at room temperature under argon. 4-oxo-4H-chromene-3-carboxylic acid (0.19 g, 0.0010 mol) was added to the reaction, and the resulting reaction mixture was allowed to stir for 2-3 hours under the same conditions. After the end of the reaction was established by TLC, the reaction was quenched by water, and extracted with ethyl acetate. The organic layer was dried with MgSO$_4$, filtered, and concentrated under vacuum. The product was purified by a silica gel column using DCM and methanol (19:1) as eluent to afford 0.256 g (80%) of the desired compound as yellow solid.

$^1$HNMR (400 MHz, cdcl$_6$) δ 8.16 (d, J=12.0 Hz, 1H, CH), 8.15 (d, J=8.0 Hz, 1H, Pyridine-H), 7.62 (d, J=8.0 Hz, 1H, ArH), 7.48 (t, J=8.0 Hz, 1H, Pyridine-H), 7.34 (t, J=8.0-8.2 Hz, 1H, ArH), 6.93 (d, J=8.2 Hz, 1H, ArH), 6.79 (t, J=7.2-7.6 Hz, 1H, ArH), 6.64 (t, J=6.2-6.4 Hz, 1H, Pyridine-H), 6.36 (d, J=8.2 Hz, 1H, Pyridine-H), 5.71 (d, J=12.0 Hz, 1H, CH), 5.07 (s, 1H, CH), 4.43 (s, 1H, CH), 3.69-3.67(m 1H, CH), 3.51-3.44 (m, 2H, CH), 3.40-3.38 (m, 1H, CH), 2.16-2.13 (m, 1H, CH), 2.07-2.05 (m, 1H, CH).

Mass (ESI, Negative): [M–H]$^-$; (ESI, Positive): 322.11 [M+H]$^+$.

HRMS [C$_{19}$H$_{20}$N$_3$O$_2^+$]: calcd 322.1556, found [M+H]$^+$. Purity: % (HPLC).

(1R,4R)-tert-butyl 5-((E)-3-oxo-3-phenylprop-1-en-1-yl)-2,5-diazabicyclo[2.2.1]heptane-2-carboxylate (10)

To a solution of (1R,4R)-2-(pyridin-2-yl)-2,5-diazabicyclo[2.2.1]heptane (0.13 g, 0.001 mol) in ethanol (10 mL), DIPEA (0.87 mL, 0.005 mol) was added at room temperature under argon atmosphere. The reaction was stirred to homogeneity at room temperature under argon. 1-phenyl-prop-2-yn-1-one (0.20 g, 0.001 mol) was added to the reaction, and the resulting reaction mixture was allowed to stir for 12 hours under the same conditions. After the end of the reaction was established by TLC, the reaction was quenched by water, and extracted with ethyl acetate. The organic layer was dried with MgSO$_4$, filtered, and concentrated under vacuum. The product was purified by a silica gel column using DCM and methanol (19:1) as eluent to afford 0.305 g (92%) of the desired compound as yellow solid.

$^1$HNMR (400 MHz, CDCl$_3$) δ 8.03 (d, J=8.0 Hz, 1H), 7.90-7.88 (m, 1H), 7.49-7.40 (m, 3H), 5.74-5.71 (m 1H), 4.69-4.57 (m, 1H), 4.28 (s, 1H), 3.45-3.37 (m, 4H), 1.97-1.90 (m, 2H), 1.49 (s, 3H), 1.45 (s, 6H).

Mass (ESI, Negative): [M–H]$^-$; (ESI, Positive): 329.10 [M+H]$^+$.

(E)-3-((1R,4R)-2,5-diazabicyclo[2.2.1]heptan-2-yl)-1-phenylprop-2-en-1-one (12)

A solution of (1R,4R)-tert-butyl 5-((E)-3-oxo-3-phenyl-prop-1-en-1-yl)-2,5-diazabicyclo[2.2.1]heptane-2-carboxylate (0.30 g, 0.0009135 mol) in methanol (10 mL) was cooled in a ice-water bath under an argon atmosphere, and then 4N HCl in Et$_2$O (2.1 mL, 0.00822 mol) was added. The resulting reaction mixture was stirred 30 minutes at room temperature under argon. After the end of the reaction was established by TLC, the reaction was concentrated under vacuum to produce a yellowish solid of 0.31 g. The product was used for the next step without further purification.

$^1$HNMR (400 MHz, DMSO-d$_6$) δ

Mass (ESI, Negative): [M–H]$^-$; (ESI, Positive): 229.09 [M+H]$^+$.

(E)-1-(2-chlorophenyl)-3-((1R,4R)-5-(pyridin-2-yl)-2,5-diazabicyclo [2.2.1] heptan-2-yl) prop-2-en-1-one (YH-IV-085)

DIPEA (0.44 mL, 0.0025 mol) was added to a solution of (1R,4R)-2-(pyridin-2-yl)-2,5-diazabicyclo [2.2.1] heptane (0.0867 g, 0.0005 mol) in ethanol (8 mL) at room temperature under argon atmosphere. The reaction was stirred to homogeneity at room temperature under argon. 1-(2-chlorophenyl) prop-2-yn-1-one (0.0825 g, 0.0005 mol) was added the reaction, and the resulting reaction mixture was allowed to stir for 12 hours under the same conditions. After the end of the reaction was established by TLC, the reaction was quenched by water, and extracted with ethyl acetate. The organic layer was dried with MgSO$_4$, filtered, and concentrated under vacuum. The product was purified by a silica gel column using DCM and methanol (19:1) as eluent, resulting in 0.182 g (53.7%) of the desired compound as a light brown solid.

$^1$HNMR (400 MHz, DMSO$_6$) δ 8.15 (d, J=4.4 Hz, 1H, CH), 7.50 (t, J=7.2-8.0 Hz, 1H, ArH), 7.34-7.36 (m, 2H, ArH), 7.30-7.24 (m 3H, ArH), 6.64 (t, J=6.0 Hz, 1H, ArH), 6.36 (d, J=8.2 Hz, 1H, ArH), 5.29 (d, J=12.4 Hz, 1H, CH), 5.01 (s, 1H, CH), 4.31 (s, 1H, CH), 3.64 (m 1H, CH), 3.43-3.33 (m, 3H, CH), 2.11 (d, J=9.2 Hz, 1H, CH), 2.04 (d, J=9.2-10.0 Hz, 1H, CH).

Mass (ESI, Negative): [M–H]$^-$; (ESI, Positive): 340.09 [M+H]$^+$.

HRMS [C$_{19}$H$_{19}$ClN$_3$O$^+$]: calcd 340.1217, found [M+H]$^+$. Purity: % (HPLC).

Example 2

BRG1 and Treatment of GBM

BRG1 and BTIC Stemness:

Since BRG1 has been considered to be a tumor suppressor in several cancers, REMBRANDT (REpository for Molecular BRAin Neoplasia DaTa) was queried for BRG1 expression in normal brain tissue and GBM. It was found that BRG1 expression was relatively high in GBM. The expression of the two catalytic subunits of the SWI/SNF complex in BTICs isolated from three different GBM patients (referred to as GBM6, X10, and X16) was examined and it was found that BRG1 was highly expressed in all BTICs examined, while BRM was absent from the X10 BTICs.[2,10] To elucidate the role of BRG1 in BTICs, BRG1-KD BTICs were generated by transducing GBM6 and X16 BTICs with lentivirus encoding scrambled- or BRG1-shRNA, and stable pools of BTICs were isolated after puromycin selection. As expected, BRG1 expression was markedly decreased in BRG1-KD cells, while BRM levels were unaffected.[2] In contrast, BRG1 and BRM levels were not reduced in scrambled-shRNA treated cells. Since BTICs express a number of stem cell markers (CD44, OCT4, and Nanog), the effect of BRG1-KD on the expression of these marker genes by qPCR was examined and it was found that BRG1-KD significantly attenuated their expression in BTICs.[2] It was also recently shown that BTICs can be induced to differentiate into cells of different lineages.[53] The expression of astrocytic markers, Glial fibrillary acidic protein (GFAP) and S100B, and the oligodendrocyte marker Olig2, was evaluated and found BRG1-KD significantly increased their expression in both GBM6 and X16 BTICs.[2,10] Taken together, these data suggest that BRG1 is important in maintaining BTICs in their stem cell-like, undifferentiated state. BRG1 loss promotes BTICs proliferation in vitro and in vivo:

BRG1 plays an important role in cell cycle regulation and proliferation of hESCs.[27,28] The role of BRG1 on BTIC proliferation was examined, and it was found that BRG1-KD in GBM6 and X16 BTICs showed markedly increased cell proliferation when compared to control BTICs.[2] Previous studies show that BRG1 loss is associated with the inactivation of the function of the retinoblastoma (RB) family members, p107 and p130, through their hyper-phosphorylation.[62] To elucidate the underlying mechanism by which BRG1 regulates BTIC growth, the phosphorylation status of p107 and p130 was analyzed. Increased p107 and p130 phosphorylation was observed in the BRG1-KD BTICs.[2] In addition, Cyclin A2 expression increased in BRG1-KD GBM6 and X16 BTICs, while CDK1 levels remained unchanged.[2] Taken together these results suggest that BRG1 restrained BTIC proliferation. The tumorigenic potential of BRG1-KD and control BTICs was determined by intracranial injection of luciferase-labeled BTICs into immunocompromised NSG mice. Tumor progression was determined at weekly intervals by live animal imaging after luciferin injection. BRG1-KD BTICs produced tumors more rapidly and the tumors were significantly larger at the end-point of the study as determined by bioluminescence.[2] Since BRG1-KD in BTICs resulted in GFAP and S100B upregulation in vitro, GFAP and S100B expression was evaluated in BRG1-KD X16 BTIC-induced tumors and it was found that they had markedly higher GFAP and S100B protein expression.[10] Ki67 (a marker for cell proliferation) staining was also much higher in BRG1-KD tumors. These results suggest that BRG1 restrains BTIC differentiation and proliferation in vivo and in vitro.

Figure 1F:
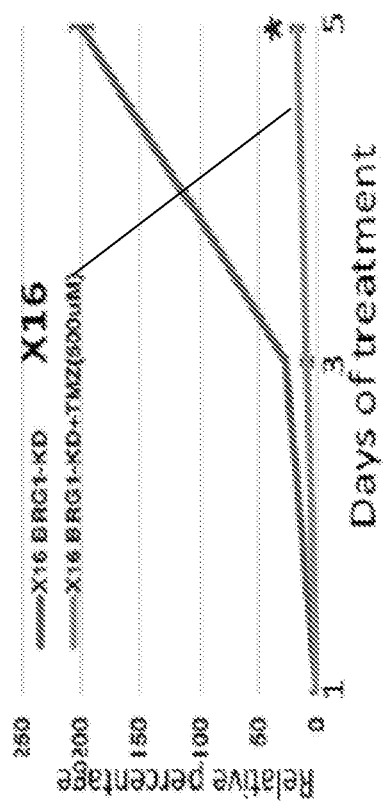
FIG. 1F is a graph showing the effect of temozolomide (TMZ) on the tumorigenicity of control (black portion of bars) and Brahma-related gene-1-knock-down (BRG1-KD) (grey portion of bars) brain-tumor initiating cells (BTICs) after injection of $10^6$ tumor cells into the flanks of immunodeficient mice. Live animal imaging preformed at weekly intervals. After confirming tumor initiation by live animal imaging, mice were treated with TMZ by interperitoneal (IP) injection (10 milligrams per kilogram (mg/kg) on alternate days). The reduction in tumor volume was calculated at 1 week (left) and 2 weeks (right) post-treatment. *p≤0.05.
Figure 1E:
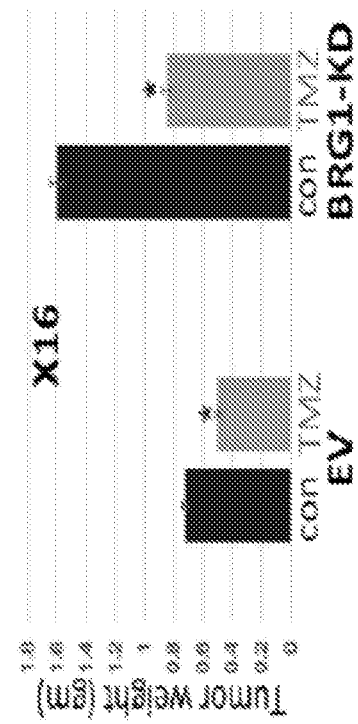
FIG. 1E is an immunoblot image of lysates from control and Brahma-related gene-1-knock-down (BRG1-KD) brain-tumor initiating cells (BTICs) immunoblotted for $O^6$-methylguanine methyltransferase (MGMT, top) and actin (bottom).
Figure 1G:
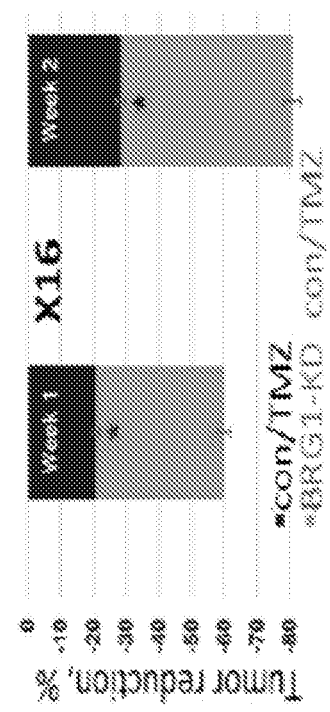
FIG. 1G is a graph showing tumor weight (in grams (gm)) at necropsy for the mice described for FIG. 1F. *p≤0.05.
Figure 2B:
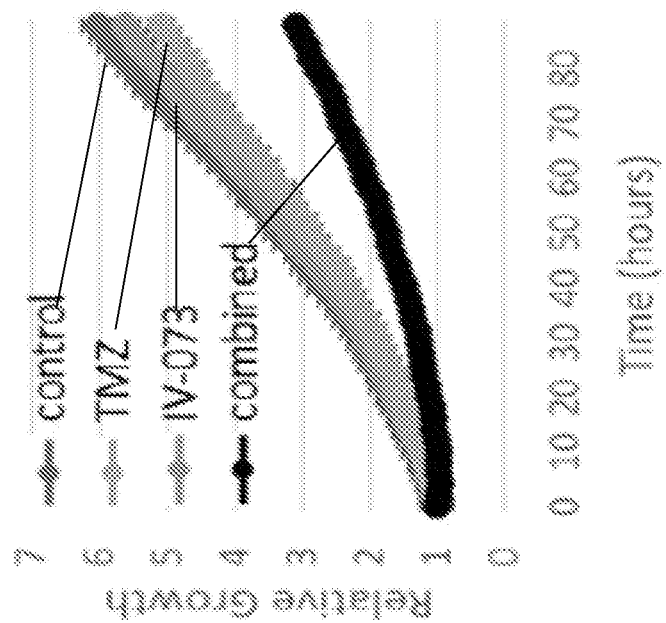
FIG. 2B is a graph showing relative growth of temozolomide (TMZ)-resistant glioma cells (LN229 cells) alone (control); after treatment with 100 micromolar (μM) TMZ; after treatment with a Brahma-related gene-1 bromodomain inhibitor (BRI), IV-073 (1 μM); or after treatment with both TMZ and IV-073 (combined).
Figure 2A:
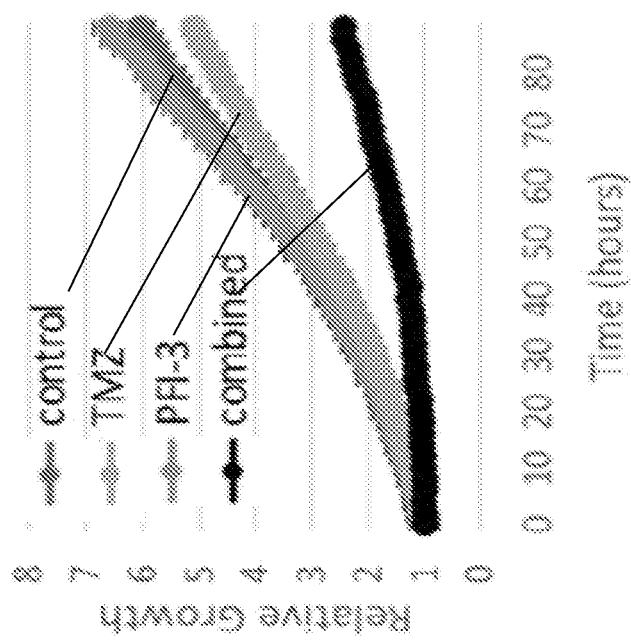
FIG. 2A is a graph showing relative growth of temozolomide (TMZ)-resistant glioma cells (LN229 cells) alone (control); after treatment with 100 micromolar (μM) TMZ; after treatment with a Brahma-related gene-1 bromodomain inhibitor (BRI), PFI-3 (1 μM); or after treatment with both TMZ and PFI-3 (combined).
Figure 2D:
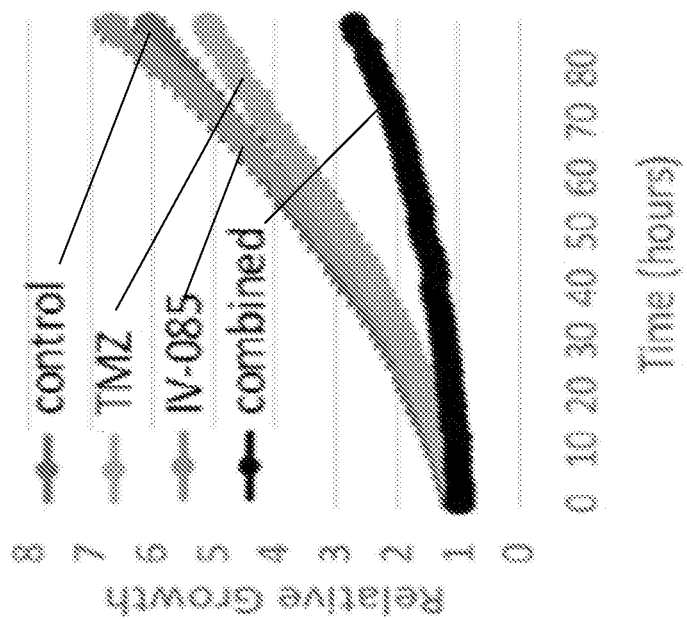
FIG. 2D is a graph showing relative growth of LN229 Temozolomide (TMZ)-resistant glioma cells alone (control); after treatment with 100 micromolar (μM) TMZ; after treatment with a Brahma-related gene-1 bromodomain inhibitor (BRI), IV-085 (1 μM); or after treatment with both TMZ and IV-085 (combined).
Figure 2C:
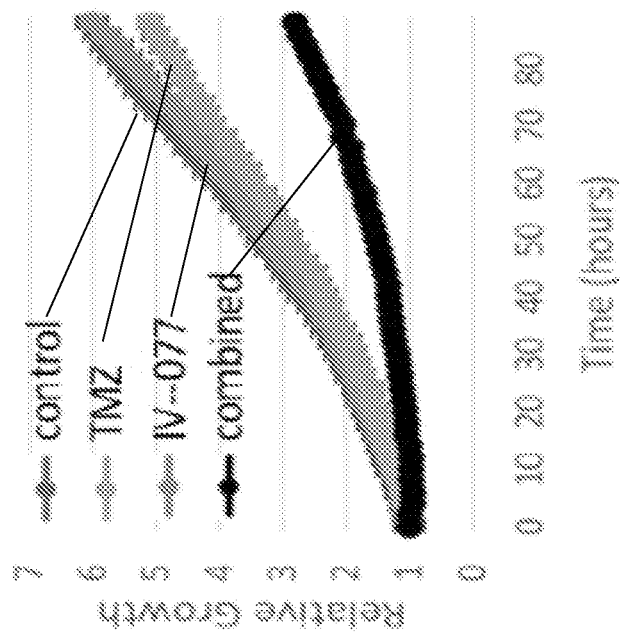
FIG. 2C is a graph showing relative growth of LN229 Temozolomide (TMZ)-resistant glioma cells alone (control); after treatment with 100 micromolar (μM) TMZ; after treatment with a Brahma-related gene-1 bromodomain inhibitor (BRI), IV-077 (1 μM); or after treatment with both TMZ and IV-077 (combined).

BRG1 loss sensitizes BTICs to TMZ in vitro and in vivo: Although the alkylating agent TMZ is front-line chemotherapy in the treatment of GBM, a significant clinical problem is intrinsic or adaptive resistance to TMZ.[63] To evaluate TMZ sensitivity, GBM6 or X16 BTICs were treated with 300 μM or 500 μM TMZ, and cell proliferation was determined. GBM6 BTICs were highly sensitive to both TMZ concentrations and TMZ resulted in a marked reduction in cell viability. See FIG. 1A. In contrast, X16 BTICs were highly TMZ resistant. See FIG. 1A. TMZ resistance in GBM is linked to MGMT ($O^6$-methylguanine methyltransferase) expression, which is a DNA repair protein.[63,64] To assess its involvement in the TMZ sensitivity of BTICs, MGMT mRNA and protein expression were determined and significantly higher MGMT expression was found in X16 BTICs as compared to GBM6 BTICs. See FIGS. 1B and 1C. Since BRG1 has been implicated in DNA double-strand break repair,[65-67] it was hypothesized that BRG1 loss in BTICs would sensitize BTICs to TMZ. It was found that BRG1-KD indeed sensitized X16 BTICs to TMZ, although control X16 BTICs were TMZ-resistant. See FIG. 1D. Furthermore, BRG1 loss in X16 BTICs resulted in reduced MGMT expression consistent with their sensitization to TMZ. See FIG. 1E. To determine whether BRG1-KD sensitized BTICs to TMZ in vivo, animal studies were conducted with control (scrambled shRNA) and BRG1-KD X16 BTICs injected into the flanks of NSG mice. After tumor initiation was confirmed by live animal imaging, mice were treated with TMZ. Although TMZ had little effect on BTIC tumor growth, TMZ markedly reduced tumor growth in BRG1-KD BTICs (see FIG. 1F), and at necropsy the tumors were noticeably smaller. See FIG. 1G. Thus, despite X16 BRG1-KD BTICs producing larger tumors, the tumors were sensitized to TMZ therapy. These results indicate that BRG1 remains a potential druggable target in BTICs.

Pharmacologic inhibition of the BRG1 bromodomain sensitizes drug-resistance BTICs to TMZ and Carmustine: PFI-3 is a bromodomain inhibitor of the BRG1 and BRM subunits of SWI/SNF complex.[46] In contrast to the finding that BRG1-KD increased BTIC proliferation, PFI-3 alone had only a slight growth inhibitory effect on BTIC proliferation. Most importantly, the combination of TMZ and PFI-3 had a markedly greater effect on X16 BTIC proliferation than either agent alone.[2] Since it was determined that BRG1-KD upregulated GFAP expression (marker of differentiation), the effect of PFI-3 on GFAP expression in X16 BTICs was also examined and it was found that PFI-3 upregulated GFAP protein expression.[2] X10 BTICs were isolated from another PDX that does not express the BRM subunit. X10 BTICs have high MGMT expression and are highly TMZ resistant.[2] However, the combination of PFI-3 and TMZ had a marked effect on X10 BTIC proliferation.[2] Similar to the findings with TMZ, X10 and X16 BTICs were highly resistant to Carmustine (another DNA alkylating agent used to treat GBM patients[68]). PFI-3 treatment sensitized X10 and X16 BTICs to Carmustine.[2] Taken together, it appeared that PFI-3 sensitized BTICs to the effects of DNA alkylating agents, and this appeared to depend on the presence of the BRG1 subunit of the SWI/SNF complex and not the BRM subunit. These studies indicate that BRG1 bromodomain inhibitors can sensitize BTICs to various therapies by affecting various pathways critical in cancer (proliferation, differentiation, DNA damage response, etc.).

To determine whether PFI-3 (also called YH-IV-081) and its analogs (referred to herein as "PAs") enhanced TMZ sensitivity IncuCyte live cell imaging proliferation assays (high throughput system) were performed with the LN229 TMZ-resistant glioma cell line. Although PFI-3 (YH-IV-081) and PAs (IV-073, IV-077 and IV-085) alone had relatively minor effects on cell growth, they all potently sensitized LN229 glioma cells to TMZ. See FIGS. 2A-2D.

Figure 3:
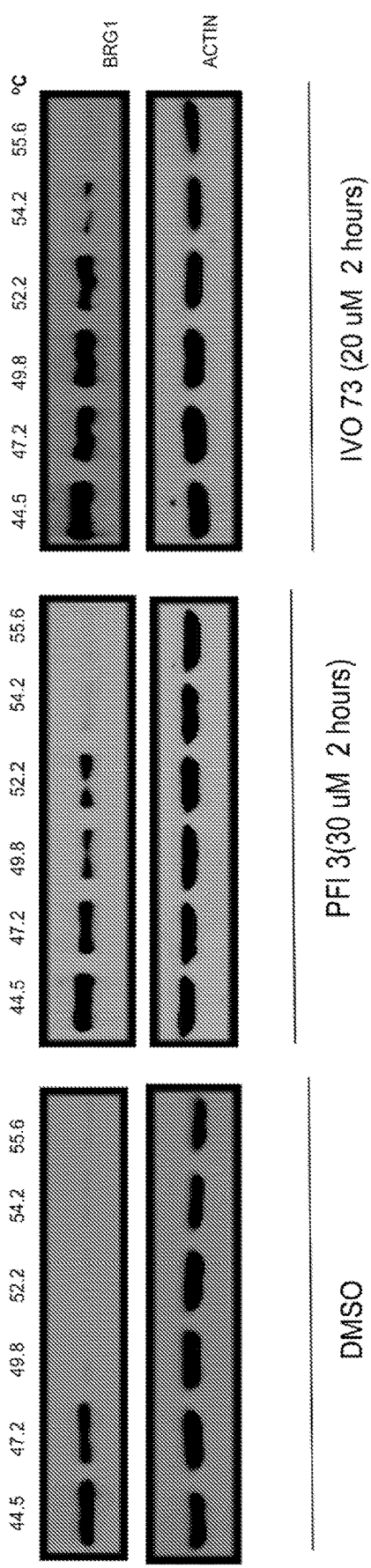
FIG. 3 is a series of immunoblot images showing the effects of Brahma-related gene-1 bromodomain inhibitors (BRIs) on the stability of the bromodomain of Brahma-related gene-1 in a thermal assay shift of the bromodomain in glioblastoma cells over a temperature range from 44.5 degrees Celsius (° C.) to 55.6° C. Cells were treated with (middle) PFI-3 (30 micromolar (µM)) for two hours or (right), a PFI-3 analog of the presently disclosed subject matter (IV-073) (20 µM) for two hours. For comparison, control cells treated with dimethyl sulfoxide (DMSO) are shown at the right.

To further study the activity of the presently disclosed PFI-3 analogs, a thermal shift assay was employed. The assay involved the use of the bromodomain of BRG1 in MT330 GBM cells at temperatures ranging from 44.5° C. to 55.6° C. In the thermal shift assay, the bromodomain is more stable at higher temperatures when an inhibitory molecule is bound. As shown in FIG. 3, 3PFI-3 stabilizes the BRG1 bromodomain as compared to the control (DMSO). However, at a lower dose the IV-073 compound is more effective in stabilizing the bromodomain. This suggests that PA IV-073 binds to the BRG1 bromodomain better than PFI-3.

Figure 4:
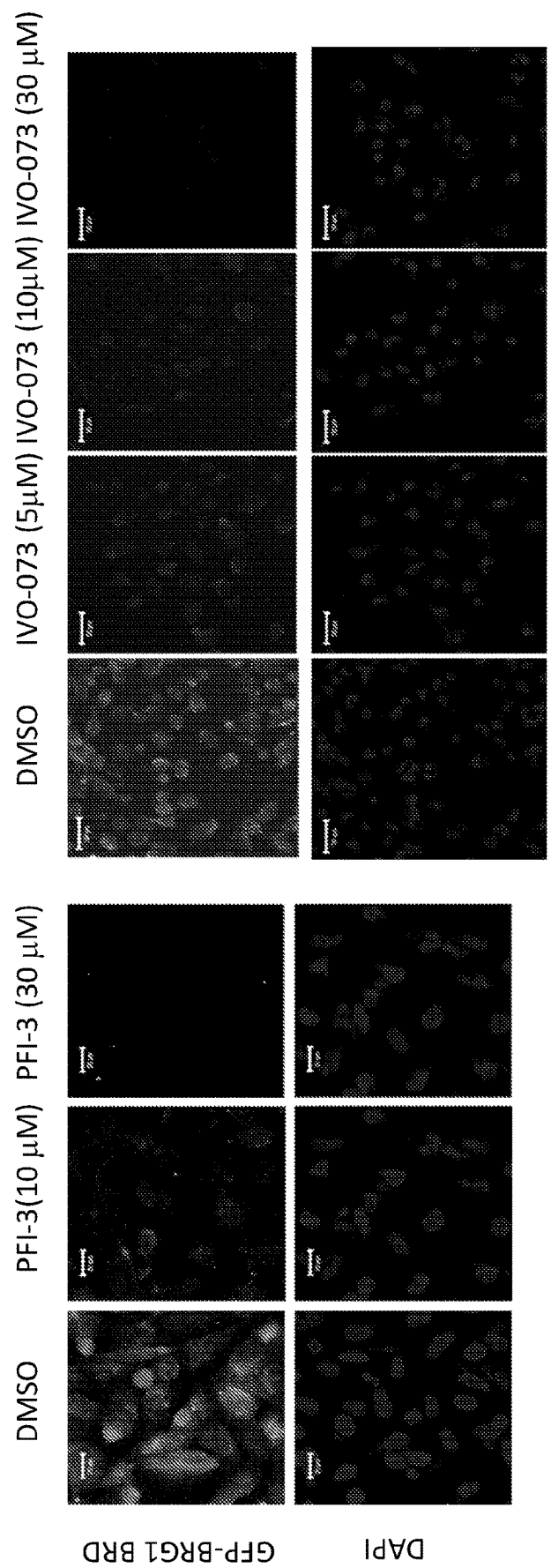
FIG. 4 is a series of fluorescence microscopy images showing the effects of Brahma-related gene-1 bromodomain inhibitors (BRIs) on the nuclear localization of a green fluorescent protein (GFP)-tagged bromodomain of Brahma-related gene-1 (GFP-BRG1 BRD). The top row shows the fluorescence from the GFP-tagged glioblastoma cells treated with dimethyl sulfoxide (DMSO) as a control, 10 or 30 micromolar (µM) PFI-3 or 5, 10, or 30 µM of the PFI-3 analog IV-073. The bottom row shows the fluorescence from 4',6-diamidino-2-phenylindole (DAPI) in the same cells.

The effects of PFI-3 and its analogs on the nuclear localization of a fluorescently tagged bromodomain of BRG1 expressed in MT330 GBM cells was studied. In the control samples, the fluorescent bromodomain is localized to the nucleus. However, an inhibitor displaces it from the nucleus and the fluorescence signal markedly decreases because it is degraded in the cytoplasm. FIG. 4 shows that PFI-3 displaces the BRG1 bromodomain from the nucleus as compared to the control (DMSO). However, at a much lower dose the IV-073 compound is more effective in displacing the bromodomain binding to the nucleus. Thus, the PFI-3 analog IV-073 is more active than PFI-3 in this assay.

Figure 5:
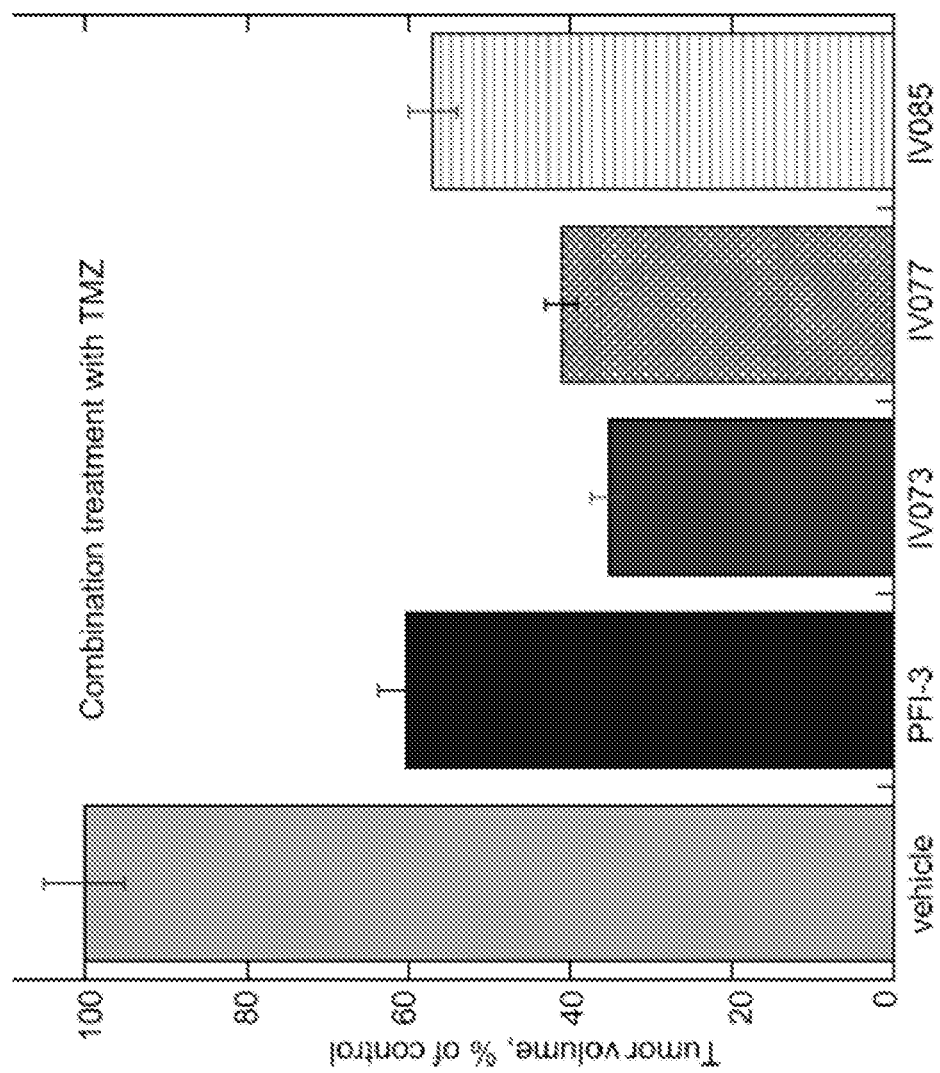
FIG. 5 is a graph showing the effect of Brahma-related gene-1 bromodomain inhibitors (BRIs), PFI-3 and the PFI-3 analogs (PAs) IV-073, IV-077, and IV-085, on the anticancer activity of temozolomide (TMZ) on brain-tumor initiating-cell (BTIC) tumor growth. BTICs ($10^6$ cells) from X16 glioblastoma were injected into the flanks of immunodeficient mice. After confirming tumor initiation by live animal imaging, mice were treated with PFI-3 or a PA (0.5 microgram per mouse (µg/mouse)) and TMZ (0.25 mg/mouse) by intrarperitoneal (IP) injection on alternate days. The reduction in tumor volume was calculated at 2 weeks post-treatment.

Several of the PAs were tested alone and in combination with TMZ after establishing X16 BTIC mouse flank xenografts for one-week (5 mice/group) and it was found that all compounds alone only slightly inhibited tumor growth (data not shown). However, combining TMZ with IV-073 or IV-085 had a marked effect on tumor growth at 2 weeks post-treatment compared with PFI-3 and TMZ. See FIG. 5. Moreover, only small tumors were detectable even after treatment for 8 weeks, while combining TMZ with PFI-3 had a less dramatic effect. In contrast, all mice with single drug treatment had to be euthanized because the tumors had reached 1000 m³ by 3 weeks post-treatment. These results provide the tantalizing prospect of novel BRIs that could have clinical utility in GBM. In particular, among the new BRIs disclosed herein, YH-IV-073 shows better efficacy in sensitizing BTICs to the DNA alkylating agent temozolomide in vitro and inhibiting the growth of subcutaneous BTIC tumors when combined with temozolomide.

Figure 6:
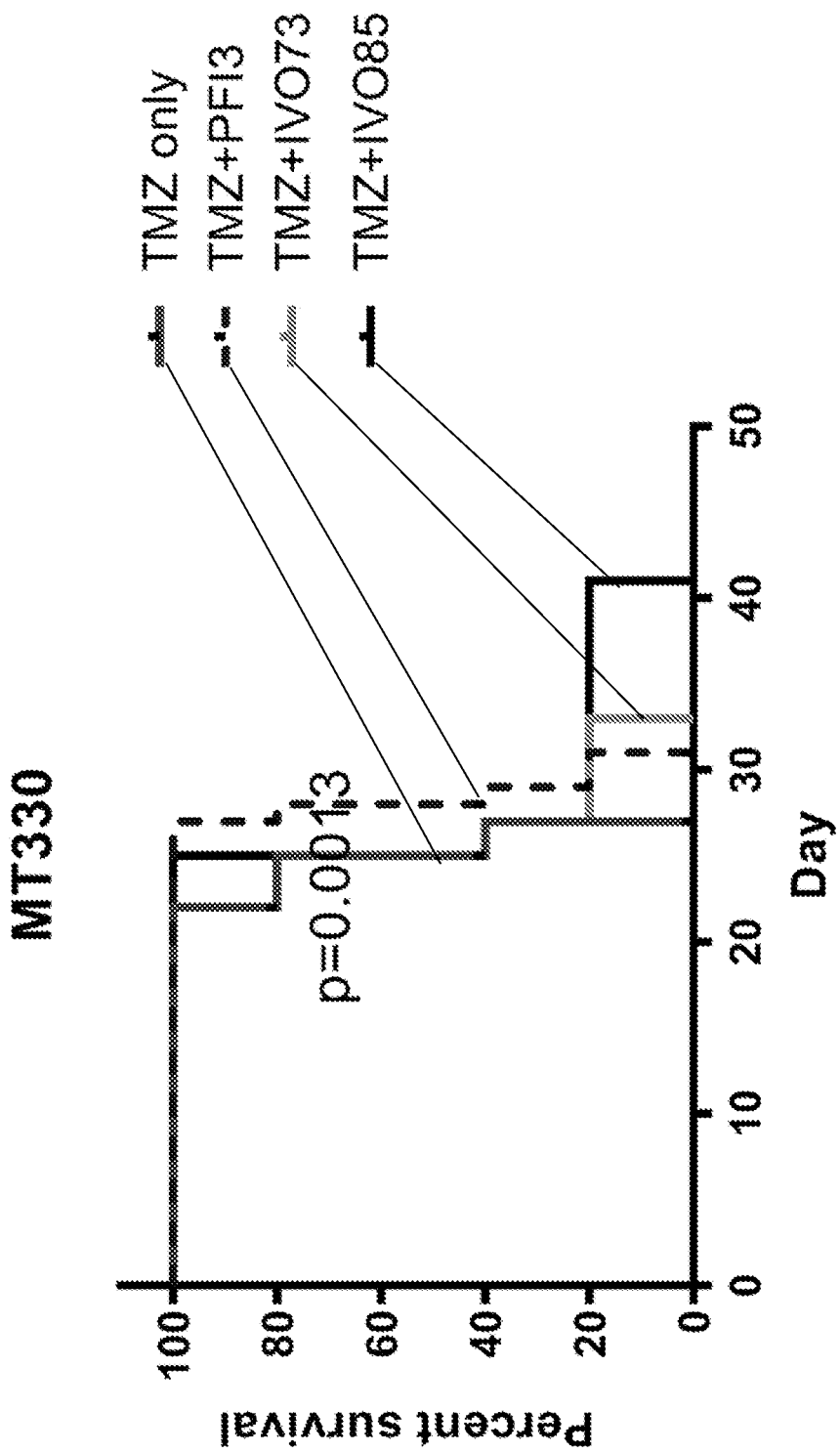
FIG. 6 is a graph showing the survival curves (percent survival versus days after treatment) of mice after intracranial injection of glioblastoma (GBM) cells and intraperitoneal injection of temozolomide (TMZ) or combinations of TMZ and a Brahma-related gene-1 bromodomain inhibitors (BRIs): PFI-3 or one of the presently disclosed PFI-3 analogs (PAs) IV-073 or IV-085. Five mice per group were treated with TMZ with or without the BRI (10 milligrams per kilogram (mg/kg) body weight.

TMZ with or without a BRI was also tested in mice after intercranial injection of GBM cells. As shown in FIG. 6, the combination of TMZ with PFI-3 or one of its analogs resulted in an enhanced animal survival, with the greatest effect observed with the combination of TMZ and IV-085.

In summary, it has been shown that PFI-3 (YH-IV-081) and new analogs thereof (YH-IV-73, YH-IV-77, and YH-IV-085) do not cause GBM cell death when used alone. However, PFI-3 or its analogs are capable of sensitizing GBM cells to DNA alkylation by TMZ which leads to cell death, even in cells that are resistant to DNA alkylation agents, such as TMZ.

Example 3

Synthesis of Additional BRIs

Scheme 5. Synthesis of YH-IV-125 and YH-IV-137.

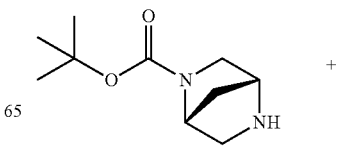

-continued

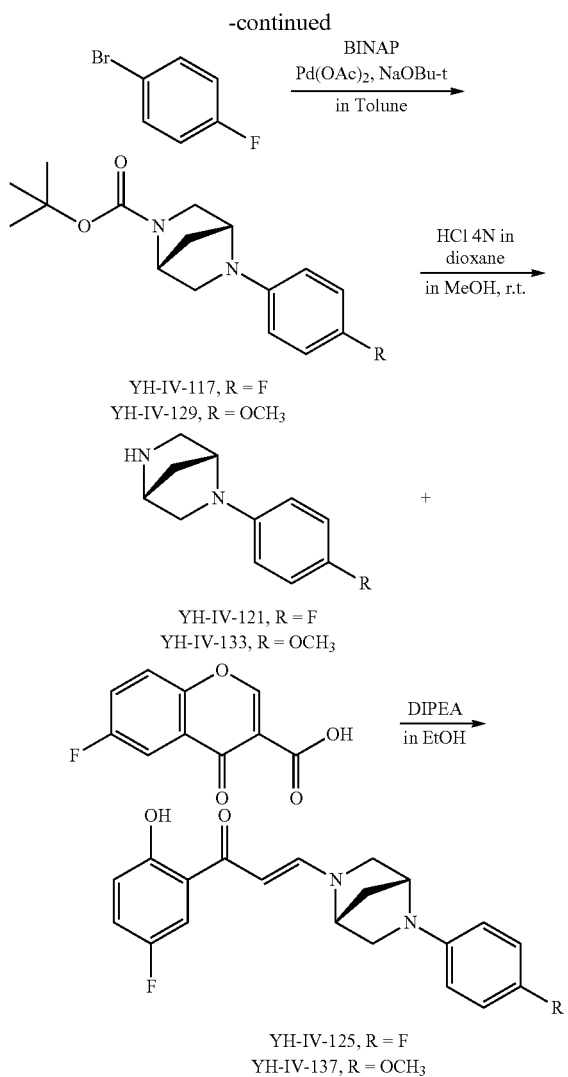

YH-IV-117, R = F
YH-IV-129, R = OCH₃

YH-IV-121, R = F
YH-IV-133, R = OCH₃

YH-IV-125, R = F
YH-IV-137, R = OCH₃

(1R,4R)-tert-butyl 5-(4-fluorophenyl)-2,5-diazabicyclo[2.2.1]heptane-2-carboxylate (C₁₆H₂₁FN₂O₂) (YH-IV-117)

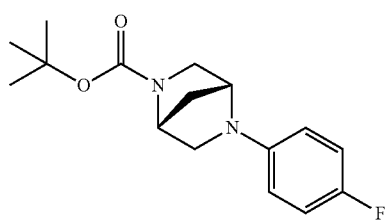 [SMILES: CC(C)(C)OC(=O)N1C[C@H]2C[C@@H]1CN2c1ccc(F)cc1]

As shown in Scheme 5, to a mixture of (1R,4R)-tert-butyl 2,5-diazabicyclo[2.2.1]heptane-2-carboxylate (2.00 g, 0.010088 mol) in anhydrous tolune (50 mL) was added 1-bromo-4-fluorobenzene (3.53 g, 0.020176 mol), KOBu-t (1.36 g, 0.012105 mol), Pd(OAc)₂ (0.113 g, 0.005044 mol), and (R)-(+)-2,2'-bis(diphenylphosphino)-1,1'-binaphthalene (BINAP, 0.314 g, 0.005044 mol) at room temperature under the argon atmosphere. The resulting reaction mixture was heated at reflux for 12 hours under argon. After the end of the reaction was established by TLC, the reaction was quenched by water, extracted with ethyl acetate. The organic layer was dried with MgSO₄, filtered, and concentrated under vacuum. The product was purified by a silica gel column using DCM and ethyl acetate (19:1) as eluent to afford 1.00 g (33.9%) of the desired compound as white solid.

¹HNMR (400 MHz, dmso-d₆) δ 7.02-6.97 (m, 2H, ArH), 6.61-6.56 (m, 2H, ArH), 4.46-4.37 (m, 2H, CH), 3.55-3.50 (m, 1H, CH), 3.31-3.24 (m, 1H, CH), 3.20-3.16 (m, 1H, CH), 2.93-2.88 (m, 1H, CH), 1.91-1.84 (m, 2H, CH), 1.39 (s, 6H, 2×CH₃), 1.32 (s, 3H, CH₃).

Mass (ESI, Negative): [M−H]⁻; (ESI, Positive): [M+Na]⁺.
HRMS [C₁₆H₂₂FN₂O₂⁺]: calcd 293.1665, found [M+H]⁺.
Purity: 96.93% (HPLC).

(1R,4R)-2-(4-fluorophenyl)-2,5-diazabicyclo[2.2.1]heptane (C₁₁H₁₃FN₂) (YH-IV-121)

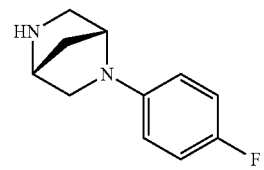 [SMILES: Fc1ccc(N2C[C@H]3C[C@@H]2CN3)cc1]

Continuing with Scheme 5, to a solution of (1R,4R)-tert-butyl 5-(4-fluorophenyl)-2,5-diazabicyclo[2.2.1]heptane-2-carboxylate (0.48 g, 0.001642 mol) in methanol (10 mL), which was cooled in an ice water bath under an argon atmosphere, was added 4N HCl in dioxane (3.70 mL, 0.014777 mol). The resulting reaction mixture was allowed to stir 2-3 hours at room temperature under argon. After the end of the reaction was established by TLC, the reaction was concentrated under vacuum to afford 040 g as yellowish solid. The product was used for the next step without further purification.

((E)-1-(5-fluoro-2-hydroxyphenyl)-3-((1R,4R)-5-(4-fluorophenyl)-2,5-diazabicyclo[2.2.1]heptan-2-yl)prop-2-en-1-one (C₂₀H₁₈F₂N₂O₂) (YH-IV-125)

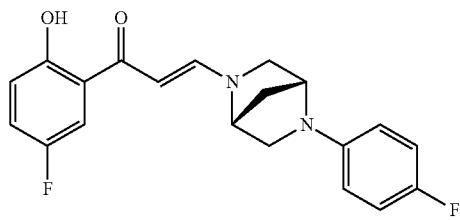 [SMILES: O=C(/C=C/N1C[C@H]2C[C@@H]1CN2c1ccc(F)cc1)c1cc(F)ccc1O]

Continuing with Scheme 5, to a solution of (1R,4R)-2-(pyridin-2-yl)-2,5-diazabicyclo[2.2.1]heptane (0.316 g, 0.001642 mol) in ethanol (10 mL) was added DIPEA (1.06 g, 0.008209 mol) at room temperature under the argon atmosphere. The reaction was stirred and was homogenous at room temperature under argon. To the reaction was added 6-fluoro-4-oxo-4H-chromene-3-carboxylic acid (0.34 g, 0.001642 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and EtOAc (19:1) as eluent to afford 0.34 g (58.1%) of the desired compound as yellow solid.

$^1$HNMR (400 MHz, dmso-d$_6$) δ 13.61 (s, 1H, OH), 8.14 (d, J=12.0 Hz, 1H, CH), 7.28-7.25 (m, 1H, ArH), 7.09-7.04 (m, 1H, ArH), 7.00-6.96 (m, 2H, ArH), 6.88-6.85 (m, 1H, ArH), 6.54-6.50 (m, 2H, ArH), 5.57 (d, J=12.0 Hz, 1H, CH), 4.53 (s, 1H, CH), 4.40 (s, 1H, CH), 3.75-3.72 (m 1H, CH), 3.46 (s, 2H, CH), 3.19-3.16 (m, 1H, CH), 2.24-2.21 (m, 1H, CH), 2.08-2.06 (m, 1H, CH).

Mass (ESI, Negative): [M–H]$^-$; (ESI, Positive): [M+H]$^+$. HRMS [C$_{20}$H$_{19}$F$_2$N$_2$O$_2^+$]: calcd 357.1415, found [M+H]$^+$.

(1R,4R)-tert-butyl 5-(4-methoxyphenyl)-2,5-diazabicyclo[2.2.1]heptane-2-carboxylate (C$_{17}$H$_{24}$N$_2$O$_3$) (YH-IV-129)

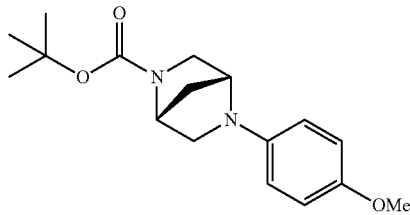 [SMILES: COc1ccc(N2C[C@H]3C[C@@H]2CN3C(=O)OC(C)(C)C)cc1]

As shown in Scheme 5, above, to a mixture of (1R,4R)-tert-butyl 2,5-diazabicyclo[2.2.1]heptane-2-carboxylate (2.00 g, 0.010088 mol) in anhydrous tolune (50 mL) was added 1-bromo-4-methoxybenzene (3.77 g, 0.020176 mol), KOBu-t (1.70 g, 0.0151316 mol), Pd(OAc)$_2$ (0.113 g, 0.005044 mol), and (R)-(+)-2,2'-bis(diphenylphosphino)-1,1'-binaphthalene (BINAP, 0.314 g, 0.005044 mol) at room temperature under the argon atmosphere. The resulting reaction mixture was heated at reflux for 3 hours under argon. After the end of the reaction was established by TLC, the reaction was quenched by water, extracted with ethyl acetate. The organic layer was dried with MgSO$_4$, filtered, and concentrated under vacuum. The product was purified by a silica gel column using hexanes and ethyl acetate (2:1) as eluent to afford 1.76 g (57.3%) of the desired compound as pinkish solid.

$^1$HNMR (400 MHz, cdcl$_3$) δ 6.86-6.82 (m, 2H, ArH), 6.54-6.50 (m, 2H, ArH), 4.60-4.46 (br s, 1H, CH), 4.31 (br s, 1H, CH), 3.76 (s, 3H, CH$_3$O), 3.58-3.50 (m, 1H, CH), 3.43-3.32 (m, 2H, CH), 3.16-3.04 (m, 1H, CH), 1.98-1.86 (m, 2H, CH), 1.44 (s, 3H, CH$_3$), 1.39 (s, 6H, 2×CH$_3$).

Mass (ESI, Negative): [M–H]$^-$; (ESI, Positive): [M+Na]$^+$. HRMS [C$_{21}$H$_{22}$FN$_2$O$_3^+$]: calcd 369.1614, found [M+H]$^+$.

(1R,4R)-2-(4-methoxyphenyl)-2,5-diazabicyclo[2.2.1]heptane (C$_{12}$H$_{16}$N$_2$O) (YH-IV-133)

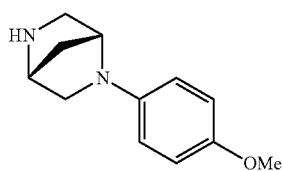 [SMILES: COc1ccc(N2C[C@H]3C[C@@H]2CN3)cc1]

As shown in Scheme 5, above, to a solution of (1R,4R)-tert-butyl 5-(4-methoxyphenyl)-2,5-diazabicyclo[2.2.1]heptane-2-carboxylate (0.50 g, 0.0016427 mol) in methanol (10 mL), which was cooled in an ice water bath under an argon atmosphere, was added 4N HCl in dioxane (3.70 mL, 0.014777 mol). The resulting reaction mixture was allowed to stir 2-3 hours at room temperature under argon. After the end of the reaction was established by TLC, the reaction was concentrated under vacuum to afford 041 g as yellowish solid. The product was used for the next step without further purification.

(E)-1-(5-fluoro-2-hydroxyphenyl)-3-((1R,4R)-5-(4-methoxyphenyl)-2,5-diazabicyclo[2.2.1]heptan-2-yl) prop-2-en-1-one (C$_{21}$H$_{21}$FN$_2$O$_3$) (YH-IV-137)

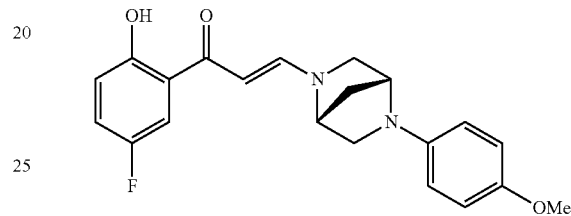

As shown in Scheme 5, above, to a solution of (1R,4R)-2-(4-methoxyphenyl)-2,5-diazabicyclo[2.2.1]heptane (0.336 g, 0.0016427 mol) in ethanol (10 mL) was added DIPEA (1.06 g, 0.008209 mol) at room temperature under the argon atmosphere. The reaction was stirred and was homogenous at room temperature under argon. To the reaction was added 6-fluoro-4-oxo-4H-chromene-3-carboxylic acid (0.312 g, 0.0016427 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using hexanes and EtOAc (2:1 to 1:1) as eluent to afford 0.35 g (58.3%) of the desired compound as yellow solid.

$^1$HNMR (400 MHz, cdcl$_3$) δ 13.59 (s, 1H, OH), 8.14 (d, J=12.0 Hz, 1H, CH), 7.27-7.24 (m, 1H, ArH), 7.08-7.03 (m, 1H, ArH), 6.88-6.84 (m, 3H, ArH), 6.56-6.51 (m, 2H, ArH), 5.57 (d, J=12.0 Hz, 1H, CH), 4.51 (s, 1H, CH), 4.36 (s, 1H, CH), 3.76 (s, 3H, CH$_3$O), 3.74-3.71 (m 1H, CH), 3.50-3.42 (m, 2H, CH), 3.16-3.14 (m, 1H, CH), 2.22-2.20 (m, 1H, CH), 2.05-2.02 (m, 1H, CH).

Mass (ESI, Negative): [M–H]$^-$; (ESI, Positive): [M+H]$^+$. HRMS [C$_{21}$H$_{22}$FN$_2$O$_3^+$]: calcd 369.1614, found [M+H]$^+$.

Scheme 6. Synthesis of YH-IV-141 and YH-IV-145.

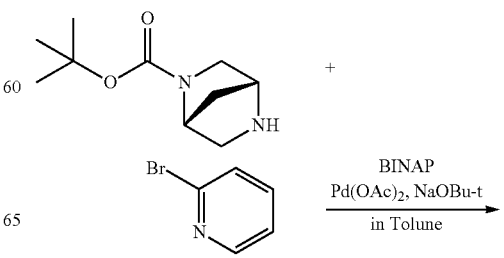

-continued

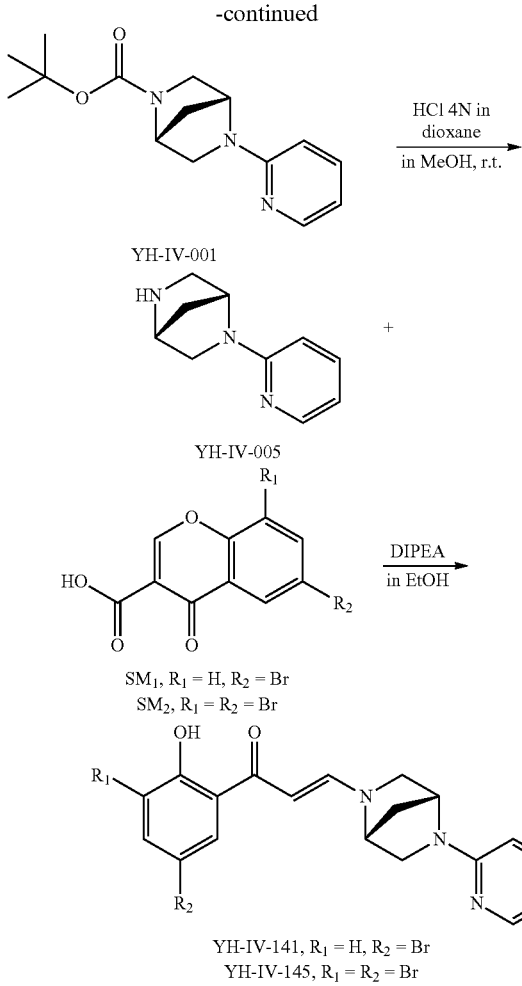

(1R,4R)-tert-butyl 5-(pyridin-2-yl)-2,5-diazabicyclo[2.2.1]heptane-2-carboxylate ($C_{15}H_{21}N_3O_2$) (YH-IV-001)

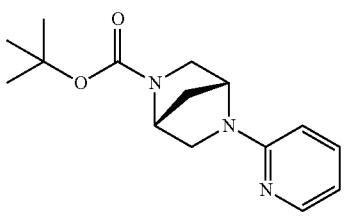 [SMILES: CC(C)(C)OC(=O)N1C[C@H]2C[C@@H]1CN2c1ccccn1]

As shown in Scheme 6, above, to a mixture of (1R,4R)-tert-butyl 2,5-diazabicyclo[2.2.1]heptane-2-carboxylate (1.00 g, 0.005035 mol) in anhydrous tolune (30 mL) was added 2-bromopyridine (1.59 g, 0.01007 mol), NaOBu-t (0.485 g, 0.005035 mol), Pd(OAc)$_2$ (57 mg, 0.0002522 mol), and (R)-(+)-2,2'-bis(diphenylphosphino)-1,1'-binaphthalene (BINAP, 0.157 g, 0.0002522 mol) at room temperature under the argon atmosphere. After the end of the reaction was established by TLC, the reaction was quenched by water, extracted with ethyl acetate. The organic layer was dried with MgSO$_4$, filtered, and concentrated under vacuum. The product was purified by a silica gel column using hexanes and ethyl acetate (1:1) as eluent to afford 0.96 g (70%) of the desired compound as yellowish solid.

$^1$HNMR (400 MHz, DMSO-d$_6$) δ 8.06 (d, J=4.8 Hz, 1H, ArH), 7.51-7.47 (m, 1H, ArH), 6.60-6.57 (m, 1H, ArH), 6.54-6.51 (m, 1H, ArH), 4.77 (d, J=8.8 Hz, 1H, CH), 3.51-3.45 (m, 1H, CH), 3.44-3.30 (m, 2H, CH), 3.26-3.33 (m, 1H, CH), 3.18-3.15 (m, 1H, CH), 1.90-1.87 (m, 2H, CH), 1.39 (s, 6H, 2×CH$_3$), 1.34 (s, 3H, CH$_3$).

Mass (ESI, Negative): [M−H]$^-$; (ESI, Positive): [M+Na]$^+$.
HRMS [$C_{15}H_{22}N_3O_2^+$]: calcd 276.1712, found [M+H]$^+$.

(1R,4R)-2-(pyridin-2-yl)-2,5-diazabicyclo[2.2.1]heptane ($C_{10}H_{13}N_3$) (YH-IV-005)

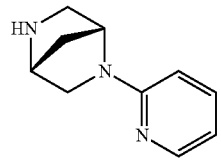 [SMILES: c1ccc(N2C[C@H]3C[C@@H]2CN3)nc1]

Continuing with Scheme 6, to a solution of (1R,4R)-tert-butyl 5-(pyridin-2-yl)-2,5-diazabicyclo-[2.2.1]heptane-2-carboxylate (0.62 g, 0.0022517 mol) in methanol (10 mL), which was cooled in an ice water bath under an argon atmosphere, was added 2N HCl in Et$_2$O (10 mL, 0.020265 mol). The resulting reaction mixture was allowed to stir 30 minutes at room temperature under argon. After the end of the reaction was established by TLC, the reaction was concentrated under vacuum to afford 0.60 g as yellowish solid. The product was used for the next step without further purification.

$^1$HNMR (400 MHz, DMSO-d$_6$) δ 8.13 (d, J=4.8 Hz, 1H, ArH), 7.48-7.43 (m, 1H, ArH), 6.63-6.58 (m, 1H, ArH), 6.37-6.32 (m, 1H, ArH), 5.03 (d, J=7.8 Hz, 1H, CH), 4.54-4.50 (m, 1H, CH), 3.68-3.65 (m, 1H, CH), 3.61-3.49 (m, 2H, CH), 3.44-3.38 (m, 1H, CH), 2.12-1.91 (m, 2H, CH).

Mass (ESI, Negative): [M−H]$^-$; (ESI, Positive): 176.06 [M+H]$^+$; 198.09 [M+Na]$^+$.
HRMS [$C_{10}H_{14}N_3^+$]: calcd 176.1188, found [M+H]$^+$.

(E)-1-(5-bromo-2-hydroxyphenyl)-3-((1R,4R)-5-(pyridin-2-yl)-2,5-diazabicyclo[2.2.1]heptan-2-yl)prop-2-en-1-one ($C_{19}H_{18}BrN_3O_2$) (YH-IV-141)

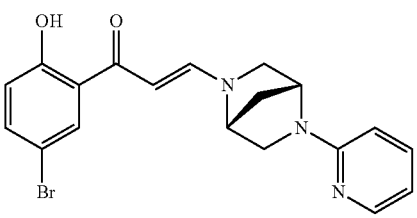 [SMILES: O=C(/C=C/N1C[C@H]2C[C@@H]1CN2c1ccccn1)c1cc(Br)ccc1O]

Continuing with Scheme 6, to a solution of (1R,4R)-2-(pyridin-2-yl)-2,5-diazabicyclo[2.2.1]heptane (0.175 g, 0.0010 mol) in ethanol (10 mL) was added DIPEA (0.65 g, 0.0050 mol) at room temperature under the argon atmosphere. The reaction was stirred and was homogenous at room temperature under argon. To the reaction was added 6-bromo-4-oxo-4H-chromene-3-carboxylic acid (0.27 g, 0.0010 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and methanol (19:1) as eluent to afford 0.36 g (90%) of the desired compound as yellow solid.

$^1$HNMR (400 MHz, dmso-d$_6$) δ 14.67 (s, 1H, OH), 8.30 (d, J=12.0 Hz, 1H, CH), 8.10-8.07 (m, 2H, ArH), 7.55-7.49 (m, 1H, ArH), 7.48 (dd, J=8.8 Hz, J=2.4 Hz, 1H, ArH), 6.78 (d, J=8.8 Hz, 1H, ArH), 6.64-6.59 (m, 1H, ArH), 6.57 (d, J=8.2 Hz, 1H, ArH), 5.90 (d, J=12.0 Hz, 1H, CH), 4.95 (s, 1H, CH), 4.82 (s, 1H, CH), 3.62-3.60 (m 1H, CH), 3.54-3.42 (m, 2H, CH), 3.35-3.33 (m, 1H, CH), 2.11-2.07 (m, 1H, CH), 2.04-1.99 (m, 1H, CH).

Mass (ESI, Negative): [M–H]$^-$; (ESI, Positive): [M+H]$^+$.

HRMS [C$_{19}$H$_{19}$BrN$_3$O$_2^+$]: calcd 400.0661, found [M+H]$^+$.

(E)-1-(3,5-dibromo-2-hydroxyphenyl)-3-((1R,4R)-5-(pyridin-2-yl)-2,5-diazabicyclo[2.2.1]heptan-2-yl) prop-2-en-1-one (C$_{19}$H$_{17}$Br$_2$N$_3$O$_2$) (YH-IV-145)

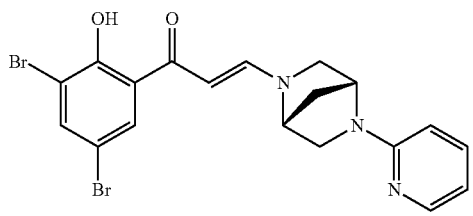 [SMILES: O=C(/C=C/N1C[C@H]2C[C@@H]1CN2c1ccccn1)c1cc(Br)cc(Br)c1O]

As shown in Scheme 6, above, to a solution of (1R,4R)-2-(pyridin-2-yl)-2,5-diazabicyclo[2.2.1]heptane (0.175 g, 0.0010 mol) in ethanol (10 mL) was added DIPEA (0.65 g, 0.0050 mol) at room temperature under the argon atmosphere. The reaction was stirred and was homogenous at room temperature under argon. To the reaction was added 6,8-dibromo-4-oxo-4H-chromene-3-carboxylic acid (0.35 g, 0.0010 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and methanol (19:1) as eluent to afford 0.14 g (29.2%) of the desired compound as brown solid.

$^1$HNMR (400 MHz, dmso-d$_6$) δ 16.03 (s, 1H, OH), 8.38 (d, J=12.0 Hz, 1H, CH), 8.15 (d, J=2.4 Hz, 1H, ArH), 8.10-8.08 (m, 1H, ArH), 7.58 (d, J=3.2 Hz, 1H, ArH), 7.55-7.51 (m, 1H, ArH), 6.64-6.61 (m, 1H, ArH), 6.57-6.55 (m, 1H, ArH), 5.96 (d, J=12.0 Hz, 1H, CH), 4.97 (s, 1H, CH), 4.85 (s, 1H, CH), 3.63-3.61 (m 1H, CH), 3.57-3.45 (m, 2H, CH), 3.35-3.32 (m, 1H, CH), 2.11-2.08 (m, 1H, CH), 2.05-1.99 (m, 1H, CH).

Mass (ESI, Negative): [M–H]$^-$; (ESI, Positive): [M+H]$^+$.

HRMS [C$_{19}$H$_{18}$Br$_2$N$_3$O$_2^+$]: calcd 477.9766, found [M+H]$^+$.

Scheme 7. Synthesis of YH-IV-149 and YH-IV-153.

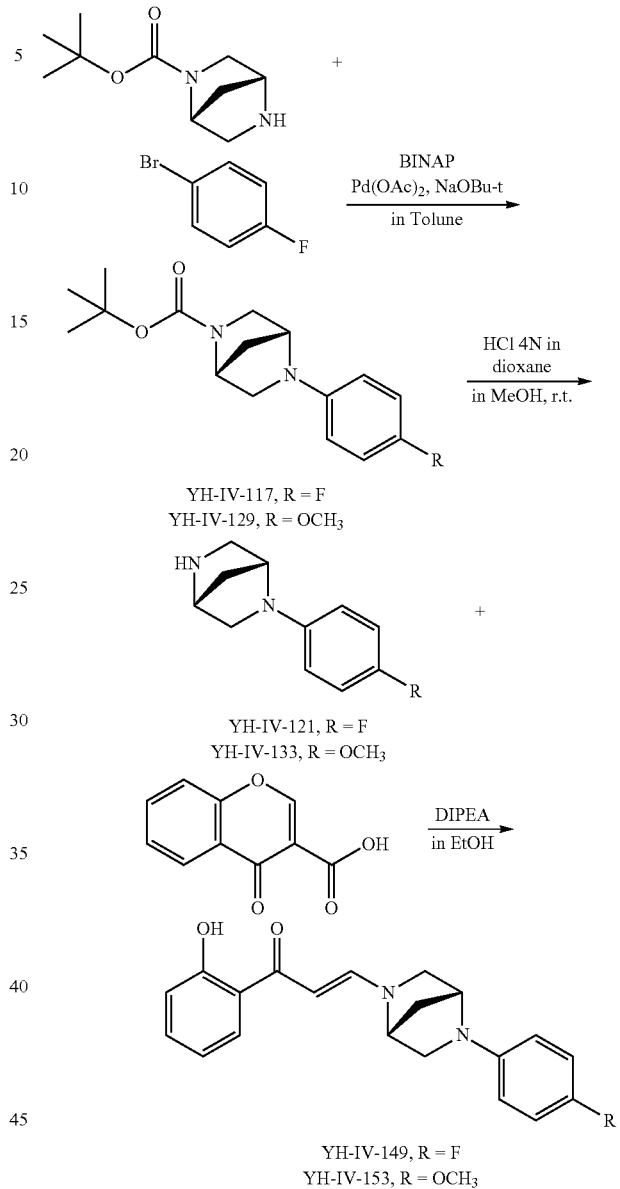

YH-IV-117, R = F
YH-IV-129, R = OCH$_3$

YH-IV-121, R = F
YH-IV-133, R = OCH$_3$

YH-IV-149, R = F
YH-IV-153, R = OCH$_3$ (E)-3-((1R,4R)-5-(4-fluorophenyl)-2,5-diazabicyclo [2.2.1]heptan-2-yl)-1-(2-hydroxyphenyl)prop-2-en-1-one (C$_{20}$H$_{19}$FN$_2$O$_2$) (YH-IV-149)

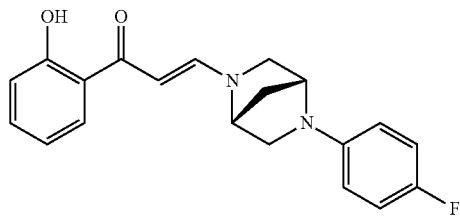 [SMILES: O=C(/C=C/N1C[C@H]2C[C@@H]1CN2c1ccc(F)cc1)c1ccccc1O]

As shown in Scheme 7, above, to a solution of (1R,4R)-2-(4-fluorophenyl)-2,5-diazabicyclo[2.2.1]heptane (0.316 g, 0.001642 mol) in ethanol (10 mL) was added DIPEA (1.06 g, 0.008209 mol) at room temperature under the argon atmosphere. The reaction was stirred and was homogenous at room temperature under argon. To the reaction was added 4-oxo-4H-chromene-3-carboxylic acid (0.312 g, 0.001642 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and EtOAc (19:1) as eluent to afford 0.324 g (58.3%) of the desired compound as yellow solid.

$^1$HNMR (400 MHz, dmso-d$_6$) δ 13.80 (s, 1H, OH), 8.13 (d, J=12.0 Hz, 1H, CH), 7.62 (d, J=8.0 Hz, 1H, ArH), 7.34 (t, J=8.0 Hz, 1H, ArH), 6.99-6.91 (m, 3H, ArH), 6.80-6.76 (m, 1H, ArH), 6.53-6.50 (m, 2H, ArH), 5.69 (d, J=12.0 Hz, 1H, CH), 4.52 (s, 1H, CH), 4.38 (s, 1H, CH), 3.73-3.71 (m 1H, CH), 3.45 (s, 2H, CH), 3.18-3.16 (m, 1H, CH), 2.22-2.20 (m, 1H, CH), 2.07-2.05 (m, 1H, CH).

Mass (ESI, Negative): [M−H]$^-$; (ESI, Positive): [M+H]$^+$.

HRMS [C$_{20}$H$_{20}$FN$_2$O$_2^+$]: calcd 339.1509, found [M+H]$^+$.

(E)-1-(2-hydroxyphenyl)-3-((1R,4R)-5-(4-methoxyphenyl)-2,5-diazabicyclo[2.2.1]heptan-2-yl)prop-2-en-1-one (C$_{21}$H$_{22}$N$_2$O$_3$) (YH-IV-153)

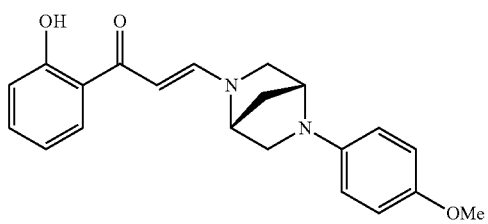 [SMILES: COc1ccc(N2C[C@H]3C[C@@H]2CN3/C=C/C(=O)c2ccccc2O)cc1]

As shown in Scheme 7, above, to a solution of (1R,4R)-2-(4-methoxyphenyl)-2,5-diazabicyclo[2.2.1]heptane (0.336 g, 0.0016427 mol) in ethanol (10 mL) was added DIPEA (1.06 g, 0.008209 mol) at room temperature under the argon atmosphere. The reaction was stirred and was homogenous at room temperature under argon. To the reaction was added 4-oxo-4H-chromene-3-carboxylic acid (0.312 g, 0.0016427 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using hexanes and EtOAc (2:1 to 1:1) as eluent to afford 0.38 g (66.0%) of the desired compound as yellow solid.

$^1$HNMR (400 MHz, cdcl$_3$) δ 12.92 (s, 1H, OH), 8.13 (d, J=12.1 Hz, 1H, CH), 7.61 (d, J=8.0 Hz, 1H, ArH), 7.33 (t, J=8.0 Hz, 1H, ArH), 6.92 (d, J=8.2 Hz, 1H, ArH), 6.88-6.84 (m, 2H, ArH), 6.77 (t, J=7.5 Hz, 1H, ArH), 6.56-6.53 (m, 2H, ArH), 5.67 (d, J=12.0 Hz, 1H, CH), 4.50 (s, 1H, CH), 4.35 (s, 1H, CH), 3.78 (s, 3H, CH$_3$O), 3.71-3.64 (m 1H, CH), 3.48-3.41 (s, 2H, CH), 3.16-3.14 (m, 1H, CH), 2.21-2.18 (m, 1H, CH), 2.05-2.02 (m, 1H, CH).

Mass (ESI, Negative): [M−H]$^-$; (ESI, Positive): [M+H]$^+$.

HRMS [C$_{21}$H$_{23}$N$_2$O$_3^+$]: calcd 351.1709, found [M+H]$^+$.

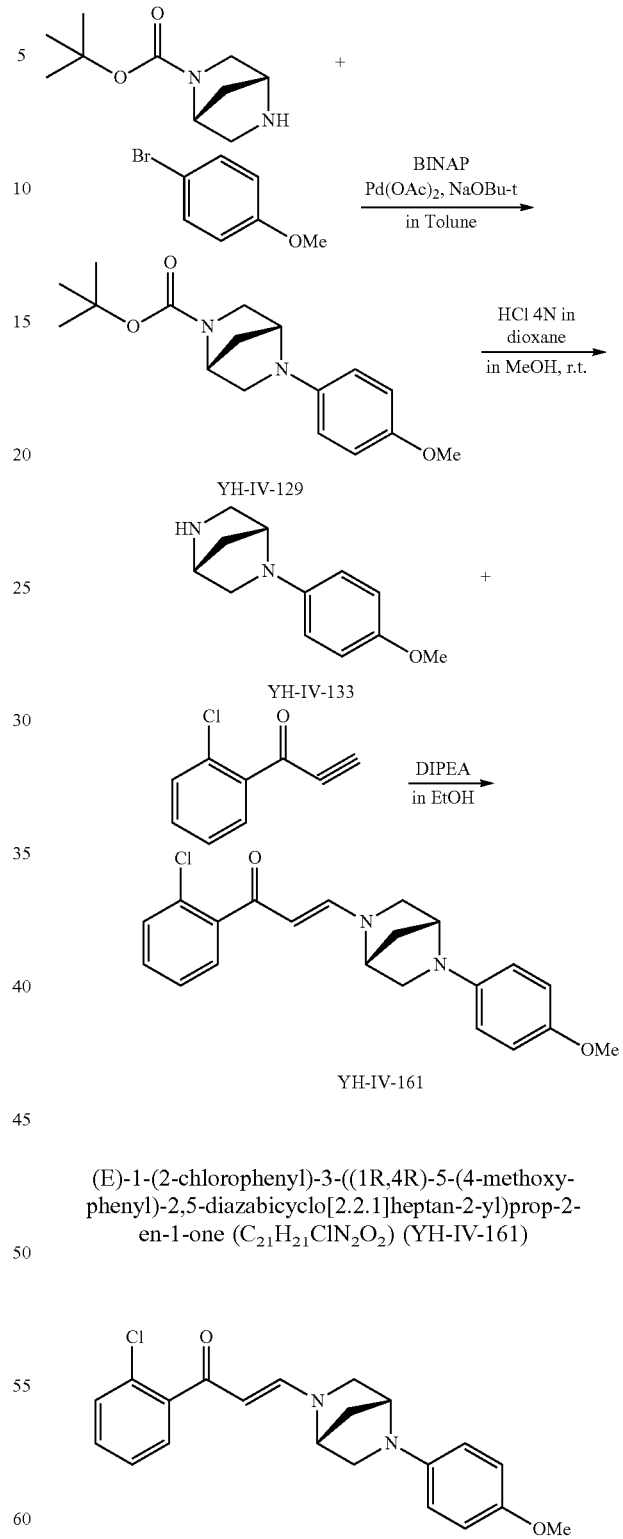

Scheme 8. Synthesis of YH-IV-161.

(E)-1-(2-chlorophenyl)-3-((1R,4R)-5-(4-methoxyphenyl)-2,5-diazabicyclo[2.2.1]heptan-2-yl)prop-2-en-1-one (C$_{21}$H$_{21}$ClN$_2$O$_2$) (YH-IV-161)

As shown in Scheme 8, above, to a solution of (1R,4R)-2-(4-methoxyphenyl)-2,5-diazabicyclo[2.2.1]heptane (0.134 g, 0.0006571 mol) in ethanol (10 mL) was added DIPEA (0.57 g, 0.0032854 mol) at room temperature under the argon atmosphere. The reaction was stirred and was homogenous at room temperature under argon. To the reaction was added 1-(2-chlorophenyl)prop-2-yn-1-one (0.108 g, 0.0006571 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and methanol (19:1) as eluent to afford 0.22 g (91.6%) of the desired compound as light brown solid.

$^1$HNMR (400 MHz, DMSO$_6$) δ 7.47-7.34 (m, 2H, ArH), 7.29-7.23 (m, 3H, C=CH and ArH), 6.86-6.83 (m, 2H, ArH), 6.53-6.51 (m, 2H, ArH), 5.25 (d, J=12.4 Hz, 1H, CH), 4.45 (s, 1H, CH), 4.23 (s, 1H, CH), 3.69-3.67 (m, 1H, CH), 3.39-3.32 (m 2H, CH), 3.13-3.11 (m, 1H, CH), 2.16 (d, J=9.2 Hz, 1H, CH), 2.00 (d, J=9.2 Hz, 1H, CH).

Mass (ESI, Negative): [M−H]$^-$; (ESI, Positive): [M+H]$^+$.
HRMS [C$_{21}$H$_{22}$ClN$_2$O$_2^+$]: calcd 369.1370, found [M+H]$^+$.

room temperature under argon. To the reaction was added 1-(2-chlorophenyl)prop-2-yn-1-one (0.282 g, 0.00171 mol), the resulting reaction mixture was allowed to stir for 12 hours under the same conditions. After the end of the reaction was established by TLC, the reaction was quenched by water, extracted with ethyl acetate. The organic layer was dried with MgSO$_4$, filtered, and concentrated under vacuum. The product was purified by a silica gel column using DCM and methanol (19:1) as eluent to afford 0.54 g (88.5%) of the desired compound as light brown solid.

$^1$HNMR (400 MHz, DMSO$_6$) δ 7.43-7.35 (m, 2H, ArH), 7.29-7.23 (m, 3H, C=CH and ArH), 6.98-6.93 (m, 2H, ArH), 6.50-6.47 (m, 2H, ArH), 5.27 (d, J=12.8 Hz, 1H, CH), 4.47 (s, 1H, CH), 4.26 (s, 1H, CH), 3.68-3.61 (m, 1H, CH), 3.38-3.32 (m 2H, CH), 3.14-3.12 (m, 1H, CH), 2.16 (d, J=9.2 Hz, 1H, CH), 2.03 (d, J=9.2 Hz, 1H, CH).

Mass (ESI, Negative): [M−H]$^-$; (ESI, Positive): [M+H]$^+$.
HRMS [C$_{20}$H$_{19}$ClN$_2$O$^+$]: calcd 357.1170, found [M+H]$^+$.

Scheme 9. Synthesis of YH-IV-165 and YH-IV-173.

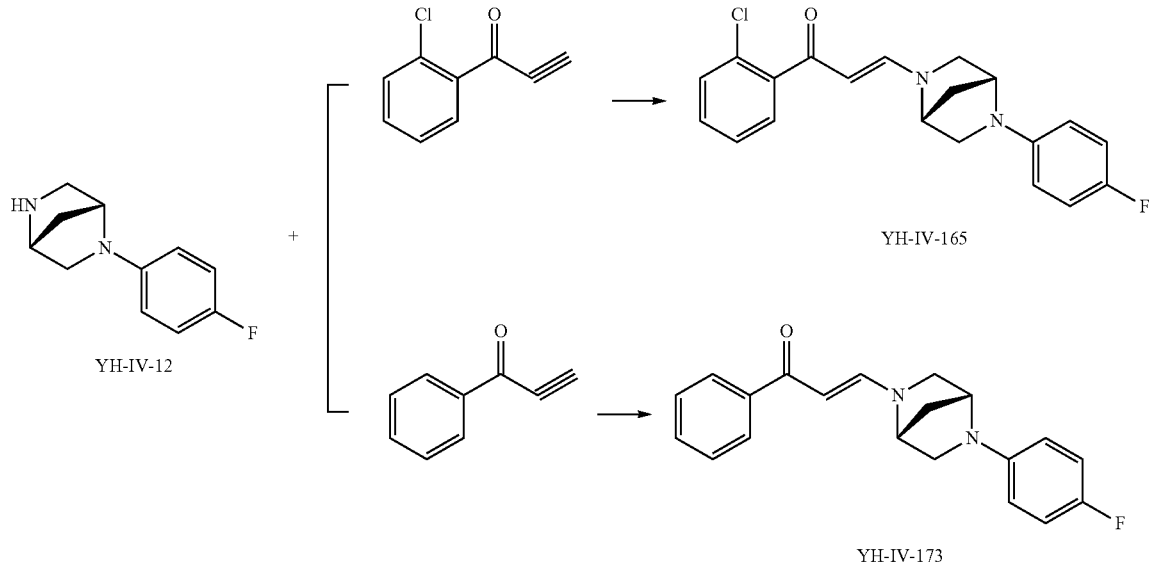

(E)-1-(2-chlorophenyl)-3-((1R,4R)-5-(4-fluorophenyl)-2,5-diazabicyclo[2.2.1]heptan-2-yl)prop-2-en-1-one (C$_{20}$H$_{18}$ClFN$_2$O) (YH-IV-165)

(E)-3-((1R,4R)-5-(4-fluorophenyl)-2,5-diazabicyclo[2.2.1]heptan-2-yl)-1-phenylprop-2-en-1-one (C$_{20}$H$_{19}$FN$_2$O) (YH-IV-173)

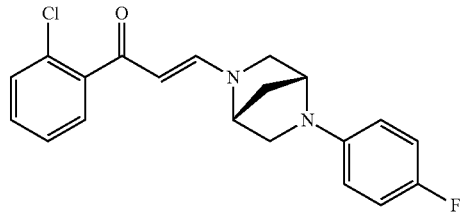
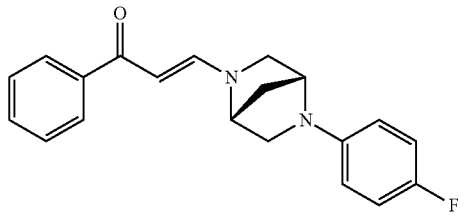 [SMILES: O=C(/C=C/N1C[C@H]2C[C@@H]1CN2c1ccc(F)cc1)c1ccccc1]

As shown in Scheme 9, above, to a solution of (1R,4R)-2-(4-fluorophenyl)-2,5-diazabicyclo[2.2.1]heptane (0.33 g, 0.00171 mol) in ethanol (15 mL) was added DIPEA (1.10 g, 0.00855 mol) at room temperature under the argon atmosphere. The reaction was stirred and was homogenous at As shown in Scheme 9, above, to a solution of (1R,4R)-2-(4-fluorophenyl)-2,5-diazabicyclo[2.2.1]heptane (0.33 g, 0.00171 mol) in ethanol (15 mL) was added DIPEA (1.10 g, 0.00855 mol) at room temperature under the argon atmosphere. The reaction was stirred and was homogenous at room temperature under argon. To the reaction was added 1-phenylprop-2-yn-1-one (0.223 mg, 0.00171 mol), the resulting reaction mixture was allowed to stir for 12 hours under the same conditions. After the end of the reaction was established by TLC, the reaction was quenched by water, extracted with ethyl acetate. The organic layer was dried with $MgSO_4$, filtered, and concentrated under vacuum. The product was purified by a silica gel column using DCM and methanol (19:1) as eluent to afford 0.39 g (71.3%) of the desired compound as light brown solid.

$^1$HNMR (400 MHz, $DMSO_6$) δ 8.05 (d, J=12.4 Hz, 1H, CH=C), 7.86-7.83 (m, 2H, ArH), 7.47-7.37 (m, 3H, C=CH and ArH), 6.98-6.93 (m, 2H, ArH), 6.51-6.48 (m, 2H, ArH), 5.64 (d, J=12.4 Hz, 1H, C=CH), 4.48 (s, 1H, CH), 4.34 (s, 1H, CH), 3.70-3.62 (m, 1H, CH), 3.40-3.36 (m 2H, CH), 3.17-3.14 (m, 1H, CH), 2.18 (d, J=8.8 Hz, 1H, CH), 2.05 (d, J=8.8 Hz, 1H, CH).

Mass (ESI, Negative): $[M-H]^-$; (ESI, Positive): $[M+H]^+$. HRMS $[C_{20}H_{20}FN_2O^+]$: calcd 323.1560, found $[M+H]^+$.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

1 Surawicz, T. S., Davis, F., Freels, S., Laws, E. R., Jr. & Menck, H. R. Brain tumor survival: results from the National Cancer Data Base. *Journal of neuro-oncology* 40, 151-160 (1998).

2 Ganguly, D., Sims, M., Cai, C., Fan, M. & Pfeffer, L. M. Chromatin Remodeling Factor BRG1 Regulates Stemness and Chemosensitivity of Glioma Initiating Cells. *Stem Cells* 36, 1804-1815, doi:10.1002/stem.2909 (2018).

3 Verhaak, R. G., Hoadley, K. A., Purdom, E., Wang, V., Qi, Y., Wilkerson, M. D., Miller, C. R., Ding, L., Golub, T., Mesirov, J. P., Alexe, G., Lawrence, M., O'Kelly, M., Tamayo, P., Weir, B. A., Gabriel, S., Winckler, W., Gupta, S., Jakkula, L., Feiler, H. S., Hodgson, J. G., James, C. D., Sarkaria, J. N., Brennan, C., Kahn, A., Spellman, P. T., Wilson, R. K., Speed, T. P., Gray, J. W., Meyerson, M., Getz, G., Perou, C. M., Hayes, D. N. & Cancer Genome Atlas Research, N. Integrated genomic analysis identifies clinically relevant subtypes of glioblastoma characterized by abnormalities in PDGFRA, IDH1, EGFR, and NF1. *Cancer Cell* 17, 98-110, doi:10.1016/j.ccr.2009.12.020 (2010).

4 Patel, A. P., Tirosh, I., Trombetta, J. J., Shalek, A. K., Gillespie, S. M., Wakimoto, H., Cahill, D. P., Nahed, B. V., Curry, W. T., Martuza, R. L., Louis, D. N., Rozenblatt-Rosen, O., Suva, M. L., Regev, A. & Bernstein, B. E. Single-cell RNA-seq highlights intratumoral heterogeneity in primary glioblastoma. *Science* 344, 1396-1401, doi:10.1126/science.1254257 (2014).

5 Brennan, C. W., Verhaak, R. G., McKenna, A., Campos, B., Noushmehr, H., Salama, S. R., Zheng, S., Chakravarty, D., Sanborn, J. Z., Berman, S. H., Beroukhim, R., Bernard, B., Wu, C. J., Genovese, G., Shmulevich, I., Barnholtz-Sloan, J., Zou, L., Vegesna, R., Shukla, S. A., Ciriello, G., Yung, W. K., Zhang, W., Sougnez, C., Mikkelsen, T., Aldape, K., Bigner, D. D., Van Meir, E. G., Prados, M., Sloan, A., Black, K. L., Eschbacher, J., Finocchiaro, G., Friedman, W., Andrews, D. W., Guha, A., Iacocca, M., O'Neill, B. P., Foltz, G., Myers, J., Weisenberger, D. J., Penny, R., Kucherlapati, R., Perou, C. M., Hayes, D. N., Gibbs, R., Marra, M., Mills, G. B., Lander, E., Spellman, P., Wilson, R., Sander, C., Weinstein, J., Meyerson, M., Gabriel, S., Laird, P. W., Haussler, D., Getz, G., Chin, L. & Network, T. R. The somatic genomic landscape of glioblastoma. *Cell* 155, 462-477, doi:10.1016/j.cell.2013.09.034 (2013).

6 Cancer Genome Atlas Research, N. Comprehensive genomic characterization defines human glioblastoma genes and core pathways. *Nature* 455, 1061-1068, doi:10.1038/nature07385 (2008).

7 Wong, A. J., Ruppert, J. M., Bigner, S. H., Grzeschik, C. H., Humphrey, P. A., Bigner, D. S. & Vogelstein, B. Structural alterations of the epidermal growth factor receptor gene in human gliomas. *Proc Natl Acad Sci USA* 89, 2965-2969 (1992).

8 Saikali, S., Avril, T., Collet, B., Hamlat, A., Bansard, J. Y., Drenou, B., Guegan, Y. & Quillien, V. Expression of nine tumour antigens in a series of human glioblastoma multiforme: interest of EGFRvIII, IL-13Ralpha2, gp100 and TRP-2 for immunotherapy. *Journal of neuro-oncology* 81, 139-148, doi:10.1007/s11060-006-9220-3 (2007).

9 Garner, J. M., Ellison, D. W., Finkelstein, D., Ganguly, D., Du, Z., Sims, M., Yang, C. H., Interiano, R. B., Davidoff, A. M. & Pfeffer, L. M. Molecular heterogeneity in a patient-derived glioblastoma xenoline is regulated by different cancer stem cell populations. *PLoS One* 10, e0125838, doi:10.1371/journal.pone.0125838 (2015).

10 Garner, J. M., Fan, M., Yang, C. H., Du, Z., Sims, M., Davidoff, A. M. & Pfeffer, L. M. Constitutive Activation of Signal Transducer and Activator of Transcription 3 (STAT3) and Nuclear Factor kappaB Signaling in Glioblastoma Cancer Stem Cells Regulates the Notch Pathway. *J Biol Chem* 288, 26167-26176, doi:10.1074/jbc.M113.477950 (2013).

11 Ganguly, D., Fan, M., Yang, C. H., Zbytek, B., Finkelstein, D., Roussel, M. F. & Pfeffer, L. M. The critical role that STAT3 plays in glioma-initiating cells: STAT3 addiction in glioma. *Oncotarget* 9, 22095-22112, doi:10.18632/oncotarget.25188 (2018).

12 Clarke, M. F., Dick, J. E., Dirks, P. B., Eaves, C. J., Jamieson, C. H., Jones, D. L., Visvader, J., Weissman, I. L. & Wahl, G. M. Cancer stem cells—perspectives on current status and future directions: AACR Workshop on cancer stem cells. *Cancer Res* 66, 9339-9344, doi:0008-5472. CAN-06-3126 [pii]10.1158/0008-5472. CAN-06-3126 (2006).

13 Mani, S. A., Guo, W., Liao, M. J., Eaton, E. N., Ayyanan, A., Zhou, A. Y., Brooks, M., Reinhard, F., Zhang, C. C., Shipitsin, M., Campbell, L. L., Polyak, K., Brisken, C., Yang, J. & Weinberg, R. A. The epithelial-mesenchymal transition generates cells with properties of stem cells. *Cell* 133, 704-715, doi:10.1016/j.cell.2008.03.027 (2008).

14 Marotta, L. L. & Polyak, K. Cancer stem cells: a model in the making. *Current opinion in genetics & development* 19, 44-50, doi:10.1016/j.gde.2008.12.003 (2009).

15 Mangiola, A., Lama, G., Giannitelli, C., De Bonis, P., Anile, C., Lauriola, L., La Torre, G., Sabatino, G., Maira, G., Jhanwar-Uniyal, M. & Sica, G. Stem cell marker nestin and c-Jun NH2-terminal kinases in tumor and peritumor areas of glioblastoma multiforme: possible prognostic implications. *Clin Cancer Res* 13, 6970-6977, doi:10.1158/1078-0432. CCR-07-1229 (2007).

16 Gangemi, R. M., Griffero, F., Marubbi, D., Perera, M., Capra, M. C., Malatesta, P., Ravetti, G. L., Zona, G. L., Daga, A. & Corte, G. SOX2 silencing in glioblastoma tumor-initiating cells causes stop of proliferation and loss of tumorigenicity. *Stem Cells* 27, 40-48, doi:10.1634/stemcells.2008-0493 (2009).

17 Sanai, N., Alvarez-Buylla, A. & Berger, M. S. Neural stem cells and the origin of gliomas. *N Engl J Med* 353, 811-822, doi:10.1056/NEJMra043666 (2005).

18 Galli, R., Binda, E., Orfanelli, U., Cipelletti, B., Gritti, A., De Vitis, S., Fiocco, R., Foroni, C., Dimeco, F. & Vescovi, A. Isolation and characterization of tumorigenic, stem-like neural precursors from human glioblastoma. *Cancer Res* 64, 7011-7021, doi:10.1158/0008-5472. CAN-04-1364 (2004).

19 Huntly, B. J. & Gilliland, D. G. Leukaemia stem cells and the evolution of cancer-stem-cell research. *Nat Rev Cancer* 5, 311-321 (2005).

20 Pollard, S. M., Yoshikawa, K., Clarke, I. D., Danovi, D., Stricker, S., Russell, R., Bayani, J., Head, R., Lee, M., Bernstein, M., Squire, J. A., Smith, A. & Dirks, P. Glioma stem cell lines expanded in adherent culture have tumor-specific phenotypes and are suitable for chemical and genetic screens. *Cell Stem Cell* 4, 568-580, doi:10.1016/j.stem.2009.03.014 (2009).

21 Taillandier, L., Antunes, L. & Angioi-Duprez, K. S. Models for neuro-oncological preclinical studies: solid orthotopic and heterotopic grafts of human gliomas into nude mice. *Journal of neuroscience methods* 125, 147-157 (2003).

22 Sausville, E. A. & Burger, A. M. Contributions of human tumor xenografts to anticancer drug development. *Cancer Res* 66, 3351-3354, discussion 3354, doi:10.1158/0008-5472. CAN-05-3627 (2006).

23 Joo, K. M., Kim, J., Jin, J., Kim, M., Seol, H. J., Muradov, J., Yang, H., Choi, Y. L., Park, W. Y., Kong, D. S., Lee, J. I., Ko, Y. H., Woo, H. G., Lee, J., Kim, S. & Nam, D. H. Patient-specific orthotopic glioblastoma xenograft models recapitulate the histopathology and biology of human glioblastomas in situ. *Cell reports* 3, 260-273, doi:10.1016/j.celrep.2012.12.013 (2013).

24 Gallo, M., Coutinho, F. J., Vanner, R. J., Gayden, T., Mack, S. C., Murison, A., Remke, M., Li, R., Takayama, N., Desai, K., Lee, L., Lan, X., Park, N. I., Barsyte-Lovejoy, D., Smil, D., Sturm, D., Kushida, M. M., Head, R., Cusimano, M. D., Bernstein, M., Clarke, I. D., Dick, J. E., Pfister, S. M., Rich, J. N., Arrowsmith, C. H., Taylor, M. D., Jabado, N., Bazett-Jones, D. P., Lupien, M. & Dirks, P. B. MLL5 Orchestrates a Cancer Self-Renewal State by Repressing the Histone Variant H3.3 and Globally Reorganizing Chromatin. *Cancer Cell* 28, 715-729, doi:10.1016/j.ccell.2015.10.005 (2015).

25 Trotter, K. W. & Archer, T. K. The BRG1 transcriptional coregulator. *Nucl Recept Signal* 6, e004, doi:10.1621/nrs.06004 (2008).

26 Tolstorukov, M. Y., Sansam, C. G., Lu, P., Koellhoffer, E. C., Helming, K. C., Alver, B. H., Tillman, E. J., Evans, J. A., Wilson, B. G., Park, P. J. & Roberts, C. W. M. Swi/Snf chromatin remodeling/tumor suppressor complex establishes nucleosome occupancy at target promoters. *P Natl Acad Sci USA* 110, 10165-10170, doi:10.1073/pnas.1302209110 (2013).

27 Zhang, X., Li, B., Li, W., Ma, L., Zheng, D., Li, L., Yang, W., Chu, M., Chen, W., Mailman, R. B., Zhu, J., Fan, G., Archer, T. K. & Wang, Y. Transcriptional repression by the BRG1-SWI/SNF complex affects the pluripotency of human embryonic stem cells. *Stem Cell Reports* 3, 460-474, doi:10.1016/j.stemcr.2014.07.004 (2014).

28 Ho, L., Miller, E. L., Ronan, J. L., Ho, W. Q., Jothi, R. & Crabtree, G. R. esBAF facilitates pluripotency by conditioning the genome for LIF/STAT3 signalling and by regulating polycomb function. *Nature cell biology* 13, 903-913, doi:10.1038/ncb2285 (2011).

29 Kidder, B. L., Palmer, S. & Knott, J. G. SWI/SNF-Brg1 regulates self-renewal and occupies core pluripotency-related genes in embryonic stem cells. *Stem cells* 27, 317-328, doi:10.1634/stemcells.2008-0710 (2009).

30 Singhal, N., Graumann, J., Wu, G., Arauzo-Bravo, M. J., Han, D. W., Greber, B., Gentile, L., Mann, M. & Scholer, H. R. Chromatin-Remodeling Components of the BAF Complex Facilitate Reprogramming. *Cell* 141, 943-955, doi:10.1016/j.cell.2010.04.037 (2010).

31 Gao, X., Tate, P., Hu, P., Tjian, R., Skarnes, W. C. & Wang, Z. ES cell pluripotency and germ-layer formation require the SWI/SNF chromatin remodeling component BAF250a. *Proc Natl Acad Sci USA* 105, 6656-6661, doi:10.1073/pnas.0801802105 (2008).

32 Ho, L., Ronan, J. L., Wu, J., Staahl, B. T., Chen, L., Kuo, A., Lessard, J., Nesvizhskii, A. I., Ranish, J. & Crabtree, G. R. An embryonic stem cell chromatin remodeling complex, esBAF, is essential for embryonic stem cell self-renewal and pluripotency. *Proc Natl Acad Sci USA* 106, 5181-5186, doi:10.1073/pnas.0812889106 (2009).

33 Kaeser, M. D., Aslanian, A., Dong, M. Q., Yates, J. R., 3rd & Emerson, B. M. BRD7, a novel PBAF-specific SWI/SNF subunit, is required for target gene activation and repression in embryonic stem cells. *J Biol Chem* 283, 32254-32263, doi:10.1074/jbc.M806061200 (2008).

34 Kadoch, C., Hargreaves, D. C., Hodges, C., Elias, L., Ho, L., Ranish, J. & Crabtree, G. R. Proteomic and bioinformatic analysis of mammalian SWI/SNF complexes identifies extensive roles in human malignancy. *Nat Genet* 45, 592-601, doi:10.1038/ng.2628 (2013).

35 Shain, A. H. & Pollack, J. R. The spectrum of SWI/SNF mutations, ubiquitous in human cancers. *PLoS One* 8, e55119, doi:10.1371/journal.pone.0055119 (2013).

36 Sentani, K., Oue, N., Kondo, H., Kuraoka, K., Motoshita, J., Ito, R., Yokozaki, H. & Yasui, W. Increased expression but not genetic alteration of BRG1, a component of the SWI/SNF complex, is associated with the advanced stage of human gastric carcinomas. *Pathobiology* 69, 315-320, doi:10.1159/000064638 (2001).

37 Sun, A., Tawfik, O., Gayed, B., Thrasher, J. B., Hoestje, S., Li, C. & Li, B. Aberrant expression of SWI/SNF catalytic subunits BRG1/BRM is associated with tumor development and increased invasiveness in prostate cancers. *The Prostate* 67, 203-213, doi:10.1002/pros.20521 (2007).

38 Imielinski, M., Berger, A. H., Hammerman, P. S., Hernandez, B., Pugh, T. J., Hodis, E., Cho, J., Suh, J., Capelletti, M., Sivachenko, A., Sougnez, C., Auclair, D., Lawrence, M. S., Stojanov, P., Cibulskis, K., Choi, K., de Waal, L., Sharifnia, T., Brooks, A., Greulich, H., Banerji, S., Zander, T., Seidel, D., Leenders, F., Ansen, S., Ludwig, C., Engel-Riedel, W., Stoelben, E., Wolf, J., Goparju, C., Thompson, K., Winckler, W., Kwiatkowski, D., Johnson, B. E., Janne, P. A., Miller, V. A., Pao, W., Travis, W. D., Pass, H. I., Gabriel, S. B., Lander, E. S., Thomas, R. K., Garraway, L. A., Getz, G. & Meyerson, M. Mapping the hallmarks of lung adenocarcinoma with massively parallel sequencing. *Cell* 150, 1107-1120, doi:10.1016/j.cell.2012.08.029 (2012).

39 Love, C., Sun, Z., Jima, D., Li, G., Zhang, J., Miles, R., Richards, K. L., Dunphy, C. H., Choi, W. W., Srivastava, G., Lugar, P. L., Rizzieri, D. A., Lagoo, A. S., Bernal-Mizrachi, L., Mann, K. P., Flowers, C. R., Naresh, K. N., Evens, A. M., Chadburn, A., Gordon, L. I., Czader, M. B., Gill, J. I., Hsi, E. D., Greenough, A., Moffitt, A. B., McKinney, M., Banerjee, A., Grubor, V., Levy, S., Dunson, D. B. & Dave, S. S. The genetic landscape of mutations in Burkitt lymphoma. *Nat Genet* 44, 1321-1325, doi:10.1038/ng.2468 (2012).

40 Witkowski, L., Carrot-Zhang, J., Albrecht, S., Fahiminiya, S., Hamel, N., Tomiak, E., Grynspan, D., Saloustros, E., Nadaf, J., Rivera, B., Gilpin, C., Castellsague, E., Silva-Smith, R., Plourde, F., Wu, M., Saskin, A., Arseneault, M., Karabakhtsian, R. G., Reilly, E. A., Ueland, F. R., Margiolaki, A., Pavlakis, K., Castellino, S. M., Lamovec, J., Mackay, H. J., Roth, L. M., Ulbright, T. M., Bender, T. A., Georgoulias, V., Longy, M., Berchuck, A., Tischkowitz, M., Nagel, I., Siebert, R., Stewart, C. J., Arseneau, J., McCluggage, W. G., Clarke, B. A., Riazalhosseini, Y., Hasselblatt, M., Majewski, J. & Foulkes, W. D. Germline and somatic SMARCA4 mutations characterize small cell carcinoma of the ovary, hypercalcemic type. *Nat Genet* 46, 438-443, doi:10.1038/ng.2931 (2014).

41 Le Loarer, F., Watson, S., Pierron, G., de Montpreville, V. T., Ballet, S., Firmin, N., Auguste, A., Pissaloux, D., Boyault, S., Paindavoine, S., Dechelotte, P. J., Besse, B., Vignaud, J. M., Brevet, M., Fadel, E., Richer, W., Treilleux, I., Masliah-Planchon, J., Devouassoux-Shisheboran, M., Zalcman, G., Allory, Y., Bourdeaut, F., Thivolet-Bejui, F., Ranchere-Vince, D., Girard, N., Lantuejoul, S., Galateau-Salle, F., Coindre, J. M., Leary, A., Delattre, O., Blay, J. Y. & Tirode, F. SMARCA4 inactivation defines a group of undifferentiated thoracic malignancies transcriptionally related to BAF-deficient sarcomas. *Nat Genet* 47, 1200-1205, doi:10.1038/ng.3399 (2015).

42 Hodges, H. C., Stanton, B. Z., Cermakova, K., Chang, C. Y., Miller, E. L., Kirkland, J. G., Ku, W. L., Veverka, V., Zhao, K. & Crabtree, G. R. Dominant-negative SMARCA4 mutants alter the accessibility landscape of tissue-unrestricted enhancers. *Nat Struct Mol Biol* 25, 61-72, doi:10.1038/s41594-017-0007-3 (2018).

43 Bai, J., Mei, P. J., Liu, H., Li, C., Li, W., Wu, Y. P., Yu, Z. Q. & Zheng, J. N. BRG1 expression is increased in human glioma and controls glioma cell proliferation, migration and invasion in vitro. *J Cancer Res Clin Oncol* 138, 991-998, doi:10.1007/s00432-012-1172-8 (2012).

44 Guerrero-Martinez, J. A. & Reyes, J. C. High expression of SMARCA4 or SMARCA2 is frequently associated with an opposite prognosis in cancer. *Sci Rep* 8, 2043, doi:10.1038/s41598-018-20217-3 (2018).

45 Hiramatsu, H., Kobayashi, K., Kobayashi, K., Haraguchi, T., Ino, Y., Todo, T. & Iba, H. The role of the SWI/SNF chromatin remodeling complex in maintaining the stemness of glioma initiating cells. *Sci Rep* 7, 889, doi:10.1038/s41598-017-00982-3 (2017).

46 Filippakopoulos, P. & Knapp, S. Targeting bromodomains: epigenetic readers of lysine acetylation. *Nat Rev Drug Discov* 13, 337-356, doi:10.1038/nrd4286 (2014).

47 Fedorov, O., Castex, J., Tallant, C., Owen, D. R., Martin, S., Aldeghi, M., Monteiro, O., Filippakopoulos, P., Picaud, S., Trzupek, J. D., Gerstenberger, B. S., Bountra, C., Willmann, D., Wells, C., Philpott, M., Rogers, C., Biggin, P. C., Brennan, P. E., Bunnage, M. E., Schule, R., Gunther, T., Knapp, S. & Muller, S. Selective targeting of the BRG/PB1 bromodomains impairs embryonic and trophoblast stem cell maintenance. *Sci Adv* 1, e1500723, doi:10.1126/sciadv.1500723 (2015).

48 Vangamudi, B., Paul, T. A., Shah, P. K., Kost-Alimova, M., Nottebaum, L., Shi, X., Zhan, Y., Leo, E., Mahadeshwar, H. S., Protopopov, A., Futreal, A., Tieu, T. N., Peoples, M., Heffernan, T. P., Marszalek, J. R., Toniatti, C., Petrocchi, A., Verhelle, D., Owen, D. R., Draetta, G., Jones, P., Palmer, W. S., Sharma, S. & Andersen, J. N. The SMARCA2/4 ATPase Domain Surpasses the Bromodomain as a Drug Target in SWI/SNF-Mutant Cancers: Insights from cDNA Rescue and PFI-3 Inhibitor Studies. *Cancer Res* 75, 3865-3878, doi:10.1158/0008-5472. CAN-14-3798 (2015).

49 Kwon, S. J., Park, J. H., Park, E. J., Lee, S. A., Lee, H. S., Kang, S. W. & Kwon, J. ATM-mediated phosphorylation of the chromatin remodeling enzyme BRG1 modulates DNA double-strand break repair. *Oncogene* 34, 303-313, doi:10.1038/onc.2013.556 (2015).

50 Yang, C. H., Shi, W., Basu, L., Murti, A., Constantinescu, S. N., Blatt, L., Croze, E., Mullersman, J. E. & Pfeffer, L. M. Direct association of STAT3 with the IFNAR$_1$ signal transducing chain of the type I IFN receptor. *J Biol Chem* 271, 8057-8061 (1996).

51 Akira, S., Nishio, Y., Inoue, M., Wang, X.-J., Wei, S., Matsusaka, T., Yoshida, K., Sudo, T., Naruto, M. & Kishimoto, T. Molecular Cloning of APRF, a novel IFN-stimulated gene factor 3 p91-related transcription factor involved in the gp130-mediated signaling pathway. *Cell* 77, 63-71 (1994).

52 Zhong, Z., Wen, Z. & Darnell, J. E. J. Stat3: a STAT family member activated by tyrosine phosphorylation in response to epidermal growth factor and interleukin-6. *Science* 264, 95-98 (1994).

53 Pfeffer, S. R., Fan, M., Du, Z., Yang, C. H. & Pfeffer, L. M. Unphosphorylated STAT3 regulates the antiproliferative, antiviral, and gene-inducing actions of type I interferons. *Biochem Biophys Res Commun* 490, 739-745, doi:10.1016/j.bbrc.2017.06.111 (2017).

54 Du, Z., Cai, C., Sims, M., Boop, F. A., Davidoff, A. M. & Pfeffer, L. M. The effects of type I interferon on glioblastoma cancer stem cells. *Biochem Biophys Res Commun* 491, 343-348, doi:10.1016/j.bbrc.2017.07.098 (2017).

55 Yang, C. H., Yue, J., Pfeffer, S. R., Handorf, C. R. & Pfeffer, L. M. MicroRNA miR-21 regulates the metastatic behavior of B16 melanoma cells. *J Biol Chem* 286, 39172-39178, doi:10.1074/jbc.M111.285098 (2011).

56 Yang, C. H., Yue, J., Fan, M. & Pfeffer, L. M. IFN induces miR-21 through a signal transducer and activator of transcription 3-dependent pathway as a suppressive negative feedback on IFN-induced apoptosis. *Cancer Res* 70, 8108-8116, doi:10.1158/0008-5472. CAN-10-2579 (2010).

57 Yang, C. H., Wei, L., Pfeffer, S. R., Du, Z., Murti, A., Valentine, W. J., Zheng, Y. & Pfeffer, L. M. Identification of CXCL11 as a STAT3-dependent gene induced by IFN. *J. Immunol.* 178, 986-992 (2007).

58 Yang, C. H., Murti, A., Valentine, W. J., Du, Z. & Pfeffer, L. M. Interferon alpha activates NF-κB in JAK1-deficient cells through a TYK2-dependent pathway. *J Biol Chem* 280, 25849-25853 (2005).

59 Yang, C. H., Murti, A. & Pfeffer, L. M. STAT3 complements defects in an interferon-resistant cell line: Evidence for an essential role for STAT3 in interferon signaling and biological activities. *Proc Natl Acad Sci USA* 95, 5568-5572 (1998).

60 Pfeffer, L. M., Mullersman, J. E., Pfeffer, S. R., Murti, A., Shi, W. & Yang, C. H. STAT3 as an adapter to couple phosphatidylinositol-3 kinase to the IFNAR-1 chain of the type I IFN receptor. *Science* 276, 1418-1420 (1997).

61 Turkson, J. & Jove, R. STAT proteins: novel molecular targets for cancer drug discovery. *Oncogene* 19, 6613-6626 (2000).
62 Bowman, T., Garcia, R., Turkson, J. & Jove, R. STATs in oncogenesis. *Oncogene* 19, 2474-2488 (2000).
63 Strobeck, M. W., Knudsen, K. E., Fribourg, A. F., DeCristofaro, M. F., Weissman, B. E., Imbalzano, A. N. & Knudsen, E. S. BRG-1 is required for RB-mediated cell cycle arrest. *Proc Natl Acad Sci USA* 97, 7748-7753 (2000).
64 Sang, Y. L. Temozolomide resistance in glioblastoma multiforme. *Genes & Diseases* (2016).
65 Gutenberg, A., Bock, H. C., Bruck, W., Doerner, L., Mehdorn, H. M., Roggendorf, W., Westphal, M., Felsberg, J., Reifenberger, G. & Giese, A. MGMT promoter methylation status and prognosis of patients with primary or recurrent glioblastoma treated with carmustine wafers. *Br J Neurosurg* 27, 772-778, doi:10.3109/02688697.2013.791664 (2013).
66 Kothandapani, A., Gopalakrishnan, K., Kahali, B., Reisman, D. & Patrick, S. M. Downregulation of SWI/SNF chromatin remodeling factor subunits modulates cisplatin cytotoxicity. *Exp Cell Res* 318, 1973-1986, doi:10.1016/j.yexcr.2012.06.011 (2012).
67 Park, J. H., Park, E. J., Lee, H. S., Kim, S. J., Hur, S. K., Imbalzano, A. N. & Kwon, J. Mammalian SWI/SNF complexes facilitate DNA double-strand break repair by promoting gamma-H2AX induction. *EMBO J* 25, 3986-3997, doi:10.1038/sj.emboj.7601291 (2006).
68 Qi, W., Wang, R., Chen, H., Wang, X., Xiao, T., Boldogh, I., Ba, X., Han, L. & Zeng, X. BRG1 promotes the repair of DNA double-strand breaks by facilitating the replacement of RPA with RAD51. *J Cell Sci* 128, 317-330, doi:10.1242/jcs.159103 (2015).
69 Attenello, F., Raza, S. M., Dimeco, F. & Olivi, A. Chemotherapy for brain tumors with polymer drug delivery. *Handb Clin Neurol* 104, 339-353, doi:10.1016/B978-0-444-52138-5.00022-0 (2012).
70 Ni, Z. & Bremner, R. Brahma-related gene 1-dependent STAT3 recruitment at IL-6-inducible genes. *J Immunol* 178, 345-351 (2007).
71 Ito, K., Noguchi, A., Uosaki, Y., Taga, T., Arakawa, H. & Takizawa, T. Gfap and Osmr regulation by BRG1 and STAT3 via interchromosomal gene clustering in astrocytes. *Mol Biol Cell* 29, 209-219, doi:10.1091/mbc.E17-05-0271 (2018).
72 Giraud, S., Hurlstone, A., Avril, S. & Coqueret, O. Implication of BRG1 and cdk9 in the STAT3-mediated activation of the p21waf1 gene. *Oncogene* 23, 7391-7398, doi:10.1038/sj.onc.1207972 (2004).
73 Souma, Y., Nishida, T., Serada, S., Iwahori, K., Takahashi, T., Fujimoto, M., Ripley, B., Nakajima, K., Miyazaki, Y., Mori, M., Doki, Y., Sawa, Y. & Naka, T. Antiproliferative effect of SOCS-1 through the suppression of STAT3 and p38 MAPK activation in gastric cancer cells. *Int J Cancer* 131, 1287-1296, doi:10.1002/ijc.27350 (2012).
74 Megeney, L. A., Perry, R. L. S., Lecouter, J. E. & Rudnicki, M. A. bFGF and LIF signaling activates STAT3 in proliferating myoblasts. *Dev Genet* 19, 139-145, doi: Doi 10.1002/(Sici)1520-6408(1996)19:2<139:: Aid-Dvg5>3.0. Co; 2-A (1996).
75 Huang, M., Qian, F., Hu, Y., Ang, C., Li, Z. & Wen, Z. Chromatin-remodelling factor BRG1 selectively activates a subset of interferon-alpha-inducible genes. *Nat Cell Biol* 4, 774-781, doi:10.1038/ncb855 (2002).
76 Malta, T. M., Sokolov, A., Gentles, A. J., Burzykowski, T., Poisson, L., Weinstein, J. N., Kaminska, B., Huelsken, J., Omberg, L., Gevaert, O., Colaprico, A., Czerwinska, P., Mazurek, S., Mishra, L., Heyn, H., Krasnitz, A., Godwin, A. K., Lazar, A. J., Cancer Genome Atlas Research, N., Stuart, J. M., Hoadley, K. A., Laird, P. W., Noushmehr, H. & Wiznerowicz, M. Machine Learning Identifies Stemness Features Associated with Oncogenic Dedifferentiation. *Cell* 173, 338-354 e315, doi:10.1016/j.cell.2018.03.034 (2018).

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound having the structure of Formula (I):

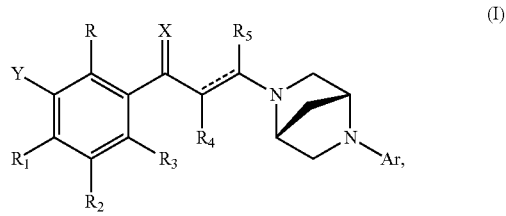

wherein:

━━━━ represents a single or double bond;

Ar is selected from cycloalkyl, substituted cycloalkyl, aryl, substituted aryl, heteroaryl, and substituted heteroaryl;

R is H, halo, amino, thiol, or hydroxy; and Y is H or halo; or where R and Y together from a group selected from —N=CH—NH—, —N=N—NH—, and —CH=N—NH—;

$R_1$ and $R_2$ are each independently selected from the group consisting of H, cyano, halo, alkyl, substituted alkyl, perhaloalkyl, alkoxy, cycloalkyl, substituted cycloalkyl, cycloalkenyl, and substituted cycloalkenyl;

$R_3$, $R_4$ and $R_5$ are each H; and

X is O, S, or NH; or wherein (i) X and $R_5$ together comprise —N—NH— and/or wherein $R_3$ and $R_4$ together form an alkylene group, optionally ethylene or (ii) $R_3$ and $R_5$ together form a covalent bond or methylene group;

or a pharmaceutically acceptable salt thereof, subject to the proviso that the compound is not PFI-3.

2. The compound of claim 1, wherein Ar is selected phenyl or pyridinyl, optionally substituted with one or more aryl group substituents, further optionally wherein the one or more aryl group substituents are selected from halo, alkoxy, and cyano.

3. The compound of claim 1, wherein the compound of Formula (I) has a structure of Formula (II):

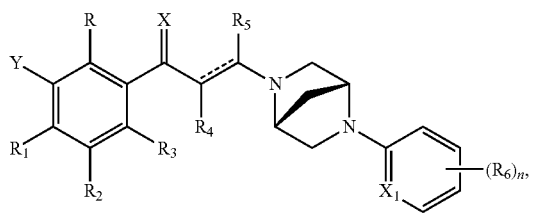
(II)

wherein ----- R, Y, X, and $R_1$-$R_5$ are as defined for the compound of Formula (I) and wherein $X_1$ is CH, C ($R_7$), or N; n is an integer from 0 to 4; and each $R_6$ and $R_7$ is independently selected from cyano, halo, amino, alkyl, substituted alkyl, hydroxy, alkoxy, and perhaloalkyl; or a pharmaceutically acceptable salt thereof.

4. The compound of claim 3, wherein n is 0, 1, or 2 and wherein each $R_6$ is independently selected from fluoro, chloro, methoxy, and cyano.

5. The compound of claim 3, wherein X is O, $X_1$ is N and wherein R and Y together form a group selected from —N=CH—NH—, —N=N—NH—, and —CH=N—NH—.

6. The compound of claim 3, wherein X and $R_5$ together comprise —N—NH, optionally wherein R is OH and $R_2$ is H, fluoro, chloro, or bromo.

7. The compound of claim 3, wherein X is O, R is OH, and $R_2$ is selected from H, fluoro, chloro, and bromo, optionally wherein $R_2$ is fluoro or bromo.

8. The compound of claim 7, wherein $R_3$ and $R_4$ together form an ethylene group.

9. The compound of claim 3, wherein the compound of Formula (II) has a structure of Formula (III):

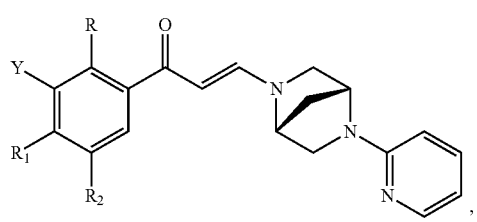
(III)

wherein:
R is selected from H, hydroxy and halo;
Y is H or halo; and
$R_1$ and $R_2$ are independently selected from H, cyano and halo, subject to the proviso that when R is hydroxy, Y is halo and/or at least one of $R_1$ and $R_2$ is cyano or halo; or a pharmaceutically acceptable salt thereof.

10. The compound of claim 9, wherein one of R, $R_1$, and $R_2$ is selected from fluoro, chloro, and bromo.

11. The compound of claim 9, wherein the compound of Formula (III) is selected from:

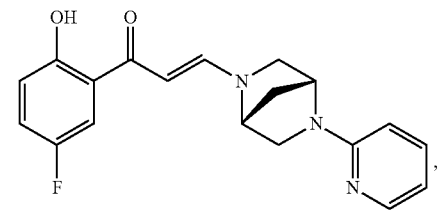 [SMILES: O=C(/C=C/N1C[C@H]2C[C@@H]1CN2c1ccccn1)c1ccccc1O]

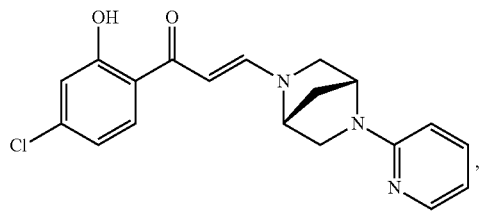

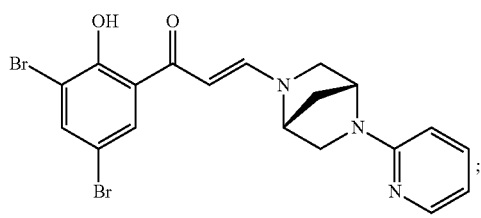

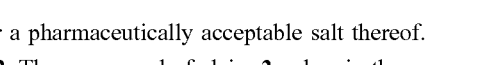

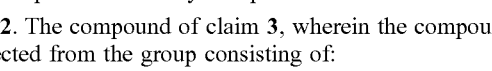, and

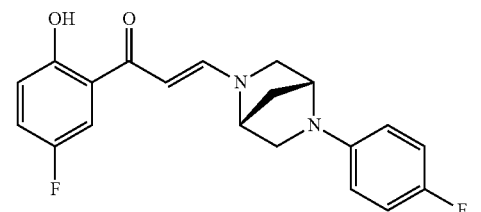;

or a pharmaceutically acceptable salt thereof.

12. The compound of claim 3, wherein the compound is selected from the group consisting of:

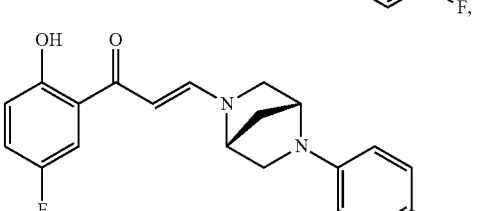

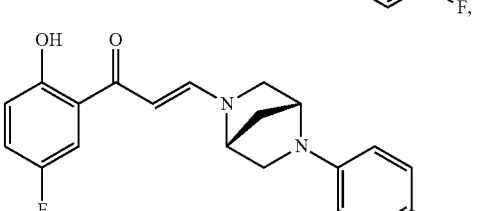

-continued

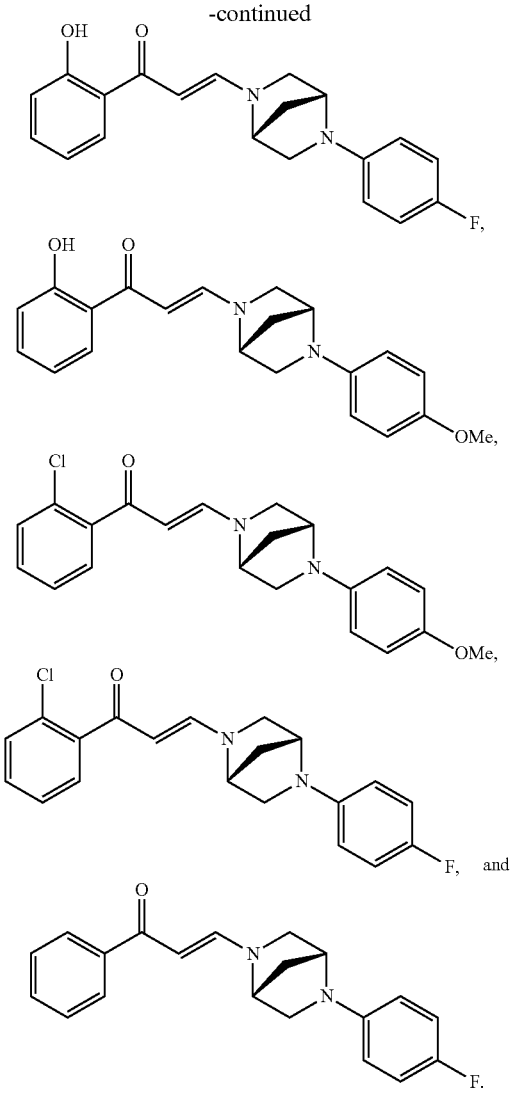

13. A pharmaceutical formulation comprising a pharmaceutically acceptable carrier and a compound of ene of claim 1.

14. A method of treating glioblastoma in a subject in need thereof, the method comprising:
(a) administering to the subject a compound of Formula (I)

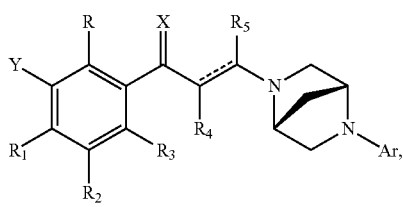

wherein:
- ----- represents a single or double bond;
- Ar is selected from cycloalkyl, substituted cycloalkyl, aryl, substituted aryl, heteroaryl, and substituted heteroaryl;
- R is H, halo, amino, thiol, or hydroxy and Y is H or halo; or
- wherein R and Y together form a group selected from —N=CH—NH—, —N=N—NH—, and —CH=N—NH—;
- $R_1$ and $R_2$ are each independently selected from the group consisting of H, cyano, halo, alkyl, substituted alkyl, perhaloalkyl, alkoxy, cycloalkyl, substituted cycloalkyl, cycloalkenyl, and substituted cycloalkenyl;
- $R_3$, $R_4$ and $R_5$ are each H; and
- X is O, S, or NH; or
- wherein (i) X and $R_5$ together comprise —N—NH— and/or $R_3$ and $R_4$ together form an alkylene group, optionally ethylene or (ii) $R_3$ and $R_5$ together form a covalent bond or methylene group;
- or a pharmaceutically acceptable salt thereof, and optionally wherein the compound of Formula (I) is not PFI-3; and (b) administering to the subject a chemotherapeutic compound, wherein said chemotherapeutic compound is a DNA alkylating agent.

15. The method of claim 14, wherein the DNA alkylating agent is temozolomide (TMZ) or carmustine.

16. The method of claim 14, wherein Ar is selected phenyl or pyridinyl, optionally substituted with one or more aryl group substituents, further optionally wherein the one or more aryl group substituents are selected from halo, alkoxy, and cyano.

17. The method of claim 14, wherein the compound of Formula (I) has a structure of Formula (II):

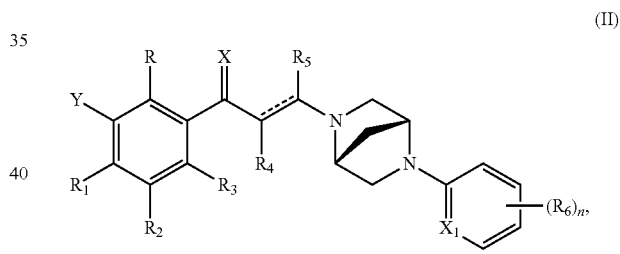

wherein ----- R, Y, X, and $R_1$-$R_5$ are as defined for the compound of Formula (I) and wherein $X_1$ is CH, C($R_7$), or N; n is an integer from 0 to 4; and each $R_6$ and $R_7$ is independently selected from cyano, halo, amino, alkyl, substituted alkyl, hydroxy, alkoxy, and perhaloalkyl; or a pharmaceutically acceptable salt thereof.

18. The method of claim 17, wherein n is 0, 1, or 2 and wherein each $R_6$ is independently selected from fluoro, chloro, methoxy, and cyano.

19. The method of claim 17, wherein X is O, $X_1$ is N and wherein R and Y together form a group selected from —N=CH—NH—, —N=N—NH—, and —CH=N—NH—.

20. The method of claim 17, wherein X and $R_5$ together comprise —N—NH, optionally wherein R is OH and $R_2$ is H, fluoro, chloro, or bromo.

21. The method of claim 17, wherein X is O, R is OH, and $R_2$ is selected from H, fluoro, chloro, and bromo, optionally wherein $R_2$ is fluoro or bromo.

22. The method of claim 21, wherein $R_3$ and $R_4$ together form an ethylene group.

23. The method of claim 17, wherein the compound of Formula (II) has a structure of Formula (III):

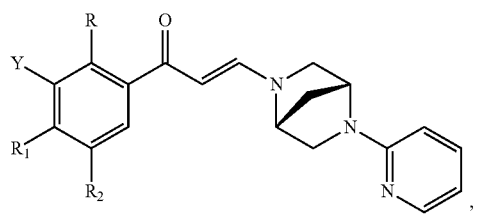

(III)

wherein:
R is selected from H, hydroxy and halo;
Y is H or halo; and
R$_1$ and R$_2$ are independently selected from H, cyano and halo, optionally wherein when R is hydroxy, Y is halo and/or at least one of R$_1$ and R$_2$ is cyano or halo;
or a pharmaceutically acceptable salt thereof.

24. The method of claim 23, wherein one of R, R$_1$, and R$_2$ is selected from fluoro, chloro, and bromo.

25. The method of claim 23, wherein the compound of Formula (III) is selected from:

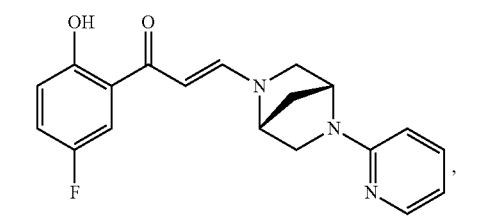

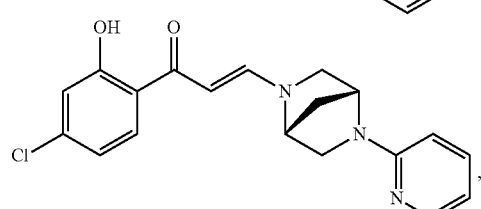

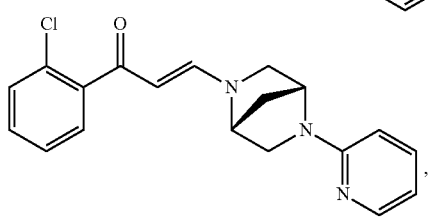

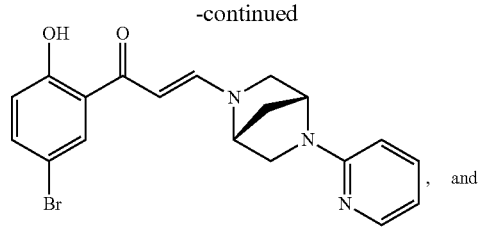

and

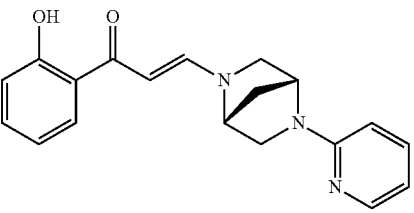

or a pharmaceutically acceptable salt thereof.

26. The method of claim 14, wherein the compound of Formula (I) is PFI-3:

27. The method of claim 14, wherein the glioblastoma is a DNA alkylating agent-resistant glioblastoma.

28. A method of inhibiting Brahma-related gene 1 (BRG1) bromodomain, the method comprising contacting a sample comprising BRG1 with a compound of claim 1.

* * * * *